(12) United States Patent
Andrews et al.

(10) Patent No.: US 8,138,188 B2
(45) Date of Patent: Mar. 20, 2012

(54) MELANOCORTIN TYPE 4 RECEPTOR AGONIST PIPERIDINOYLPYRROLIDINES

(75) Inventors: Mark David Andrews, Sandwich (GB); Alan Daniel Brown, Sandwich (GB); Mark Ian Lansdell, Sandwich (GB); Nicholas William Summerhill, Sandwich (GB)

(73) Assignee: Pfizer Inc., New York, NY (US)

( * ) Notice: Subject to any disclaimer, the term of this patent is extended or adjusted under 35 U.S.C. 154(b) by 880 days.

(21) Appl. No.: 12/280,444

(22) PCT Filed: Feb. 19, 2007

(86) PCT No.: PCT/IB2007/000456
§ 371 (c)(1),
(2), (4) Date: Aug. 22, 2008

(87) PCT Pub. No.: WO2007/096763
PCT Pub. Date: Aug. 30, 2007

(65) Prior Publication Data
US 2009/0036459 A1 Feb. 5, 2009

Related U.S. Application Data

(60) Provisional application No. 60/776,295, filed on Feb. 23, 2006, provisional application No. 60/887,840, filed on Feb. 2, 2007.

(51) Int. Cl.
C07D 401/14 (2006.01)
A61K 31/4402 (2006.01)
A61P 15/00 (2006.01)
A61P 3/00 (2006.01)

(52) U.S. Cl. ............... 514/252.03; 514/333; 546/256; 544/238

(58) Field of Classification Search .......... 514/248, 514/269, 274, 338, 340, 341; 544/238, 316, 544/236; 546/279.1
See application file for complete search history.

(56) References Cited

U.S. PATENT DOCUMENTS

| | | | |
|---|---|---|---|
| 3,752,814 A | 8/1973 | Fluckiger et al. | 260/268 |
| 3,752,888 A | 8/1973 | Fluckiger et al. | 424/250 |
| 4,929,629 A | 5/1990 | Jefferey et al. | 514/646 |
| 5,274,143 A | 12/1993 | Ramig et al. | 554/123 |
| 5,420,305 A | 5/1995 | Ramig et al. | 549/292 |
| 5,521,186 A | 5/1996 | Heeres et al. | 514/252 |
| 5,540,917 A | 7/1996 | Isler et al. | 424/78.01 |
| 5,624,941 A | 4/1997 | Barth et al. | 514/326 |
| 5,643,874 A | 7/1997 | Bremer et al. | 514/12 |
| 5,747,524 A | 5/1998 | Cullinan et al. | 514/443 |
| 5,929,075 A | 7/1999 | Heeres et al. | 514/252 |
| 6,265,431 B1 | 7/2001 | Muller et al. | 514/408 |
| 6,432,984 B1 | 8/2002 | Barthe et al. | 514/326 |
| 6,518,264 B2 | 2/2003 | Archard et al. | 514/210.01 |
| 7,151,097 B2 | 12/2006 | Carpino et al. | 514/211.05 |
| 2002/0141985 A1 | 10/2002 | Pittner et al. | 424/94.1 |
| 2004/0092520 A1 | 5/2004 | Griffith et al. | 514/242 |
| 2004/0157839 A1 | 8/2004 | Griffith et al. | 514/227.8 |
| 2004/0214838 A1 | 10/2004 | Carpino et al. | 514/262.1 |
| 2004/0214855 A1 | 10/2004 | Carpino et al. | 514/303 |
| 2005/0176772 A1 | 8/2005 | Calabrese et al. | 514/326 |
| 2011/0136814 A1 | 6/2011 | Andrews et al. | 514/248 |

FOREIGN PATENT DOCUMENTS

| | | |
|---|---|---|
| WO | WO0035298 | 6/2000 |
| WO | WO02068387 | 9/2002 |
| WO | WO02068388 | 9/2002 |
| WO | WO02076949 | 10/2002 |
| WO | WO03027637 | 4/2003 |
| WO | WO03075660 | 9/2003 |
| WO | WO2004012671 | 2/2004 |
| WO | WO2004013120 | 2/2004 |
| WO | WO2004048317 | 6/2004 |
| WO | WO2007015162 | 8/2007 |

OTHER PUBLICATIONS

Wessells, et al., Peptides, vol. 26, # 10, Oct. 2005, pp. 1972-1977, The Melanocortin Pathway 2005.*
Verty, et al., Energy Balance/Obesity, 145 (7): 3224, 2004.*
Wagner, et al., Clinical Pharmacology & Therapeutics (2009) 86 6, 659-666.*
Chaki, et al., Drugs of the Future, The MC4 receptor as a therapeutic target, vol. 29(10), pp. 1065-1074, (2004).
Fan, et al., Nature, Role of melanocortinergic neurons in feeding and the agouti obesity syndrome, vol. 385, pp. 165-168, (1997).
Harper, et al., Journal of Medicinal Chemistry, Synthesis of some N-substituted 3,5-dimethyl-4-piperidinols and their derivatives as potential analgesics. vol. 7(6), pp. 726-728 (1964).
Hinney, et al., Journal of Clinical Endocrinology and Metabolism, Several mutations in the melanocortin-4 receptor gene including a nonsense and a frameshift mutation associated with dominantly inherited obesity in humans, vol. 84(4), pp. 1483-1486, (1999).
Huszar, et al. Cell (Cambridge, Massachusetts), Targeted disruption of the melanocortin-4 receptor results in obesity in mice. vol. 88(1), pp. 131-141, (1997).

(Continued)

Primary Examiner — James O Wilson
Assistant Examiner — Cecilia M Jaisle
(74) Attorney, Agent, or Firm — Gregg C. Benson; John A. Wichtowski

(57) ABSTRACT

The present invention relates to a class of melanocortin MCR4 agonists of general formula (I)

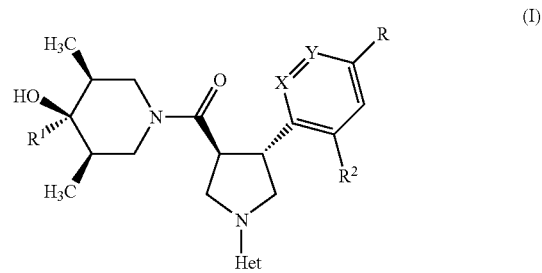

(I)

wherein the variables and substituents are as defined herein and especially to selective MCR4 agonist compounds, to their use in medicine, particularly in the treatment of sexual dysfunction and obesity, to intermediates useful in their synthesis and to compositions containing them.

19 Claims, 1 Drawing Sheet

OTHER PUBLICATIONS

Liang, et al., *Expert Opinion in Therapeutic Patents*, "Fast-dissolving intraoral drug deliver system", vol. 11 (6), 981-986, (2001).

Lieberman, et al., Pharmaceutical Dosage Forms: Tablets, vol. 1, (1980).

Lu, et al., Nature, Agouti protein is an antagonist of the melanocyte-stimulating-hormone receptor, vol. 371, pp. 799-802, (1994).

March, Jerry; *Advanced Organic Chemistry*: Reactions, Mechanisms, and Structure, Fourth Edition, pp. 378-383, (1992).

Mizuno, et al., *Endocrinology*, Fasting regulates hypothalamic neuropeptide Y, agouti-related peptide, and proopiomelanocortin in diabetic mice independent of changes in leptin or insulin, vol. 140(10), pp. 4551-4557, (1999).

Ollmann, et al., *Science*, Antagonism of Central Melanocortin Receptors in Vitro and in Vivo by Agouti-Related Protein, vol., pp. 135-138., (1997).

Vaisse, et al., *Nature Genetics*, A frameshift mutation in human MC4R is associated with a dominant form of obesity, vol. 20(2), pp. 113-114, (1998).

Verma et al., *Pharmaceutical Technology On-line*, "Drug delivery technologies and future directions", vol. 25(2), 1-14,(2001).

Wikberg, et al., *Pharmacological Research*, "New Aspects on the Melanocortins and Their Receptors", vol. 42(5), pp. 393-420, (2000).

Yang, et al., *Molecular Endocrinology*, Characterization of Agouti-related protein binding to melanocortin receptors, vol. 13(1), pp. 148-155, (1999).

Yeo, et al., *Nature Genetics*, A frameshift mutation in MC4R associated with dominantly inherited human obesity, vol. 20, pp. 111-112, (Oct. 1998).

Benoit et al., The Journal of Neuroscience, May 1, 2000, 20(9), pp. 3442-3448.

\* cited by examiner

MELANOCORTIN TYPE 4 RECEPTOR AGONIST PIPERIDINOYLPYRROLIDINES

This application is a national stage application under 35 U.S.C. 371 of PCT/IB/2007/000456, filed Feb. 19, 2007, which claims the benefit of U.S. Provisional Patent Application No. 60/887,840, filed on Feb. 2, 2007 and of U.S. Provisional Patent Application No. 60/776,295, filed on Feb. 23, 2006.

This present invention relates to a certain class of compounds, and their pharmaceutically acceptable salts, solvates and prodrugs thereof, which are agonists at the melanocortin 4 (MC4) receptor, especially to selective MC4 agonist compounds, to their use in medicine, to compositions containing them, to processes for their preparation and to intermediates used in such processes. In particular the present invention relates to a class of MCR4 agonist piperidinoylpyrrolidine compounds useful for the treatment of sexual dysfunctions, obesity, diabetes and other disorders. [The terms "MC4", "MC4 receptor", "MCR4", "MC4-R", etc. are used interchangeably herein.]

Melanocortins are peptides derived from pro-opiomelanocortins (POMC) that bind to and activate G-protein coupled receptors (GPCR's) of the melanocortin receptor family. Melanocortins regulate a diverse number of physiological processes including sexual function and sexual behaviour, food intake and metabolism. There are five melanocortin receptors that have been cloned, MCR1, MCR2, MCR3, MCR4, MCR5, and are expressed in various tissues. MCR1 is specifically expressed in melanocytes and melanoma cells, MCR2 is the ACTH receptor and is expressed in adrenal tissue, MCR3 is predominantly expressed in the brain and limbic system, MCR4 is widely expressed in the brain and spinal cord, and MCR5 is expressed in the brain and many peripheral tissues including skin, adipose tissue, skeletal muscle, and lymphoid tissue. MCR3 may be involved in the control of sexual function, food intake and thermogenesis.

MC4-R is a G-protein-coupled seven-transmembrane receptor primarily expressed in the hypothalamus, hippocampus, and thalamus (Gantz et al. 1993 *J Biol Chem* 268:15174-15179). The receptor is implicated in the central regulation of body weight: MC4-R is activated by α-melanocyte-stimulating hormone (MSH), which is derived from pro-opiomelanocortin and is inactivated by agouti gene-related protein (AGRP). α-MSH induces weight loss, whereas the ectopic expression of agouti protein results in obesity in the agouti mice (Fan et al. 1993 *Nature* 385:165-168; Lu et al. 1994 *Nature* 371:799-802). Additional evidence for the role of MC4-R in weight regulation stems from both a knockout model in mice (Huszar et al. 1997 *Cell* 88:131 141) and haploinsufficiency mutations in humans (Vaisse et al. 1998 *Nat Genet.* 20:113 114; Yeo et al. 1998 *Nat Genet.* 20:111 112; Hinney et al. 1999 *J Clin Endocrinol Metab* 84:1483 1486). In MC4-R knockout mice, an increased body weight was discernible by age 5 wk. By age 15 wk, homozygous mutant females were, on average, twice as heavy as their wild-type littermates, whereas homozygous mutant males were ~50% heavier than wild-type controls. Mice heterozygous for the MC4-R knockout showed a weight gain intermediate to that seen in wild-type and homozygous mutant littermates, thus demonstrating a gene dosage effect of MC4-R ablation on body-weight regulation. The food intake of homozygous mutants was increased by ~50% in comparison to that in wild-type sibs (Huszar et al. 1997 *Cell* 88:131 141). [From *Am. J. Hum. Genet.,* 65:1501-1507, 1999]. MCR4 activation has been shown to induce penile erection in rodents and MCR4 inactivation has been shown to cause obesity (reviewed in Hadley, 1999, Ann N Y Acad. Sci., 885:1-21, Wikberg et al 2000, Pharmacol Res., 42(5), 393-420).

Chaki and Nakazato, in Drugs Of The Future, 2004, 29(10): 1065-1074, refer to potential therapeutic applications for ligands acting at the MC4 receptor. International Patent Application publication numbers WO 2005/077935, WO 02/068387 and WO 02/068388, and International Patent Application PCT/IB2006/002151 refer to certain piperidinylcarbonylpyrrolidines as MC4 agonists useful in treating sexual dysfunctions, obesity, diabetes and other disorders. The preceding publications are hereby incorporated by reference in their entirety, with regard to the therapeutic aspects of the MC4 agonists of this invention.

Figure 1:
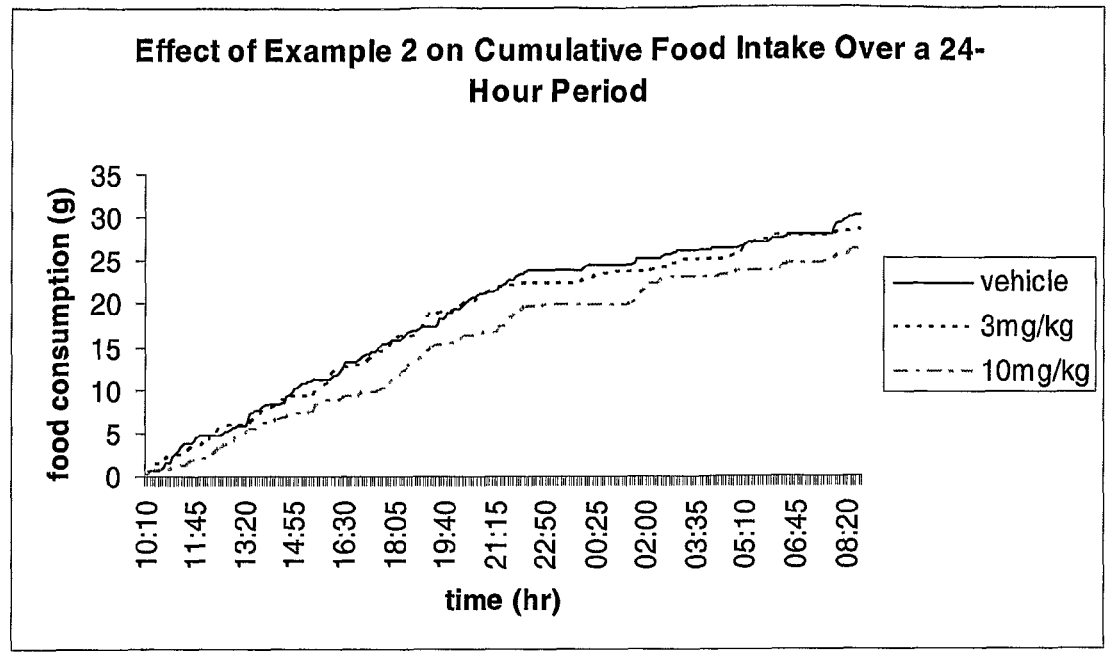
FIG. 1 shows the effects of the compound of Example 2 at 3 mg/kg and 10 mg/kg and vehicle on cumulative food intake over 24 hours.

Compounds of the present invention are useful in treating diseases, disorders or conditions responsive to activation of the MC4 receptor, including:

male and female sexual dysfunctions including hypoactive sexual desire disorder, sexual arousal disorder, orgasmic disorder and/or sexual pain disorder in females, male erectile dysfunction;

obesity (by reducing appetite, increasing metabolic rate, reducing fat intake or reducing carbohydrate craving); and diabetes mellitus (by enhancing glucose tolerance and/or decreasing insulin resistance).

The compounds of the invention are potentially useful in treating further diseases, disorders or conditions including, but not limited to, hypertension, hyperlipidemia, osteoarthritis, cancer, gall bladder disease, sleep apnea, depression, anxiety, compulsion, neuroses, insomnia/sleep disorder, substance abuse, pain, fever, inflammation, immune modulation, rheumatoid arthritis, skin tanning, acne and other skin disorders, neuroprotective and cognitive and memory enhancement including the treatment of Alzheimer's disease, treatment of Lower Urinary Tract Dysfunction (including Urinary Incontinence—overactive bladder, increased daytime frequency, nocturia, urgency, urinary incontinence (any condition in which there is an involuntary leakage of urine), including stress urinary incontinence, urge urinary incontinence and mixed urinary incontinence, overactive bladder with associated urinary incontinence, enuresis, nocturnal enuresis, continuous urinary incontinence, situational urinary incontinence such as incontinence during sexual intercourse, and lower urinary tract symptoms (LUTS) associated with benign prostatic hyperplasia (BPH)), and any other indications mentioned in the above-referenced patent applications. Compounds of the present invention are particularly suitable for treating female sexual dysfunction, male erectile dysfunction, obesity, diabetes, and conditions of Lower Urinary Tract Dysfunction.

The terms "treating", "treat", or "treatment" as used herein are intended to embrace both prevention and control i.e., prophylactic, and palliative treatment of the indicated conditions.

Desirable properties for MCR4 agonist compounds of the present invention include: desirable MCR4 agonist potencies as detailed hereinafter; selectivity for MCR4 agonism versus MCR1, and/or MCR5, and/or MCR3 as detailed hereinafter; both desirable MC4R agonist potency and selectivity for MCR4 versus, MCR1, and/or MCR5, and/or MCR3; good biopharmaceutical properties such as physical stability; solubility; oral bioavailability; appropriate metabolic stability; ability to displace AGRP from the MC4 receptor.

The present invention provides for compounds of formula (I):

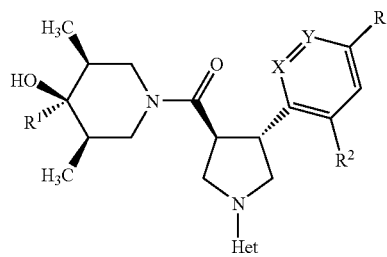

wherein
one of X and Y is N and the other is CH,
R is F, Cl, CN, CF$_3$ or methoxy, with the proviso that when Y is N, R is not F or Cl,
R$^1$ is phenyl, 2-pyridyl, C$_3$-C$_6$ cycloalkyl or CH$_2$(C$_3$-C$_6$ cycloalkyl), wherein the ring moiety is optionally substituted by one or more substituents independently selected from F, Cl, CN, methyl and methoxy,
R$^2$ is H, F or Cl, with the proviso that when Y is N, R$^2$ is not F or Cl,
Het is a 6-membered ring containing one or 2 N atoms, wherein the ring is either aromatic, or contains 2 double bonds in the ring and a =O substituent, which ring is optionally substituted by one or more substituents independently selected from F, Cl, OH, CN, methyl, ethyl, NH$_2$, NHCH$_3$, N(CH$_3$)$_2$ and methoxy,
or alternatively, Het is a 6-membered ring containing one or 2 N atoms fused at the 3,4-positions, relative to the attachment to the pyrrolidine ring, to a 5-membered aromatic ring containing one or two further N atoms, which 5-membered ring is optionally substituted by OH.
and the pharmaceutically acceptable salts, solvates (including hydrates), and prodrugs thereof.

Non-limiting examples of suitable "Het" groups are shown below:

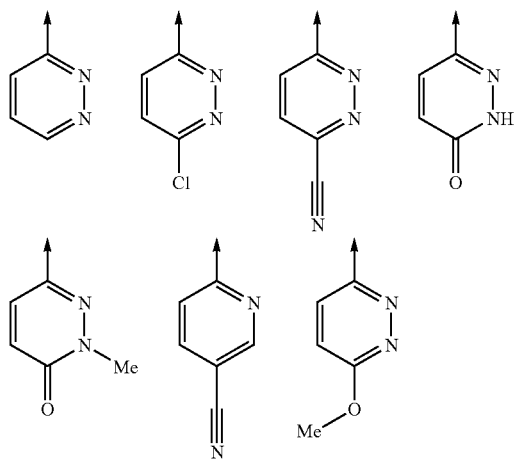

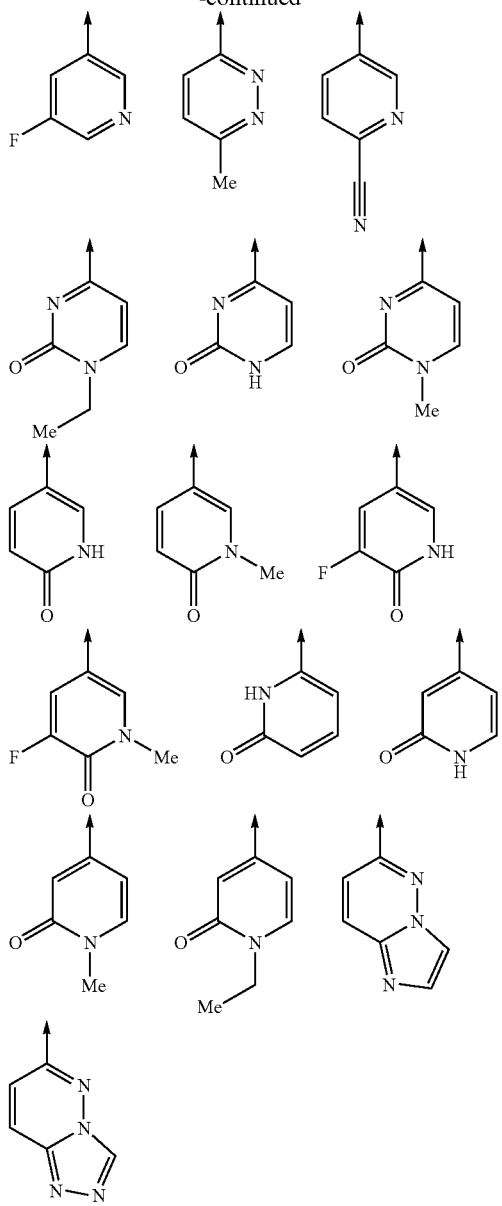

Preferably X is N and Y is CH.
Preferably R is chloro.
Preferably R$^1$ is phenyl optionally substituted by one or more substituents independently selected from F, Cl, CN, methyl and methoxy.
More preferably R$^1$ is phenyl, 4-chlorophenyl or 4-fluorophenyl.
In an alternative embodiment R$^1$ is preferably C$_3$-C$_6$ cycloalkyl, more preferably cyclopropyl or cyclohexyl.
Preferably R$^2$ is H or F.
More preferably R$^2$ is H.
Preferably Het is pyridin-2-yl, pyridin-3-yl, pyridazin-3-yl, 6-oxo-1,6-dihydropyridazin-3-yl, 6-oxo-1,6-dihydropyridin-3-yl, 2-oxo-1,2-dihydropyrimidin-4-yl, 6-oxo-1,6-dihydropyrimidin-4-yl, 2-oxo-1,2-dihydropyridin-4-yl, imidazo[1,2-b]pyridazin-6-yl, [1,2,4]triazolo[4,3-b]pyridazin-6-yl or 6-oxo-1,6-dihydropyridin-2-yl, optionally substituted by one or more substituents independently selected from F, Cl, OH, CN, methyl, ethyl and methoxy.

More preferably Het is pyridin-2-yl, pyridin-3-yl, pyridazin-3-yl or 6-oxo-1,6-dihydropyridazin-3-yl, optionally substituted by one or more substituents independently selected from OH, CN, F, methyl and methoxy.

Yet more preferably Het is pyridin-2-yl or pyridazin-3-yl, each of which is substituted at the para-position relative to the bond linking to the pyrrolidine moiety, by OH, CN or methoxy.

Most preferably Het is pyridazin-3-yl substituted at the para-position relative to the bond linking to the pyrrolidine moiety, by OH, CN or methoxy.

A preferred group of compounds, salts, solvates and prodrugs include those wherein:

$R^1$ has the value associated with the following specific compounds.

A preferred group of compounds, salts, solvates and prodrugs include those wherein:

R has the value associated with the following specific compounds.

A preferred group of compounds, salts, solvates and prodrugs include those wherein:

$R^2$ has the value associated with the following specific compounds.

A preferred group of compounds, salts, solvates and prodrugs include those wherein:

Het has the value associated with the following specific compounds.

A further preferred group of compounds, salts, solvates and prodrugs include those wherein:

R, $R^1$, $R^2$ and Het have the values associated with the following specific compounds.

Preferably the compound is selected from:

6-[(3S,4S)-3-(5-chloropyridin-2-yl)-4-{[(3R,4R,5S)-4-(4-fluorophenyl)-4-hydroxy-3,5-dimethylpiperidin-1-yl]carbonyl}pyrrolidin-1-yl]pyridazine-3-carbonitrile;

6-[(3S,4S)-3-(5-chloropyridin-2-yl)-4-{[(3R,4R,5S)-4-hydroxy-3,5-dimethyl-4-phenylpiperidin-1-yl]carbonyl}pyrrolidin-1-yl]pyridazine-3-carbonitrile;

6-[(3S,4S)-3-(5-chloropyridin-2-yl)-4-{[(3R,4R,5S)-4-hydroxy-3,5-dimethyl-4-pyridin-2-ylpiperidin-1-yl]carbonyl}pyrrolidin-1-yl]pyridazine-3-carbonitrile;

6-[(3S,4S)-3-(5-chloropyridin-2-yl)-4-{[(3R,4R,5S)-4-hydroxy-3,5-dimethyl-4-phenylpiperidin-1-yl]carbonyl}pyrrolidin-1-yl]pyridazin-3(2H)-one;

6-[(3S,4S)-3-(5-chloropyridin-2-yl)-4-{[(3R,4R,5S)-4-hydroxy-3,5-dimethyl-4-phenylpiperidin-1-yl]carbonyl}pyrrolidin-1-yl]-2-methylpyridazin-3(2H)-one;

6-[(3S,4S)-3-{[(3R,4R,5S)-4-(4-chlorophenyl)-4-hydroxy-3,5-dimethylpiperidin-1-yl]carbonyl}-4-(5-chloropyridin-2-yl)pyrrolidin-1-yl]-2-methylpyridazin-3(2H)-one;

6-[(3S,4S)-3-(5-chloropyridin-2-yl)-4-{[(3R,4R,5S)-4-(5-chloropyridin-2-yl)-4-hydroxy-3,5-dimethylpiperidin-1-yl]carbonyl}pyrrolidin-1-yl]-2-methylpyridazin-3(2H)-one;

6-[(3S,4S)-3-(5-chloropyridin-2-yl)-4-{[(3R,4R,5S)-4-(3,4-difluorophenyl)-4-hydroxy-3,5-dimethylpiperidin-1-yl]carbonyl}pyrrolidin-1-yl]-2-methylpyridazin-3(2H)-one;

6-[(3S,4S)-3-(5-chloropyridin-2-yl)-4-{[(3R,4R,5S)-4-hydroxy-4-(4-methoxyphenyl)-3,5-dimethylpiperidin-1-yl]carbonyl}pyrrolidin-1-yl]-2-methylpyridazin-3(2H)-one;

6-[(3S,4S)-3-(5-chloropyridin-2-yl)-4-{[(3R,4R,5S)-4-cyclohexyl-4-hydroxy-3,5-dimethylpiperidin-1-yl]carbonyl}pyrrolidin-1-yl]-2-methylpyridazin-3(2H)-one;

(3R,4R,5S)-1-{[(3S,4S)-1-(6-chloropyridazin-3-yl)-4-(5-chloropyridin-2-yl)pyrrolidin-3-yl]carbonyl}-4-(4-fluorophenyl)-3,5-dimethylpiperidin-4-ol;

(3R,4R,5S)-1-{[(3S,4S)-4-(5-chloropyridin-2-yl)-1-(6-methoxypyridazin-3-yl)pyrrolidin-3-yl]carbonyl}-4-cyclopropyl-3,5-dimethylpiperidin-4-ol;

(3R,4R,5S)-1-{[(3S,4S)-4-(5-chloropyridin-2-yl)-1-(5-fluoropyridin-3-yl)pyrrolidin-3-yl]carbonyl}-4-(4-fluorophenyl)-3,5-dimethylpiperidin-4-ol;

6-[(3S,4S)-3-(5-chloropyridin-2-yl)-4-{[(3R,4R,5S)-4-(4-fluorophenyl)-4-hydroxy-3,5-dimethylpiperidin-1-yl]carbonyl}pyrrolidin-1-yl]nicotinonitrile;

6-[(3S,4S)-3-{[(3R,4R,5S)-4-(4-fluorophenyl)-4-hydroxy-3,5-dimethylpiperidin-1-yl]carbonyl}-4-(5-fluoropyridin-2-yl)pyrrolidin-1-yl]pyridazine-3-carbonitrile;

6-[(3S,4S)-3-(5-fluoropyridin-2-yl)-4-{[(3R,4R,5S)-4-hydroxy-3,5-dimethyl-4-phenylpiperidin-1-yl]carbonyl}pyrrolidin-1-yl]pyridazine-3-carbonitrile;

6-[(3S,4S)-3-{[(3R,4R,5S)-4-(4-chlorophenyl)-4-hydroxy-3,5-dimethylpiperidin-1-yl]carbonyl}-4-(5-fluoropyridin-2-yl)pyrrolidin-1-yl]pyridazine-3-carbonitrile;

6-[(3S,4S)-3-{[(3R,4R,5S)-4-(4-chlorophenyl)-4-hydroxy-3,5-dimethylpiperidin-1-yl]carbonyl}-4-(5-fluoropyridin-2-yl)pyrrolidin-1-yl]pyridazin-3(2H)-one;

6-[(3S,4S)-3-(5-cyanopyridin-2-yl)-4-{[(3R,4R,5S)-4-(4-fluorophenyl)-4-hydroxy-3,5-dimethylpiperidin-1-yl]carbonyl}pyrrolidin-1-yl]pyridazine-3-carbonitrile;

6-[(3S,4R)-3-{[(3R,4R,5S)-4-(4-fluorophenyl)-4-hydroxy-3,5-dimethylpiperidin-1-yl]carbonyl}-4-(6-methoxypyridin-3-yl)pyrrolidin-1-yl]pyridazine-3-carbonitrile;

6-[(3S,4S)-3-{[(3R,4R,5S)-4-(4-fluorophenyl)-4-hydroxy-3,5-dimethylpiperidin-1-yl]carbonyl}-4-(5-methoxypyridin-2-yl)pyrrolidin-1-yl]pyridazine-3-carbonitrile;

(3R,4R,5S)-4-(4-fluorophenyl)-1-{[(3S,4R)-1-(5-fluoropyridin-3-yl)-4-(6-methoxypyridin-3-yl)pyrrolidin-3-yl]carbonyl}-3,5-dimethylpiperidin-4-ol;

(3R,4R,5S)-1-{[(3S,4S)-4-(5-chloropyridin-2-yl)-1-pyridazin-3-ylpyrrolidin-3-yl]carbonyl}-4-(4-fluorophenyl)-3,5-dimethylpiperidin-4-ol;

6-[(3S,4S)-3-(5-chloropyridin-2-yl)-4-{[(3R,4R,5S)-4-(4-fluorophenyl)-4-hydroxy-3,5-dimethylpiperidin-1-yl]carbonyl}pyrrolidin-1-yl]pyridazin-3(2H)-one;

6-[(3S,4S)-3-(5-chloropyridin-2-yl)-4-{[(3R,4R,5S)-4-(4-fluorophenyl)-4-hydroxy-3,5-dimethylpiperidin-1-yl]carbonyl}pyrrolidin-1-yl]-2-methylpyridazin-3(2H)-one;

(3R,4R,5S)-1-{[(3S,4S)-4-(5-chloropyridin-2-yl)-1-[1,2,4]triazolo[4,3-b]pyridazin-6-ylpyrrolidin-3-yl]carbonyl}-4-(4-fluorophenyl)-3,5-dimethylpiperidin-4-ol;

(3R,4R,5S)-1-{[(3S,4S)-4-(5-chloropyridin-2-yl)-1-imidazo[1,2-b]pyridazin-6-ylpyrrolidin-3-yl]carbonyl}-4-(4-fluorophenyl)-3,5-dimethylpiperidin-4-ol;

4-[(3S,4S)-3-(5-chloropyridin-2-yl)-4-{[(3R,4R,5S)-4-(4-fluorophenyl)-4-hydroxy-3,5-dimethylpiperidin-1-yl]carbonyl}pyrrolidin-1-yl]pyrimidin-2(1H)-one;

4-[(3S,4S)-3-(5-chloropyridin-2-yl)-4-{[(3R,4R,5S)-4-(4-fluorophenyl)-4-hydroxy-3,5-dimethylpiperidin-1-yl]carbonyl}pyrrolidin-1-yl]-1-methylpyrimidin-2(1H)-one;

(3R,4R,5S)-1-{[(3S,4S)-4-(5-chloropyridin-2-yl)-1-(6-methoxypyridazin-3-yl)pyrrolidin-3-yl]carbonyl}-4-(4-fluorophenyl)-3,5-dimethylpiperidin-4-ol;

6-[(3S,4S)-3-(5-chloro-3-fluoropyridin-2-yl)-4-{[(3R,4R,5S)-4-(4-fluorophenyl)-4-hydroxy-3,5-dimethylpiperidin-1-yl]carbonyl}pyrrolidin-1-yl]pyridazine-3-carbonitrile;

6-[(3S,4S)-3-(5-chloro-3-fluoropyridin-2-yl)-4-{[(3R,4R,5S)-4-(4-fluorophenyl)-4-hydroxy-3,5-dimethylpiperidin-1-yl]carbonyl}pyrrolidin-1-yl]pyridazin-3(2H)-one;

6-[(3S,4S)-3-(5-chloro-3-fluoropyridin-2-yl)-4-{[(3R,4R, 5S)-4-(4-fluorophenyl)-4-hydroxy-3,5-dimethylpiperidin-1-yl]carbonyl}pyrrolidin-1-yl]-2-methylpyridazin-3 (2H)-one;

6-[(3S,4S)-3-(3,5-difluoropyridin-2-yl)-4-{[(3R,4R,5S)-4-(4-fluorophenyl)-4-hydroxy-3,5-dimethylpiperidin-1-yl]carbonyl}pyrrolidin-1-yl]pyridazine-3-carbonitrile;

6-[(3S,4S)-3-(3,5-difluoropyridin-2-yl)-4-{[(3R,4R,5S)-4-(4-fluorophenyl)-4-hydroxy-3,5-dimethylpiperidin-1-yl]carbonyl}pyrrolidin-1-yl]pyridazin-3(2H)-one;

6-[(3S,4S)-3-(3,5-difluoropyridin-2-yl)-4-{[(3R,4R,5S)-4-(4-fluorophenyl)-4-hydroxy-3,5-dimethylpiperidin-1-yl]carbonyl}pyrrolidin-1-yl]-2-methylpyridazin-3(2H)-one;

6-[(3S,4S)-3-{[(3R,4R,5S)-4-(4-chlorophenyl)-4-hydroxy-3,5-dimethylpiperidin-1-yl]carbonyl}-4-(5-chloropyridin-2-yl)pyrrolidin-1-yl]pyridazine-3-carbonitrile;

6-[(3S,4S)-3-(5-chloropyridin-2-yl)-4-{[(3R,4R,5S)-4-(3,4-difluorophenyl)-4-hydroxy-3,5-dimethylpiperidin-1-yl]carbonyl}pyrrolidin-1-yl]pyridazine-3-carbonitrile;

6-[(3S,4S)-3-{[(3R,4R,5S)-4-(4-chlorophenyl)-4-hydroxy-3,5-dimethylpiperidin-1-yl]carbonyl}-4-(5-chloropyridin-2-yl)pyrrolidin-1-yl]pyridazin-3(2H)-one;

6-[(3S,4S)-3-(5-chloropyridin-2-yl)-4-{[(3R,4R,5S)-4-(3,4-difluorophenyl)-4-hydroxy-3,5-dimethylpiperidin-1-yl]carbonyl}pyrrolidin-1-yl]pyridazin-3(2H)-one;

and the pharmaceutically acceptable salts, solvates (including hydrates), and prodrugs thereof.

More preferably the compound is selected from:

6-[(3S,4S)-3-(5-chloropyridin-2-yl)-4-{[(3R,4R,5S)-4-(4-fluorophenyl)-4-hydroxy-3,5-dimethylpiperidin-1-yl]carbonyl}pyrrolidin-1-yl]pyridazine-3-carbonitrile;

6-[(3S,4S)-3-(5-chloropyridin-2-yl)-4-{[(3R,4R,5S)-4-hydroxy-3,5-dimethyl-4-phenylpiperidin-1-yl]carbonyl}pyrrolidin-1-yl]pyridazine-3-carbonitrile;

6-[(3S,4S)-3-(5-chloropyridin-2-yl)-4-{[(3R,4R,5S)-4-hydroxy-3,5-dimethyl-4-phenylpiperidin-1-yl]carbonyl}pyrrolidin-1-yl]pyridazin-3(2H)-one;

6-[(3S,4S)-3-(5-chloropyridin-2-yl)-4-{[(3R,4R,5S)-4-hydroxy-3,5-dimethyl-4-phenylpiperidin-1-yl]carbonyl}pyrrolidin-1-yl]-2-methylpyridazin-3(2H)-one;

6-[(3S,4S)-3-{[(3R,4R,5S)-4-(4-chlorophenyl)-4-hydroxy-3,5-dimethylpiperidin-1-yl]carbonyl}-4-(5-chloropyridin-2-yl)pyrrolidin-1-yl]-2-methylpyridazin-3(2H)-one;

6-[(3S,4S)-3-(5-chloropyridin-2-yl)-4-{[(3R,4R,5S)-4-(5-chloropyridin-2-yl)-4-hydroxy-3,5-dimethylpiperidin-1-yl]carbonyl}pyrrolidin-1-yl]-2-methylpyridazin-3(2H)-one;

6-[(3S,4S)-3-(5-chloropyridin-2-yl)-4-{[(3R,4R,5S)-4-(3,4-difluorophenyl)-4-hydroxy-3,5-dimethylpiperidin-1-yl]carbonyl}pyrrolidin-1-yl]-2-methylpyridazin-3(2H)-one;

(3R,4R,5S)-1-{[(3S,4S)-4-(5-chloropyridin-2-yl)-1-pyridazin-3-ylpyrrolidin-3-yl]carbonyl}-4-(4-fluorophenyl)-3,5-dimethylpiperidin-4-ol;

6-[(3S,4S)-3-(5-chloropyridin-2-yl)-4-{[(3R,4R,5S)-4-(4-fluorophenyl)-4-hydroxy-3,5-dimethylpiperidin-1-yl]carbonyl}pyrrolidin-1-yl]pyridazin-3(2H)-one;

6-[(3S,4S)-3-(5-chloropyridin-2-yl)-4-{[(3R,4R,5S)-4-(4-fluorophenyl)-4-hydroxy-3,5-dimethylpiperidin-1-yl]carbonyl}pyrrolidin-1-yl]-2-methylpyridazin-3(2H)-one;

(3R,4R,5S)-1-{[(3S,4S)-4-(5-chloropyridin-2-yl)-1-[1,2,4]triazolo[4,3-b]pyridazin-6-ylpyrrolidin-3-yl]carbonyl}-4-(4-fluorophenyl)-3,5-dimethylpiperidin-4-ol;

(3R,4R,5S)-1-{[(3S,4S)-4-(5-chloropyridin-2-yl)-1-imidazo[1,2-b]pyridazin-6-ylpyrrolidin-3-yl]carbonyl}-4-(4-fluorophenyl)-3,5-dimethylpiperidin-4-ol;

4-[(3S,4S)-3-(5-chloropyridin-2-yl)-4-{[(3R,4R,5S)-4-(4-fluorophenyl)-4-hydroxy-3,5-dimethylpiperidin-1-yl]carbonyl}pyrrolidin-1-yl]pyrimidin-2(1H)-one;

4-[(3S,4S)-3-(5-chloropyridin-2-yl)-4-{[(3R,4R,5S)-4-(4-fluorophenyl)-4-hydroxy-3,5-dimethylpiperidin-1-yl]carbonyl}pyrrolidin-1-yl]-1-methylpyrimidin-2(1H)-one;

6-[(3S,4S)-3-(5-chloro-3-fluoropyridin-2-yl)-4-{[(3R,4R, 5S)-4-(4-fluorophenyl)-4-hydroxy-3,5-dimethylpiperidin-1-yl]carbonyl}pyrrolidin-1-yl]pyridazine-3-carbonitrile;

6-[(3S,4S)-3-(5-chloro-3-fluoropyridin-2-yl)-4-{[(3R,4R, 5S)-4-(4-fluorophenyl)-4-hydroxy-3,5-dimethylpiperidin-1-yl]carbonyl}pyrrolidin-1-yl]pyridazin-3(2H)-one;

6-[(3S,4S)-3-(5-chloro-3-fluoropyridin-2-yl)-4-{[(3R,4R, 5S)-4-(4-fluorophenyl)-4-hydroxy-3,5-dimethylpiperidin-1-yl]carbonyl}pyrrolidin-1-yl]-2-methylpyridazin-3 (2H)-one;

6-[(3S,4S)-3-(3,5-difluoropyridin-2-yl)-4-{[(3R,4R,5S)-4-(4-fluorophenyl)-4-hydroxy-3,5-dimethylpiperidin-1-yl]carbonyl}pyrrolidin-1-yl]pyridazine-3-carbonitrile;

6-[(3S,4S)-3-(3,5-difluoropyridin-2-yl)-4-{[(3R,4R,5S)-4-(4-fluorophenyl)-4-hydroxy-3,5-dimethylpiperidin-1-yl]carbonyl}pyrrolidin-1-yl]pyridazin-3(2H)-one;

6-[(3S,4S)-3-(3,5-difluoropyridin-2-yl)-4-{[(3R,4R,5S)-4-(4-fluorophenyl)-4-hydroxy-3,5-dimethylpiperidin-1-yl]carbonyl}pyrrolidin-1-yl]-2-methylpyridazin-3(2H)-one;

6-[(3S,4S)-3-{[(3R,4R,5S)-4-(4-chlorophenyl)-4-hydroxy-3,5-dimethylpiperidin-1-yl]carbonyl}-4-(5-chloropyridin-2-yl)pyrrolidin-1-yl]pyridazine-3-carbonitrile;

6-[(3S,4S)-3-(5-chloropyridin-2-yl)-4-{[(3R,4R,5S)-4-(3,4-difluorophenyl)-4-hydroxy-3,5-dimethylpiperidin-1-yl]carbonyl}pyrrolidin-1-yl]pyridazine-3-carbonitrile;

6-[(3S,4S)-3-{[(3R,4R,5S)-4-(4-chlorophenyl)-4-hydroxy-3,5-dimethylpiperidin-1-yl]carbonyl}-4-(5-chloropyridin-2-yl)pyrrolidin-1-yl]pyridazin-3(2H)-one;

6-[(3S,4S)-3-(5-chloropyridin-2-yl)-4-{[(3R,4R,5S)-4-(3,4-difluorophenyl)-4-hydroxy-3,5-dimethylpiperidin-1-yl]carbonyl}pyrrolidin-1-yl]pyridazin-3(2H)-one;

and the pharmaceutically acceptable salts, solvates (including hydrates), and prodrugs thereof.

Most preferably the compound is selected from:

6-[(3S,4S)-3-(5-chloropyridin-2-yl)-4-{[(3R,4R,5S)-4-(4-fluorophenyl)-4-hydroxy-3,5-dimethylpiperidin-1-yl]carbonyl}pyrrolidin-1-yl]pyridazine-3-carbonitrile;

6-[(3S,4S)-3-{[(3R,4R,5S)-4-(4-chlorophenyl)-4-hydroxy-3,5-dimethylpiperidin-1-yl]carbonyl}-4-(5-chloropyridin-2-yl)pyrrolidin-1-yl]-2-methylpyridazin-3(2H)-one;

6-[(3S,4S)-3-(5-chloropyridin-2-yl)-4-{[(3R,4R,5S)-4-(5-chloropyridin-2-yl)-4-hydroxy-3,5-dimethylpiperidin-1-yl]carbonyl}pyrrolidin-1-yl]-2-methylpyridazin-3(2H)-one;

6-[(3S,4S)-3-(5-chloropyridin-2-yl)-4-{[(3R,4R,5S)-4-(3,4-difluorophenyl)-4-hydroxy-3,5-dimethylpiperidin-1-yl]carbonyl}pyrrolidin-1-yl]-2-methylpyridazin-3(2H)-one;

6-[(3S,4S)-3-(5-chloropyridin-2-yl)-4-{[(3R,4R,5S)-4-(4-fluorophenyl)-4-hydroxy-3,5-dimethylpiperidin-1-yl]carbonyl}pyrrolidin-1-yl]pyridazin-3(2H)-one;

6-[(3S,4S)-3-(5-chloropyridin-2-yl)-4-{[(3R,4R,5S)-4-(4-fluorophenyl)-4-hydroxy-3,5-dimethylpiperidin-1-yl]carbonyl}pyrrolidin-1-yl]-2-methylpyridazin-3(2H)-one;

6-[(3S,4S)-3-{[(3R,4R,5S)-4-(4-chlorophenyl)-4-hydroxy-3,5-dimethylpiperidin-1-yl]carbonyl}-4-(5-chloropyridin-2-yl)pyrrolidin-1-yl]pyridazine-3-carbonitrile;

6-[(3S,4S)-3-(5-chloropyridin-2-yl)-4-{[(3R,4R,5S)-4-(3,4-difluorophenyl)-4-hydroxy-3,5-dimethylpiperidin-1-yl]carbonyl}pyrrolidin-1-yl]pyridazine-3-carbonitrile;

6-[(3S,4S)-3-{[(3R,4R,5S)-4-(4-chlorophenyl)-4-hydroxy-3,5-dimethylpiperidin-1-yl]carbonyl}-4-(5-chloropyridin-2-yl)pyrrolidin-1-yl]pyridazin-3(2H)-one;

6-[(3S,4S)-3-(5-chloropyridin-2-yl)-4-{[(3R,4R,5S)-4-(3,4-difluorophenyl)-4-hydroxy-3,5-dimethylpiperidin-1-yl]carbonyl}pyrrolidin-1-yl]pyridazin-3(2H)-one;

and the pharmaceutically acceptable salts, solvates (including hydrates), and prodrugs thereof.

The pharmaceutically acceptable salts of the compounds of the formula (I) include the acid addition salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Hemisalts of the acids may also be formed, for example, hemisulphate. For a review on suitable salts, see Handbook of Pharmaceutical Salts Properties, Selection, and Use by Stahl and Wermuth (Wiley-VCH, 2002).

The compounds, salts, solvates and prodrugs of the invention may exist in tautomeric, zwitterionic, polymorphic, crystalline, liquid crystalline, etc. forms. All such forms are included within the scope of the invention. As an example to illustrate a tautomeric relationship, the compound where for example the "Het" group is as shown below, both "keto" and "enol" tautomers below are included within the scope of "Het" for the compounds of formula (I):

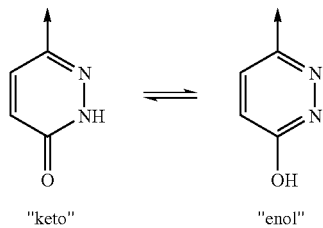

"keto"    "enol"

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt.

Also included within the scope of the invention are isotopically labelled compounds of formula (I), for example where $^2$H, $^3$H, $^{13}$C, $^{15}$N, $^{18}$O or other isotopes, are incorporated, which may be made by suitable variation of the synthetic methods described herein using methods and reagents known in the art or routine modification thereof.

As indicated, so-called 'prodrugs' of the compounds of formula (I) are within the scope of the invention. Thus certain derivatives of compounds of formula (I), which may have little or no pharmacological activity themselves, can, when administered into or onto the body, be converted into compounds of formula (I) having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T Higuchi and W Stella) and *Bioreversible Carriers in Drug Design*, Pergamon Press, 1987 (Ed. E B Roche, American Pharmaceutical Association).

Certain compounds of formula (I) may also themselves act as prodrugs of other compounds of formula (I).

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2 to 20%, and may contain from 0 to 5% by volume of an alkylamine. Concentration of the eluate affords the enriched mixture. The absolute composition of the mobile phase will be dependant upon the chiral stationary phase (asymmetric resin) selected.

The routes below, including those mentioned in the Examples and Preparations, illustrate methods of synthesising compounds of formula (I). The skilled person will appreciate that the compounds of the invention, and intermediates thereto, could be made by methods other than those specifically described herein, for example by adaptation of the methods described herein, for example by methods known in the art. Suitable guides to synthesis, functional group interconversions, use of protecting groups, etc., are for example: "Comprehensive Organic Transformations" by R C Larock, VCH Publishers Inc. (1989); Advanced Organic Chemistry" by J. March, Wiley Interscience (1985); "Designing Organic Synthesis" by S Warren, Wiley Interscience (1978); "Organic Synthesis—The Disconnection Approach" by S Warren, Wiley Interscience (1982); "Guidebook to Organic Synthesis" by R K Mackie and D M Smith, Longman (1982); "Protective Groups in Organic Synthesis" by T W Greene and P G M Wuts, John Wiley and Sons, Inc. (1999); and "Protecting Groups" by P J, Kocienski, Georg Thieme Verlag (1994); and any updated versions of said standard works.

In the general synthetic methods below, unless otherwise specified, the substituents R, $R^1$, $R^2$, X, Y and Het are as defined above with reference to the compounds of formula (I) above.

The routes below illustrate methods of synthesising compounds of formula (I). The skilled person will appreciate that other methods may be equally as viable.

Scheme 1 illustrates the preparation of compounds of formula (I) via peptide coupling of intermediates (II) and (III), if necessary adding a suitable base and/or additive (such as 1-hydroxybenzotriazole hydrate or 4-dimethylaminopyridine).

Scheme 1

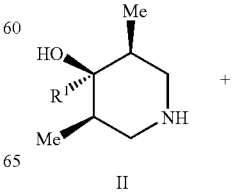

II

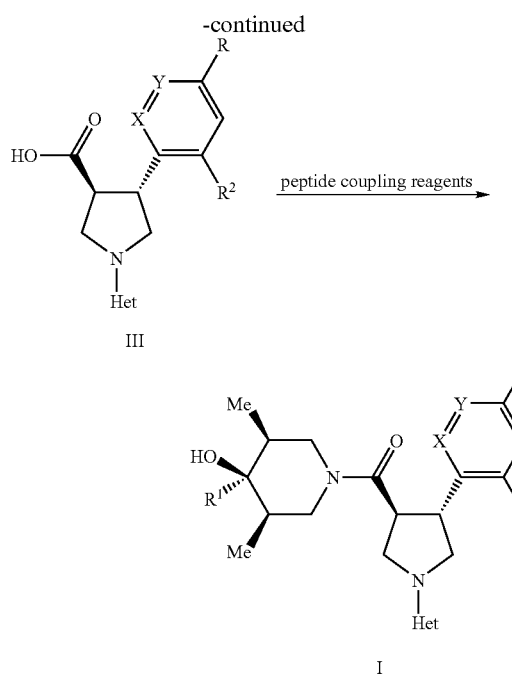

Alternative conditions employed involve stirring a solution of the piperidine of general formula (II) and the acid of general formula (III) together with 1-(3-dimethylaminopropyl)-3-ethyl-carbodiimide hydrochloride (EDCI), triethylamine or N-methylmorpholine and 1-hydroxybenzotriazole hydrate (HOBt) in dimethylformamide (DMF), tetrahydrofuran (THF), dichloromethane (DCM) or ethyl acetate (EtOAc) at room temperature. A further alternative suitable procedure is to stir a solution of the intermediate compounds of general formula (II) and general formula (III) together with O-benzotriazol-1-yl-N,N,N',N'-tetramethyluronium hexafluorophosphate (HBTU) or 1-propylphosphonic acid cyclic anhydride in $CH_2Cl_2$ or EtOAc. Any suitable inert solvent may be used in place of those mentioned above, wherein inert solvent means a solvent which does not contain a carboxylic acid or primary or secondary amine. At least one equivalent of each of the coupling reagents should be used and an excess of either one or both may be used if desired.

According to a further embodiment the present invention provides novel intermediate compounds of general formula (III).

Scheme 2 illustrates an alternative route for the preparation of compounds of general formula (I), having a range of Het groups, via utility of a protecting group strategy.

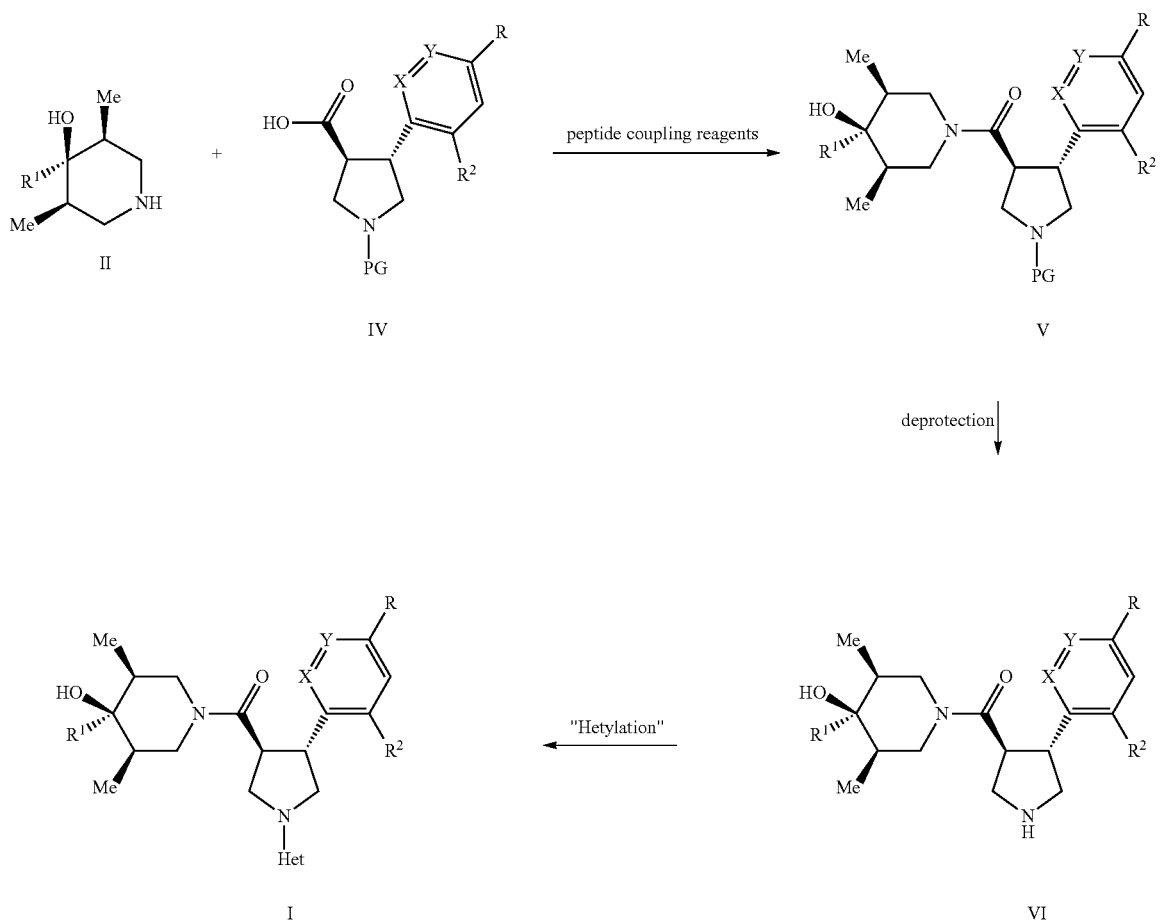

PG is a suitable nitrogen-protecting group.

Novel compounds of formulae (IV), (V) and (VI) are further embodiments of the invention.

In scheme 2 the amine intermediates of general formula (II) and protected pyrrolidine acid intermediates of general formula (IV) are coupled using standard peptide coupling methods as previously described in scheme 1 to provide a coupled and protected intermediate of general formula (V) from which the nitrogen protecting group can be removed using standard de-protection strategies to furnish a compound of general formula (VI). Any suitable nitrogen protecting groups may be used (as described in "Protecting Groups in Organic Synthesis" 3$^{rd}$ Edition T. W. Greene and P. G. Wuts, Wiley-Interscience, 1999). Common nitrogen protecting groups (PG) suitable for use herein include tert-butoxycarbonyl (t-Boc), which is readily removed by treatment with an acid such as trifluoroacetic acid or hydrogen chloride in an organic solvent such as dichloromethane or 1,4-dioxane, and benzyl, which is readily removed by hydrogenation in the presence of a suitable catalyst or by treatment with 1-chloroethyl chloroformate.

The "Het" group (where "Het" is a heteroaryl group) may be introduced by displacement of a suitable leaving group, for example from a heteroaromatic precursor of formula "Het-L" where L is a suitable leaving group. Suitable leaving groups include halogens. In certain cases transition metal catalysis (e.g. palladium, copper), optionally in combination with a phosphine ligand such as 1,1'-binaphthalene-2,2'-diylbis-diphenylphosphine, may be required to achieve the required coupling products.

Alternatively, compounds of general formula (I) having particular Het groups may be converted into other compounds of general formula (I) having different Het groups. For example:

i) Compounds of formula (Ia), where Het contains a suitable leaving group L, such as methoxy or chlorine, as shown in scheme 3, can be converted into compounds of formula (Ib), as shown in scheme 3, by hydrolysis under either acidic or basic conditions. Acidic conditions are preferred, and particularly preferred is treatment of compounds of formula (Ia) with acetic acid at reflux temperature. Alternatively, a compound of formula (Ia), where L is chloro, can be reacted with an alkoxide of formula Z—O$^-$, where Z is a suitable oxygen protecting group, to give an intermediate of formula (Ia), where L is OZ. Subsequent deprotection then provides the compounds of formula (Ib). For example, when Z=benzyl, it can readily be removed by hydrogenation in the presence of a suitable catalyst

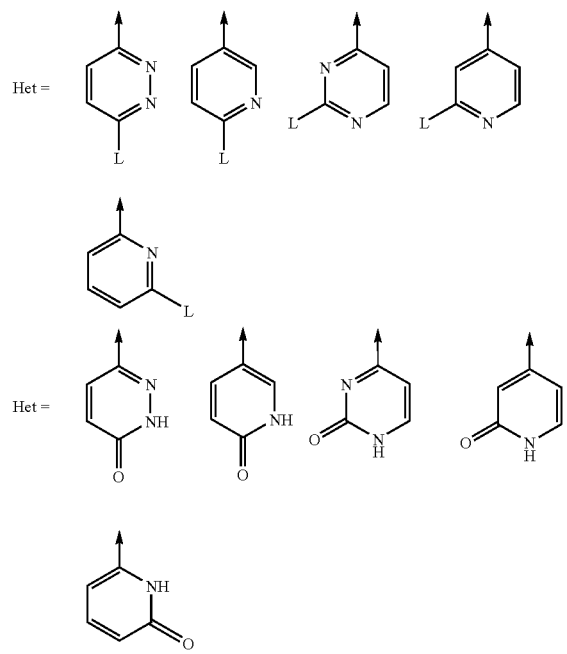

ii) Compounds of formula Ic, where Het is as shown in scheme 4 and R$^3$ is H, can be converted into compounds of formula Id, where R$^3$ is methyl or ethyl, as shown in scheme 4, by treatment with a base and an alkylating agent in an appropriate solvent. Suitable bases include sodium hydride, lithium diisopropylamide and sodium hexamethyldisilazide, suitable alkylating agents include methyl iodide, methyl tosylate, dimethyl sulfate and ethyl iodide and suitable solvents include tetrahydrofuran, dimethylformamide and N-methyl-2-pyrrolidinone. An optional additive, such as a lithium salt, lithium bromide for example, may also be present in the reaction mixture.

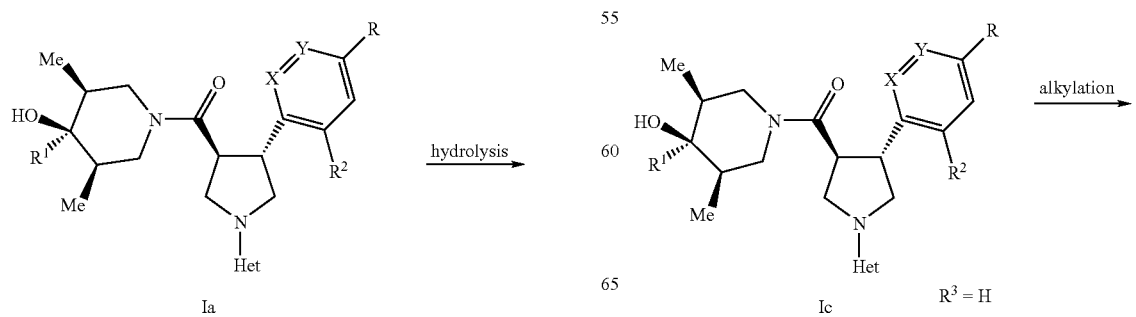

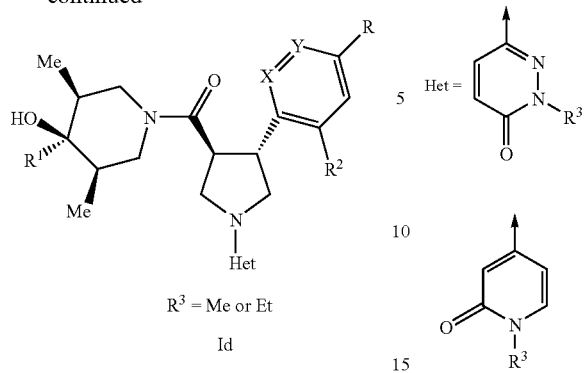
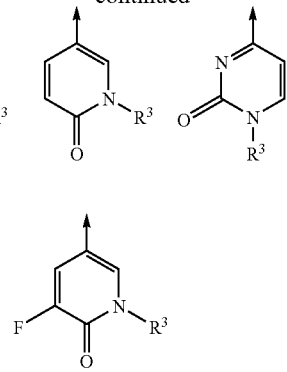
Scheme 5 illustrates the route for preparation of the pyrrolidine acid intermediates of general formula (IV) from unsaturated intermediates of general formula (VII).
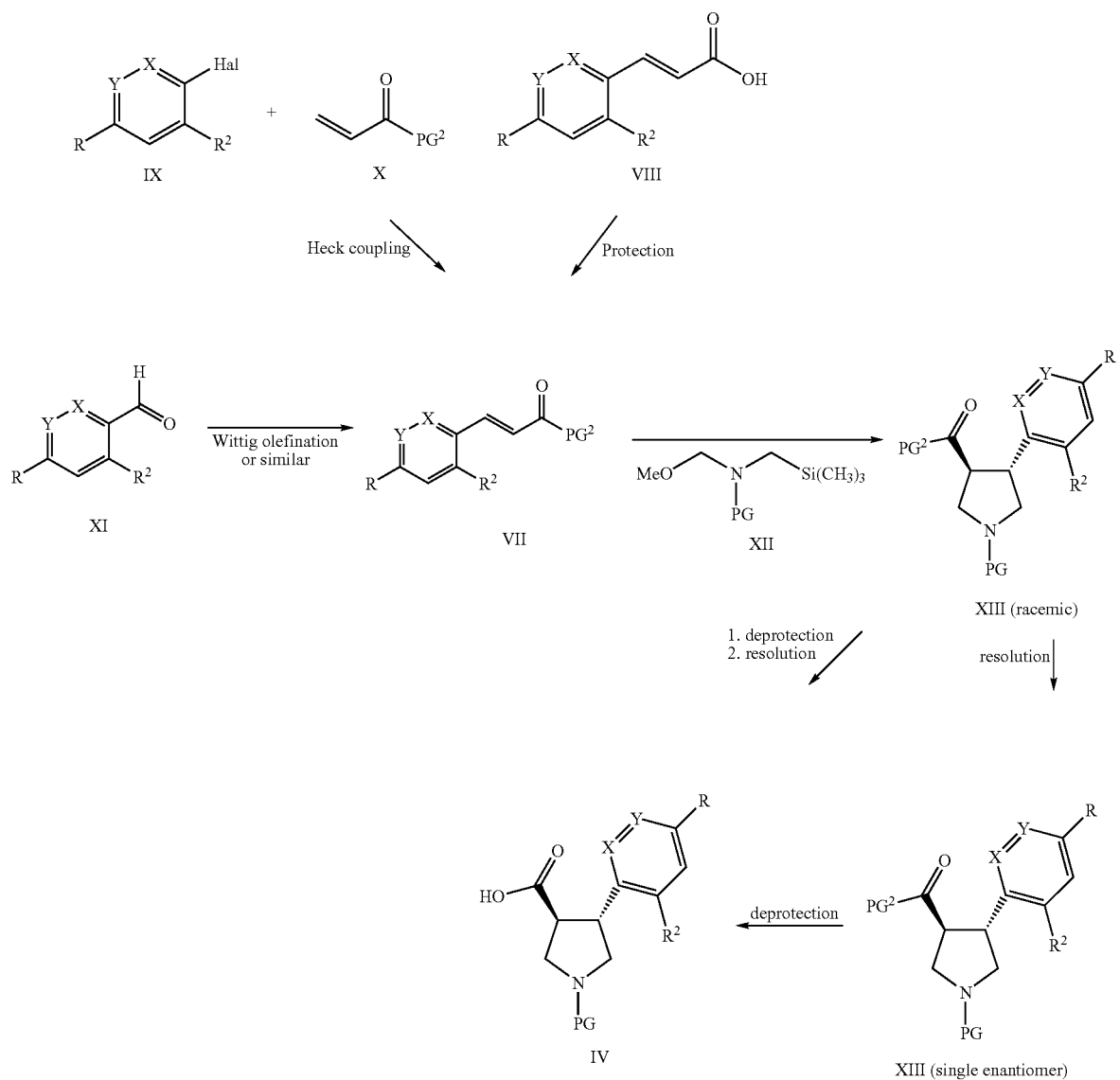

PG is a suitable nitrogen protecting group. $PG^2$ is a suitable carboxylic acid protecting group. Compounds of formulae (VIII), (IX), (X), (XI) and (XII) are either commercially available or will be well-known to those skilled in the art with reference to literature precedents and/or the preparations herein.

Compounds of general formula (VII) can be made predominantly as the desired trans-isomer by Wittig or similar olefination of an aldehyde intermediate of general formula (XI) with a suitable ylid e.g. methyl (triphenylphosphoranylidene)acetate, or a phosphonate anion e.g. derived from deprotonation of trimethylphosphonoacetate.

Many alternative methods exists in the literature for the production of unsaturated intermediates of general formula (VII), including protection of a precursor cinnamic acid derivative (VIII) using standard methods, or Heck reaction of an aromatic halide (IX) with a suitable acrylate derivative (X), such as t-butyl acrylate, in the presence of a palladium catalyst and a suitable base, such as triethylamine.

The resulting E-olefin intermediate of general formula (VII) will undergo a [3+2]-azomethine ylid cycloaddition by reaction with an ylid precursor of general formula (XII), to provide a pyrrolidine with almost exclusively the trans-stereochemistry. This reaction requires an inert solvent such as dichloromethane or toluene or tetrahydrofuran and activation by one or more of: (1) an acid catalyst, such as TFA; (2) a desilylating agent such as silver fluoride; (3) heating.

The compound of general formula (XIII) obtained from the cycloaddition reaction is a racemate and may require resolution into its constituent enantiomers, which can be achieved by preparative HPLC using a chiral stationary phase. Alternatively the acid intermediate of general formula (IV) can be resolved by standard methods (e.g. formation of diastereomeric derivatives by reaction with an enantiomerically pure reagent, separation of the resulting diastereomers by physical methods and cleaving to acid (IV).

Intermediate compounds of general formula (XIII) can be converted into compounds of general formula (IV) by deprotection of the protecting group $PG^2$. Many methods are available to achieve this transformation (see Advanced Organic Chemistry: Reactions, Mechanisms, and Structure, Fourth Edition. March, Jerry, 1992, pp 378-383 published by Wiley, New York, N.Y. USA). In particular, for base labile protecting groups, treatment of a compound of general formula (XIII) with an aqueous alkali metal hydroxide solution, such as lithium hydroxide, sodium hydroxide or potassium hydroxide in a suitable organic solvent will provide the corresponding compounds of general formula (IV). Preferably water-miscible organic co-solvents (such as 1,4-dioxane or tetrahydrofuran) are also utilised in such reactions. If required, the reaction may be heated to assist the hydrolysis. Certain protecting groups are more conveniently hydrolysed in acidic conditions e.g. tert-butyl or benzhydryl esters. Such esters can be cleaved by treatment with anhydrous acids such as trifluoroacetic acid or hydrogen chloride in an inert organic solvent such as dichloromethane.

Novel compounds of formulae (XIII) are further embodiments of the invention.

Scheme 6 illustrates an alternative route for the preparation of a single enantiomer of the pyrrolidine acid intermediate of general formula (IV) from unsaturated intermediates of general formula (VII), using an oxazolidinone as a chiral auxiliary. The acid of formula (VIII) may be obtained by deprotection of (VII) and then converted to a mixed anhydride and coupled to an oxazolidinone (where $R^4$ is preferably phenyl, tertiary butyl, or iso-propyl) to provide an intermediate of formula (XIV). Alternatively, the reaction of a compound of formula (VII) (e.g. when $PG^2$=OCOt-Bu) with the lithium salt of an oxazolidinone, in a suitable solvent (e.g. THF), may also provide a compound of formula (XIV).

The compound of formula (XIV) will undergo an [3+2]-azomethine ylide cycloaddition by reaction with the compound of general formula (XII), to provide diastereomers (XV) and (XVI) which can be separated by chromatography or crystallisation and hydrolysed to give a pyrrolidine of formula (IV). Alternatively, a compound of general formula (XVI) can be converted to a compound of general formula (XIII), for example by treatment with sodium methoxide in dimethyl carbonate (when $PG^2$=OMe).

Scheme 6

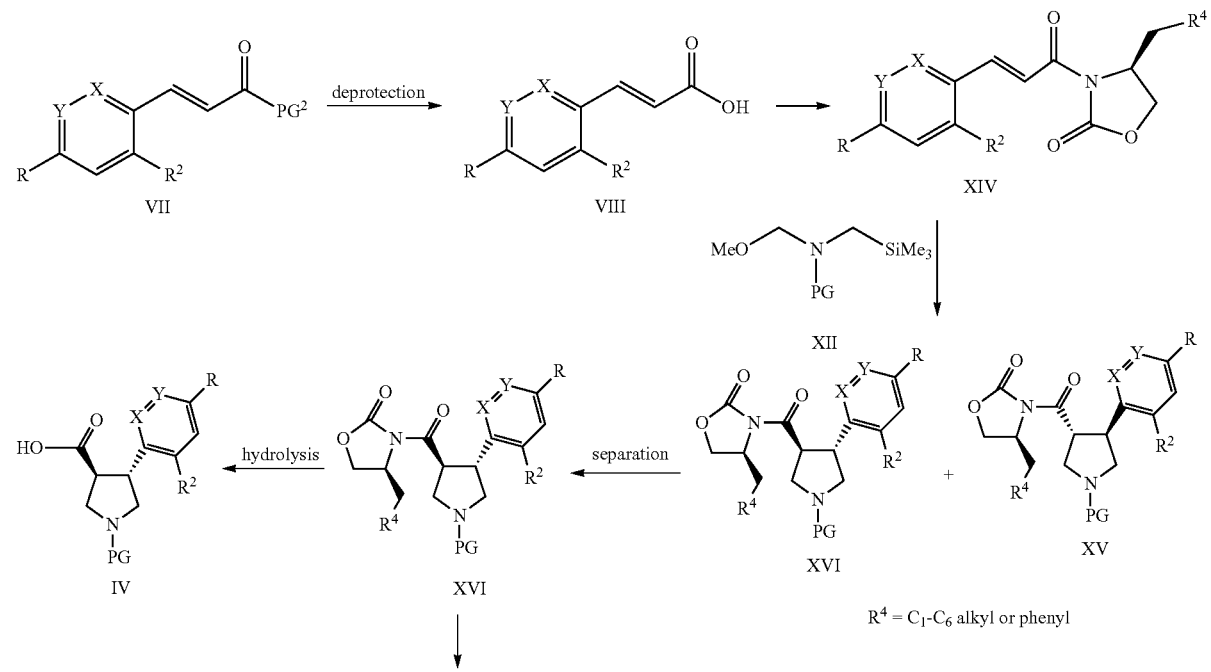

$R^4$ = $C_1$-$C_6$ alkyl or phenyl

-continued

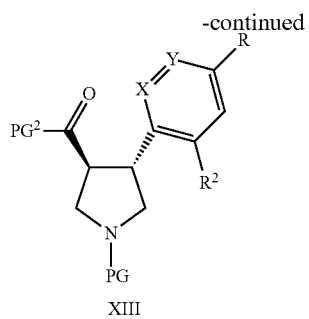

XIII

PG is selected from suitable nitrogen protecting groups. PG² is selected from suitable carboxylic acid protecting groups, and different groups may be employed with respect to compounds (VII) and (XIII).

Novel compounds of formulae (XVI) are further embodiments of the invention.

Scheme 7 illustrates a route for preparation of the pyrrolidine acid intermediates of general formula (III) from intermediates of general formula (XIII). Once the protecting group PG is removed, using any suitable conventional techniques, Het groups may be introduced by suitable methods described above re Scheme 2. Removal of the acid protecting group PG², as described in scheme 4, then provides the acid of general formula (III).

containing a suitable nitrogen protecting group (PG) to furnish intermediates of general formula (XX). The stereochemistry of the addition is favoured such that the hydroxyl group in the product is cis to the two methyl groups. Controlled addition to carbonyl systems such as this have been described in the literature (e.g. Journal of Medicinal Chemistry (1964), 7(6), pp 726-8). Such nucleophilic addition is generally carried out at low temperature in an anhydrous ethereal or other non-polar solvent, using Grignard, organolithium or other suitable organometallic reagent. These organometallic reagents can be made by halogen-metal exchange using a suitable halide precursor, $R^1$—Br or $R^1$—I and n-butyl lithium or t-butyl lithium. Suitable protecting groups include benzyl, which may be removed by hydrogenation, or Boc, Scheme 7

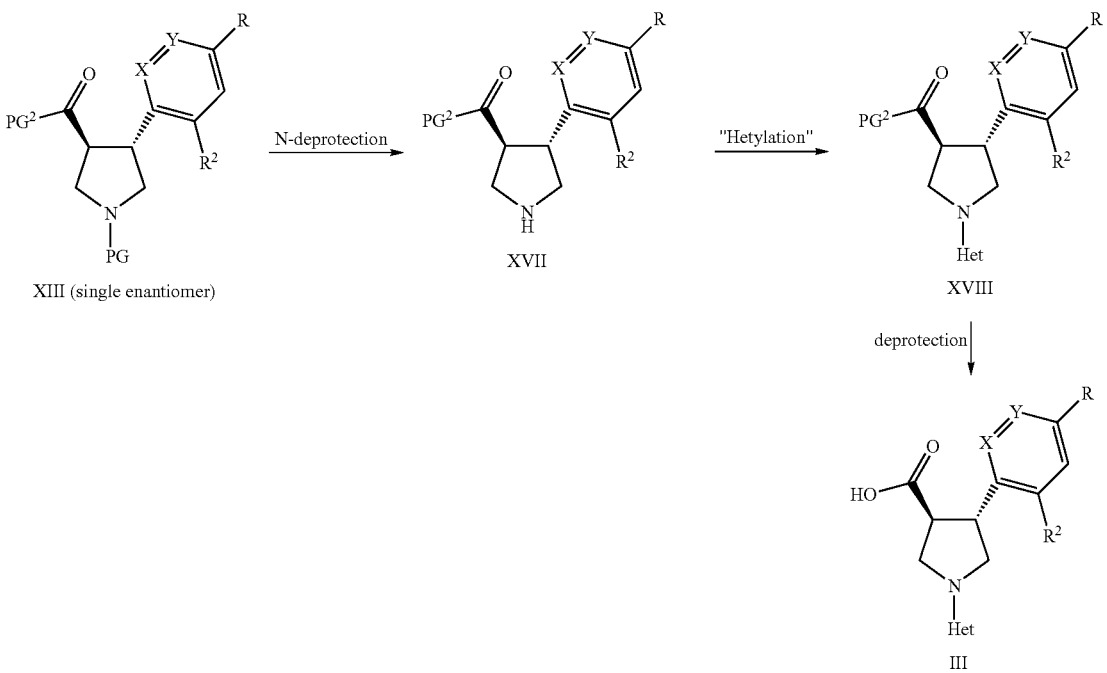

PG is selected from suitable nitrogen protecting groups. PG² is selected from suitable carboxylic acid protecting groups.

Novel compounds of formulae (XVII) and (XVIII) are further embodiments of the invention.

As illustrated in Scheme 8, piperidine intermediates of general formula (II) can be prepared by addition of organometallic nucleophiles to ketones of general formula (XIX)

which may be removed by treatment with an acid such as TFA, or para-methoxybenzyl (PMB) which may be removed by treatment with DDQ, CAN or 1-chloroethyl chloroformate, to afford the desired piperidine intermediates of general formula (II). With certain protecting groups and under certain conditions the protecting group may be labile to treatment with the organometallic reagent, and so both transformations may be accomplished in one step. e.g. when PG=Boc the protecting group may sometimes be cleaved when intermediates of formula (XIX) are treated with an organometallic reagent.

Scheme 8

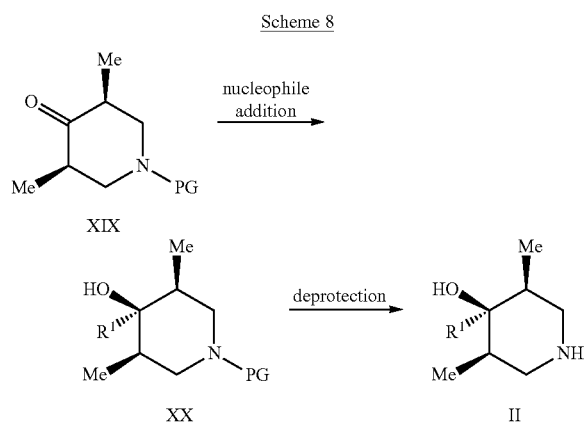

PG is selected from suitable nitrogen protecting groups.

The skilled man will appreciate that, in addition to protecting nitrogen or acid groups, as discussed hereinbefore, at various times during the synthesis of the compounds of formula I, it may be necessary to protect further groups, such as for example, hydroxy groups with a suitable protecting group, then remove the protecting group. Methods for deprotection of any particular group will depend on the protecting group. For examples of protection/deprotection methodology see "Protective groups in Organic synthesis", T W Greene and P G M Wutz. For example, where a hydroxy group is protected as a methyl ether, deprotection conditions could for example comprise refluxing in 48% aqueous HBr, or by stirring with borane tribromide in dichloromethane. Alternatively where a hydroxy group is protected as a benzyl ether, deprotection conditions could for example comprise hydrogenation with a palladium catalyst under a hydrogen atmosphere.

All of the above reactions and the preparations of novel starting materials used in the preceding methods are conventional and appropriate reaction conditions for their performance as well as procedures for isolating the desired products will be well-known to those skilled in the art with reference to literature precedents and the Examples and Preparations herein.

A pharmaceutically acceptable salt of a compound of the formula (I) may be readily prepared by mixing together solutions of a compound of the formula (I) and the desired acid as appropriate. The salt may precipitate from solution and be collected by filtration or may be recovered by evaporation of the solvent.

Pharmaceutically acceptable salts of compounds of formula (I) may be prepared by one or more of three methods:
(i) by reacting the compound of formula (I) with the desired acid;
(ii) by removing an acid- or base-labile protecting group from a suitable precursor of the compound of formula (I) or by ring-opening a suitable cyclic precursor, for example, a lactone or lactam, using the desired acid; or
(iii) by converting one salt of the compound of formula (I) to another by reaction with an appropriate acid or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of formula (I) of the present invention have utility as MCR4 agonists in the treatment of various disease states. Preferably said MCR4 agonists exhibit a functional potency at the MC4 receptor expressed as an $EC_{50}$, lower than about 1000 nM, more preferably lower than 500 nM, yet more preferably lower than about 100 nM and more preferably still lower than about 50 nM wherein said $EC_{50}$ measurement of MCR4 functional potency can be carried out using Protocol E as described in International Patent Application publication number WO 2005/077935. Using this assay, compounds according to the present invention exhibit a functional potency at the MC4 receptor expressed as an $EC_{50}$ lower than 1000 nM.

Preferred compounds herein exhibit functional potency at the MCR4 receptor as defined herein before and are selective for MCR4 over MCR1. Preferably said MCR4 agonists have a selectivity for MCR4 over MCR1 wherein said MCR4 receptor agonists are at least about 10-times, preferably at least about 20-times, more preferably at least about 30-times, even more preferably at least about 100-times, more preferably still at least about 300-times, even more preferably still at least about 500-times and especially at least about 1000-times more functionally selective for a MCR4 receptor as compared with the MCR1 receptor wherein said relative selectivity assessments are based on the measurement of MCR1 and MCR4 functional potencies which can be carried out using the assays as described herein.

Preferably said MCR4 agonists have a selectivity for MCR4 over MCR3 wherein said MCR4 receptor agonists are at least about 10-times, preferably at least about 30-times, more preferably at least about 100-times, more preferably still at least about 300-times, even more preferably still at least about 500-times and especially at least about 1000-times more functionally selective for a MCR4 receptor as compared with the MCR3 receptor wherein said relative selectivity assessments are based on the measurement of MCR3 and MCR4 functional potencies which can be carried out using the assays as described herein.

Preferred compounds herein exhibit functional potency at the MCR4 receptor as defined herein before and are selective for MCR4 over MCR5. Preferably said MCR4 agonists have a selectivity for MCR4 over MCR5 wherein said MCR4 receptor agonists are at least about 10-times, preferably at least about 30-times, more preferably at least about 100-times, more preferably still at least about 300-times, even more preferably still at least about 500-times and especially about 1000-times more functionally selective for a MCR4 receptor as compared with the MCR5 receptor wherein said relative selectivity assessments are based on the measurement of MCR5 and MCR4 functional potencies which can be carried out using the assays as described herein.

Preferably said MCR4 agonists have a selectivity for MCR4 over MCR1 and MCR3 wherein said MCR4 receptors agonists are at least about 10-times, preferably at least about 30-times, more preferably at least about 100-times, more preferably still at least about 300-times, even more preferably still at least about 1000-times more functionally selective for a MCR4 receptor as compared with the MCR1 and MCR3 receptors.

Preferred compounds herein exhibit functional potency at the MCR4 receptor as defined herein before and are selective for MCR4 over MCR1 and MCR5. Preferably said MCR4 agonists have a selectivity for MCR4 over MCR1 and MCR5 wherein said MCR4 receptor agonists are at least about 10-times, preferably at least about 30-times, more preferably at least about 100-times, more preferably still at least about 300-times, even more preferably still at least about 500-times and especially at least about 1000-times more functionally selective for a MCR4 receptor as compared with the MCR1 and MCR5 receptors.

Preferably said MCR4 agonists have a selectivity for MCR4 over MCR3 and MCR5 wherein said MCR4 receptor agonists are at least about 10-times, preferably at least about 30-times, more preferably at least about 100-times, more preferably still at least about 300-times, most preferably at least about 1000-times more functionally selective for a MCR4 receptor as compared with the MCR3 and MCR5 receptors.

Combination Therapy

The compounds of formula (I) or their salts, solvates or prodrugs, of the present invention may be usefully delivered in combination with an auxiliary effective active agent for the treatment of conditions of interest, such as sexual dysfunction, lower urinary tract disorders, obesity and/or diabetes. Further, the compounds of formula (I) or their salts, solvates or prodrugs, of the present invention may in some cases be usefully delivered in combination with an auxiliary effective active agent for the reduction of emesis. Some suitable auxiliary active agents which may be of use in combinations of the present invention include:

1) Compounds which modulate the action of natriuretic factors in particular atrial naturetic factor (also known as atrial naturetic peptide), B type and C type natriuretic factors such as inhibitors or neutral endopeptidase and in particular the compounds described and claimed in WO 02/02513, WO 02/03995, WO 02/079143 and EP-A-1258474, and especially the compound of Example 22 of WO 02/079143 (2S)-2{[1-{3-4(-chlorophenyl)propyl]amino}carbonyl)-cyclopentyl]methyl}-4-methoxybutanoic acid;
2) Compounds which inhibit angiotensin-converting enzyme such as enalapril, and combined inhibitors of angiotensin-converting enzyme and neutral endopeptidase such as omapatrilat;
3) Substrates for NO-synthase, such as L-arginine;
4) Cholesterol lowering agents such as statins (e.g. atorvastatin/Lipitor™) and fibrates;
5) Estrogen receptor modulators and/or estrogen agonists and/or estrogen antagonists, preferably raloxifene or lasofoxifene ((−)-cis-6-phenyl-5-[4-(2-pyrrolidin-1-yl-ethoxy)-phenyl]-5,6,7,8-tetrahydronaphthalene-2-ol, and pharmaceutically acceptable salts thereof the preparation of which is detailed in WO 96/21656);
6) A PDE inhibitor, more particularly a PDE 2, 3, 4, 5, 7 or 8 inhibitor, preferably PDE2 or PDE5 inhibitor and most preferably a PDE5 inhibitor (see hereinafter), said inhibitors preferably having an $IC_{50}$ against the respective enzyme of less than 100 nM (with the proviso that PDE 3 and 4 inhibitors are only administered topically or by injection to the penis for treatment of Male Erectile Dysfunction);
7) Vasoactive intestinal protein (VIP), VIP mimetic, VIP analogue, more particularly mediated by one or more of the VIP receptor subtypes VPAC1, VPAC or PACAP (pituitory adenylate cyclase activating peptide), one or more of a VIP receptor agonist or a VIP analogue (e.g. Ro-125-1553) or a VIP fragment, one or more of a α-adrenoceptor antagonist with VIP combination (e.g. Invicorp, Aviptadil);
8) A serotonin receptor agonist, antagonist or modulator, more particularly agonists, antagonists or modulators for 5HT1A (including VML 670 [WO02/074288] and flibanserin [US2003/0104980]), 5HT2A, 5HT2C, 5HT3 and/or 5HT6 receptors, including those described in WO-09902159, WO-00002550 and/or WO-00028993;
9) A testosterone replacement agent (including dehydroandrostendione), testosterone (e.g. Tostrelle™, LibiGel™), dihydrotestosterone or a testosterone implant;
10) Selective androgen receptor modulators e.g. LGD-2226;
11) Estrogen, estrogen and medroxyprogesterone or medroxyprogesterone acetate (MPA) (i.e. as a combination), or estrogen and methyl testosterone hormone replacement therapy agent (e.g. HRT especially Premarin, Cenestin, Oestrofeminal, Equin, Estrace, Estrofem, Elleste Solo, Estring, Eastraderm TTS, Eastraderm Matrix, Dermestril, Premphase, Preempro, Prempak, Premique, Estratest, Estratest HS, Tibolone);
12) A modulator of transporters for noradrenaline, dopamine and/or serotonin, such as bupropion, GW-320659;
13) An agonist or modulator for oxytocin/vasopressin receptors, preferably a selective oxytocin agonist or modulator;
14) An agonist or modulator for dopamine receptors, preferably a D3 or D4 selective agonist or modulator e.g. apomorphine; and
15) An antiemetic agent, for example a 5-$HT_3$ antagonist or a neurokinin-1 (NK-1) antagonist.

Suitable 5-$HT_3$ antagonists include, but are not limited to, granisetron, ondansetron, tropisetron, ramosetron, palonsetron, indisetron, dolasetron, alosetron and azasetron. Suitable NK-1 antagonists include, but are not limited to, aprepitant, casopitant, ezlopitant, cilapitant, netupitant, vestipitant, vofopitant and 2-(R)-(1-(R)-3,5-bis(trifluoromethyl)phenyl) ethoxy-4-(5-(dimethylamino)methyl-1,2,3-triazol-4-yl)methyl-3-(S)-(4-fluorophenyl)morpholine. See for example International Patent Application publication number WO2006/049933.

With particular reference to the use of the compounds of the invention for the treatment of lower urinary tract dysfunction, combinations with other agents may include but are not limited to Muscarinic acetylcholine receptor antagonist such as tolterodine;
Alpha adrenergic receptor antagonist, in particular an alpha1 adrenergic receptor antagonist or an alpha2 adrenergic receptor antagonist;
Alpha adrenergic receptor agonist or partial agonist, in particular an alpha1 adrenergic receptor agonist or partial agonist, or an alpha2 adrenergic receptor agonist or partial agonist;
5HT2C agonist (see WO 2004/096196);
Serotonin and Noradrenalin reuptake inhibitor (SNRI);
Noradrenalin reuptake inhibitor (NRI) such as reboxetine, either in its racemic or (S,S)-enantiomeric form;
Vanilloid receptor (VR) antagonist, such as capsaicin;
alpha2delta ligand, such as gabapentin or pregabalin;
Beta3 adrenergic receptor agonist;
5HT1 a receptor antagonist or 5HT1 a receptor inverse agonist;
Prostanoid receptor antagonist, e.g. EP1 receptor antagonist.

With regard to the use of the compounds of formula (I) in the treatment of obesity and related disorders, the compounds may also be useful in conjunction with other anti-obesity agents. Suitable anti-obesity agents include cannabinoid 1 (CB-1) receptor antagonists (such as rimonabant), apolipoprotein-B secretion/microsomal triglyceride transfer protein (apo-B/MTP) inhibitors (in particular, gut-selective MTP inhibitors, such as edipatapide or dirlotapide), 11β-hydroxy steroid dehydrogenase-1 (11β-HSD type 1) inhibitors, peptide $YY_{3-36}$ and analogs thereof, cholecystokinin-A (CCK-A)

agonists, monoamine reuptake inhibitors (such as sibutramine), sympathomimetic agents, $\beta_3$ adrenergic receptor agonists, dopamine receptor agonists (such as bromocriptine), melanocyte-stimulating hormone receptor analogs, 5HT2c receptor agonists, melanin concentrating hormone antagonists, leptin (the OB protein), leptin analogs, leptin receptor agonists, galanin antagonists, lipase inhibitors (such as tetrahydrolipstatin, i.e. orlistat), anorectic agents (such as a bombesin agonist), Neuropeptide-Y receptor antagonists (in particular, NPY-5 receptor antagonists), thyromimetic agents, dehydroepiandrosterone or an analog thereof, glucocorticoid receptor agonists or antagonists, orexin receptor antagonists, glucagon-like peptide-1 receptor agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, ghrelin receptor antagonists, histamine 3 receptor antagonists or inverse agonists, neuromedin U receptor agonists and the like. Other anti-obesity agents, including the preferred agents set forth hereinbelow, are well known, or will be readily apparent in light of the instant disclosure, to one of ordinary skill in the art. The compounds of the present invention may also be administered in combination with a naturally occurring compound that acts to lower plasma cholesterol levels. Such naturally occurring compounds are commonly called nutraceuticals and include, for example, garlic extract, Hoodia plant extracts, and niacin. Especially preferred are anti-obesity agents selected from the group consisting of CB-1 antagonists, gut-selective MTP inhibitors, orlistat, sibutramine, bromocriptine, ephedrine, leptin, peptide $YY_{3-36}$ and analogs thereof, and pseudoephedrine. Preferably, compounds of the present invention and combination therapies for the treatment of obesity and related conditions are administered in conjunction with exercise and a sensible diet. Preferred CB-1 antagonists include Rimonabant (SR141716A also known under the tradename Acomplia™ available from Sanofi-Synthelabo) described in U.S. Pat. No. 5,624,941; and compounds described in U.S. Pat. Nos. 5,747,524, 6,432,984 and 6,518,264; U.S. Patent Publication Nos. US2004/0092520, US2004/0157839, US2004/0214855, and US2004/0214838; U.S. patent application Ser. No. 10/971,599 filed on Oct. 22, 2004; and PCT Patent Publication Nos. WO 02/076949, WO 03/075660, WO04/048317, WO04/013120, and WO 04/012671. Preferred gut-slective MTP inhibitors include dirlotapide described in U.S. Pat. No. 6,720,351; 4-(4-(4-(4-((2-((4-methyl-4H-1,2,4-triazol-3-ylthio)methyl)-2-(4-chlorophenyl)-1,3-dioxolan-4-yl)methoxy)phenyl)piperazin-1-yl)phenyl)-2-sec-butyl-2H-1,2,4-triazol-3(4H)-one (R103757) described in U.S. Pat. Nos. 5,521,186 and 5,929,075; and implitapide (BAY 13-9952) described in U.S. Pat. No. 6,265,431. Other representative anti-obesity agents for use in the combinations, pharmaceutical compositions, and methods of the invention can be prepared using methods known to one of ordinary skill in the art, for example; sibutramine can be prepared as described in U.S. Pat. No. 4,929,629; bromocriptine can be prepared as described in U.S. Pat. Nos. 3,752,814 and 3,752,888; orlistat can be prepared as described in U.S. Pat. Nos. 5,274,143; 5,420,305; 5,540,917; and 5,643,874; and $PYY_{3-36}$ (including analogs) can be prepared as described in US Publication No. 2002/0141985 and WO 03/027637.

One preferred group herein are combinations of the compounds of the present invention and one or more additional therapeutic agents selected from: PDE5 inhibitors; NEP inhibitors; D3 or D4 selective agonists or modulators; estrogen receptor modulators and/or estrogen agonists and/or estrogen antagonists; testosterone replacement agents, testosterone or a testosterone implant; estrogen, estrogen and medroxyprogesterone or medroxyprogesterone acetate (MPA), or estrogen and methyl testosterone hormone replacement therapy agent.

Preferred combinations for the treatment of MED are combinations of the compounds of the present invention and one or more PDE5 inhibitors and/or NEP inhibitors.

Preferred combinations for the treatment of FSD are combinations of the compounds of the present invention and PDE5 inhibitors, and/or NEP inhibitors, and/or D3 or D4 selective agonists or modulators, and/or estrogen receptor modulators, estrogen agonists, estrogen antagonists, and/or testosterone replacement agents, testosterone, testosterone implant, and/or estrogen, estrogen and medroxyprogesterone or medroxyprogesterone acetate (MPA), estrogen and methyl testosterone hormone replacement therapy agent.

Particularly preferred PDE5 inhibitors for such combined products for the treatment of MED or FSD are 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil, particularly present as the citrate salt); (6R,12aR)-2,3,6,7,12,12a-hexahydro-2-methyl-6-(3,4-methylenedioxyphenyl)-pyrazino[2',1':6,1]pyrido[3,4-b]indole-1,4-dione (IC-351 or tadalafil); 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil); 5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one; 5-(5-Acetyl-2-propoxy-3-pyridinyl)-3-ethyl-2-(1-isopropyl-3-azetidinyl)-2,6-dihydro-7H-pyrazolo[4,3-d]pyrimidin-7-one; 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one; 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide (TA-1790); 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide (DA 8159) and pharmaceutically acceptable salts thereof.

Particularly preferred NEP inhibitors for such combined products for the treatment of MED or FSD are the compounds exemplified in WO 02/079143.

By cross reference herein to compounds contained in patents and patent applications which can be used in accordance with invention, we mean the therapeutically active compounds as defined in the claims (in particular of claim 1) and the specific examples (all of which is incorporated herein by reference).

If a combination of active agents is administered, then they may be administered simultaneously, separately or sequentially, in formulations which may be the same or different.
Biological Assays
Melanocortin Receptor Agonist Activity; Selectivity
Measurement of In Vitro Agonist Potency ($EC_{50}$) of Compounds Against Melanocortin Receptors Type 1 and 3 (MC1 and MC3).

Activation of melanocortin (MC) receptors by agonists results in activation of intracellular adenylate cyclase enzymes that synthesise the second messenger signalling molecule, adenosine 3',5'-cyclic monophosphate (cAMP). Changes in cAMP levels following treatment of recombinant MC1 and MC3 cell lines with test compound were measured and an MC1 and MC3 potency estimate ($EC_{50}$) calculated as follows:

Human embryonic kidney (HEK) or Chinese hamster ovary cell lines stably transfected with full length cDNA encoding human MC1 or MC3 receptors, respectively, were established using standard molecular biology methods. Test compounds were dissolved in dimethyl sulfoxide (DMSO) at 4 mM. 11 point half log unit increment dilution series of test compound, typically starting at 50 uM were prepared in a buffer comprised of phosphate buffered saline (PBS), 2.5% DMSO and 0.05% pluronic F-127 surfactant. Freshly cultured cells at 80-90% confluence were harvested and re-suspended in Dulbecco's Modified Eagle's Medium (DMEM). Cells (10,000 for MC3, 20,000 for MC1) were added to the test compound dilution series in a 384 well assay plate and incubated for 1 hour at 37° C. The relative cAMP concentration in each well was then measured using a β-galactosidase enzyme fragment complementation method purchased in kit form as the Discoverx cAMP II kit from GE Healthcare/Amersham Biosciences UK. In the case of MC1, 3-Isobutyl-1-methylxanthine (IBMX) at a concentration of 750 μM was included in DMEM as the cells were re-suspended for assay. The fluorescence readings taken from each assay well were converted into percent effect relative to maximum control wells corresponding to a concentration of alpha melanocyte stimulating hormone demonstrated to give a maximal effect. Sigmoidal curves were fitted to plots of $\log_{10}$ inhibitor concentration vs percent effect using a custom made software application called SIGHTS and $EC_{50}$ estimates determined by the software as the concentration of test compound giving an effect half way between the bottom and top assymptotes of the sigmoidal dose response curve. Each experiment included an $EC_{50}$ determination for alpha melanocyte stimulating hormone, which was used as a standard to track assay consistency and allow fair comparison between $EC_{50}$ estimates obtained in different experiments.

MC5 and MC4 $EC_{50}$ activity was determined as described by assay protocols D and E, respectively, in US2005/0176772 (pages 28-30).

Nle4, D-Phe7-α-MSH Inhibition at the MC4 Receptor

Nle4, Nle4, D-Phe7-α-MSH is a stable analogue of melanocyte-stimulating hormone (MSH), which is an agonist at the MC4 receptor (MC4R). Compounds can be evaluated for their ability to inhibit Nle4, Nle4, D-Phe7-α-MSH binding to membranes from cells expressing the MC4R using a competition binding assay versus [$^{125}$I] Nle4, D-Phe7-α-MSH.

Cells expressing the MC4R were subject to homogenisation and the membrane fragment isolated by differential centrifugation. CHO-CRE MC4R cell membranes were coupled to PVT-PEI-WGA SPA Beads type A for 2 hours, spun at 1000 RPM for 5 mins and suspended to a concentration of 300 ug bead/ml (0.15 ug membrane, 15 ug bead per well). Bead/membrane mix was incubated with 0.06 nM [$^{125}$I] Nle4, D-Phe7-α-MSH and 11 half-log concentrations of competitor ligand, in duplicate, in a total volume of 50 μl buffer per well (25 mM HEPES, 1 mM $MgCl_2$, 2.5 mM $CaCl_2$, 1% Pluronic F68, 1 complete EDTA protease inhibitor tablet/50 ml pH7). Non-specific binding was determined by the inclusion of 100 nM SHU9119. The reaction was initiated by the addition of bead/membranes and plates were incubated at room temperature for 12 hours (the first hour on a plate shaker), after which the amount of radioactivity present was determined using a Wallac plate counter. Ki values were determined by data analysis using appropriate software.

Preferably the compounds of the present invention exhibit a binding constant at the MC4 receptor expressed as an Ki value against Nle4, D-Phe7-α-MSH of lower than about 1000 nM, more preferably lower than 500 nM, yet more preferably lower than about 100 nM and more preferably still lower than about 50 nM, wherein said Ki value is determined using the assay described above.

Nle4, D-Phe7-α-MSH Inhibition at the MC3 Receptor

Nle4, D-Phe7-α-MSH is a stable analogue of melanocyte-stimulating hormone (MSH), which is an agonist at the MC3 receptor (MC3R). Compounds can be evaluated for their ability to inhibit Nle4, D-Phe7-α-MSH binding to membranes from cells expressing the MC3R using a competition binding assay versus [$^{125}$I] Nle4, D-Phe7-α-MSH.

Cells expressing the MC3R were subject to homogenisation and the membrane fragment isolated by differential centrifugation. CHO-CRE MC3R cell membranes were coupled to PVT-PEI-WGA SPA Beads type A for 2 hours, spun at 1000 RPM for 5 mins and suspended to a final assay concentration of 800 ug bead/ml (1.2 ug membrane, 40 ug bead per well). Bead/membrane mix was incubated with 0.06 nM Nle4, D-Phe7-α-MSH and 11 half-log concentrations of competitor ligand, in duplicate, in a total volume of 50 μl buffer per well (25 mM HEPES, 1 mM $MgCl_2$, 2.5 mM $CaCl_2$, 1% Pluronic F68, 1 complete EDTA protease inhibitor tablet/50 ml pH7).

Non-specific binding was determined by the inclusion of 100 nM SHU9119. The reaction was initiated by the addition of bead/membranes and plates were incubated at room temperature for 12 hours (the first hour on a plate shaker), after which the amount of radioactivity present was determined using a Wallac plate counter. Ki values were determined by data analysis using appropriate software.

High Density Drug-Drug Interactions (DDI) 3 μM Cocktail Screen

A drug interaction is a situation in which a substance affects the activity of another drug, i.e. the effects are increased or decreased, or together they produce a new effect that neither produces on its own. Drug interactions may be the result of various processes but a relatively common one is where one drug affects the pharmacokinetics of another by inhibiting the cytochrome P450 that metabolises it. Because of the importance of these phenomena, assessment of the DDI potential for new chemical entities (NCEs) is considered important early on in the drug discovery process.

The DDI cocktail screen in human liver microsomes (HLM) is run in a fully automated fashion and the aim of the screen is to provide a single-point assessment of the DDI potential of new chemical entity (NCE; tested at 3 μM) against the 4 primary cytochrome P450 enzymes, 1A2, 2D6, 2C9 and 3A4.

The substrate cocktail approach for P450 DDI utilizes human liver microsomes together with isoform-specific clinical drug probes and permits the simultaneous measurement of the inhibition of P450 1A2, 2C9, 2D6 & 3A4 activities in a single incubation. This is run in high throughput with simultaneous detection of metabolites by LC-MS/MS. This method has been thoroughly tested and evaluated using standard compounds. The probe substrates used are given in the table below.

| Microsome Source | Pooled human liver microsomes, |
|---|---|
| Microsome Concentration | 0.1 mg/ml |
| P450 Concentration | 0.03 μM |
| Regeneration System | NADPH (1.3 mM) |
| Assay Time | 8 min |

| Probe Substrate (Enzyme Probed) | Concentration |
|---|---|
| Tacrine (1A2) | 2 μM |
| Diclofenac (2C9) | 5 μM |

-continued

| | |
|---|---|
| Dextromethorphan (2D6) | 5 µM |
| Midazolam (3A4) Inhibitors | 2 µM |
| NCE (test compound) | 3 µM |
| Miconazole (universal control) | 3 µM |

Appearance of the metabolite of each substrate is measured over time in the presence and absence of the NCE (test compound/inhibitor) at a concentration of 3 µM. The compounds are assessed for their inhibitory potential as a percentage value and interpreted using the following scheme. These data are then used in conjunction with other measurements to evaluate the suitability of NCEs and to help with the design and progression of compounds.

| % Inhibition | IC50 |
|---|---|
| >75% | <1 µM |
| 25-75% | 1-10 µM |
| <25% | >10 µM |

AGRP Inhibition

Agouti related protein (AGRP) is a high affinity endogenous antagonist/inverse agonist for the MC4 receptor (Lu et al., 1994, *Nature* 371: 799-802; Oilman et al., 1997, *Science* 278: 135-138). AGRP levels are upregulated by fasting (Mizuno & Mobbs 1999, *Endocrinology*. 140: 4551-4557) and therefore it is important to assess the ability of anti-obesity agents acting through the MC4 receptor to inhibit the binding of AGRP. It has been ascertained that this C-terminal fragment of AGRP contains the MC4R binding determinants (Yang et al., 1999, *Mol Endocrinol* 13: 148-155), therefore, compounds can be evaluated for their ability to inhibit AGRP binding to membranes from cells expressing the MC4R using a competition binding assay versus [$^{125}$I]AGRP(87-132). To this end cells expressing the MC4R were subject to homogenisation and the membrane fragment isolated by differential centrifugation. CHO-CRE MC4R cell membranes (12 µg protein) were incubated with 0.3 nM [$^{125}$I]AGRP(87-132) and 11 half-log concentrations of competitor ligand, in duplicate, in a total volume of 100 µl buffer (25 mM HEPES, 1 mM MgCl$_2$, 2.5 mM CaCl$_2$, 0.5% BSA pH 7.0). Non-specific binding was determined by the inclusion of 1 µM SHU9119. The reaction was initiated by the addition of membranes and plates were incubated at room temperature for 2 hours. The reaction was terminated by rapid filtration onto GF/C filters (presoaked in 1% PEI) using a vacuum harvester followed by five 200 µl washes of ice cold wash buffer (Binding buffer containing 500 mM NaCl). The filters were soaked in 50 µl scintillation fluid and the amount of radioactivity present was determined by liquid scintillation counting. Ki values were determined by data analysis using appropriate software.

Preferably the compounds of the present invention exhibit a binding constant at the MC4 receptor expressed as an Ki value against AGRP of lower than about 1000 nM, more preferably lower than 500 nM, yet more preferably lower than about 100 nM and more preferably still lower than about 50 nM, wherein said Ki value is determined using the assay described above. Using this assay, compounds according to the present invention exhibit a binding constant at the MC4 receptor expressed as an Ki value against AGRP lower than 1000 nM.

Food Intake Study: to Assess the Efficacy of an MC4 Agonist on Food Intake and Body Weight Over a 24 Hour Period in the Male Rat Rats will be acclimatised to single housing and reverse lighting conditions (9.30 am-9.30 pm) for approximately two weeks before the start of the study. Rats will be acclimatised to the Techincal Scientific Equipment* (TSE) cages approximately 24 hours prior to the study day. Rats will be randomly assigned to a treatment group on the morning of the study based on its weight (n=5/treatment). Each rat will either receive the MC4 agonist or vehicle orally just before lights go out. Following dosing the rat will be immediately placed back in to the TSE cage and food intake and water consumption will be monitored throughout the course of the study (24 hours). Locomotor activity will also be monitored in the form of light beam breaks. At the end of the study rats will be killed by exsanguination under terminal anaesthesia by Isoflurane. Blood will be removed from the rat by cardiac puncture and analysed for drug concentration levels and biomarkers.

The data are expressed as mean±SEM and comparisons between the control and the treatment is analysed by ANOVA. Statistical significance is accepted at a level of $p<0.05$.

In vitro Metabolism Rate Determination (Human Liver Microsome (HLM); Rat Liver Microsome (RLM) Assay)

Many drugs are metabolised by the cytochrome P450 mono-oxygenase system. This enzyme is found in high concentrations in the liver and is bound to the endoplasmic reticulum of the hepatocyte. The enzyme system can be obtained in semi-purified state by the preparation of the hepatic microsomal fractions. Determining a compound's in vitro half-life in such a system provides a useful indicator of metabolic stability.

Materials And Reagents

All reagents are ANALAR grade.
1. 200 mM Phosphate buffer (Sigma)—100 ml 1M Phosphate buffer pH7.4 dissolved with 400 ml MilliQ water. If necessary, pH should be adjusted with concentrated orthophosphoric acid to pH 7.4, made up monthly and stored refrigerated (2-8° C.).
2. 0.1 M MgCl$_2$6H$_2$O (BDH)—2.032 g dissolved in 100 ml MilliQ water, and stored refrigerated (2-8° C.).
3. 0.02M NADP (Sigma)—15.3 mg dissolved in 1000 µl MilliQ water—and then stored refrigerated (2-8° C.) for further use.
4. 0.1 M D-L Isocitric acid (Sigma)—129 mg dissolved in 5 ml MilliQ water—and then stored refrigerated (2-8° C.) for further use.
5. Isocitric dehydrogenase, Type IV (Sigma)—stored refrigerated (2-8° C.).
6. Stock solution of substrate (approximately 1 mg/ml) in miscible organic solvents such as methanol, ethanol or water, stored refrigerated (2-8° C.).
7. 50 mM p-Nitroanisole (PNA) (Aldrich)—7.65 mg dissolved in 1 ml methanol, and stored refrigerated (2-8° C.) until ready for use.
8. 50 µM p-Nitrophenol (PNP) (Sigma)—0.69 mg dissolved in 100 ml water and stored refrigerated (2-8° C.).
9. 20% Trichloroacetic acid (TCA) (BDH)—20 g dissolved in 100 ml MilliQ water, made up in amber glassware and stored at room temperature.
10. 10M Sodium hydroxide (BDH)—40 g dissolved in 100 ml MilliQ water (care should be exercised when preparing this solution as this reaction is exothermic), made up in "safebreak" glassware and stored at room temperature.
11. Hepatic or Supermix microsomes stored at −80° C. should be defrosted immediately prior to use, kept on ice and dispensed.

12. MilliQ water.
13. Thermostatically controlled shaking water bath set to give a temperature in the incubation of approx 37° C.
14. Reagent for termination of incubation (typically organic solvent, acid or base).

Methodology For In Vitro Rate Determination Using Hepatic & Supermix Microsomes

The method outlined below is for a total incubation volume of 1.5 ml.

1. The following mixture is prepared in a test tube:

| Reagent | Stock concentration | Concentration in incubation | Volume added (for 1.5 ml incubation) |
|---|---|---|---|
| Phosphate buffer pH 7.4 | 200 mM | 50 mM | 375 μl |
| MgCl$_2$ | 0.1 M | 5 mM | 75 μl |
| Isocitric acid | 0.1 M | 5 mM | 75 μl |
| Isocitric dehydrogenase | on bottle | 1 unit per ml* | see below* |

*This volume is calculated for each new batch of isocitric dehydrogenase
e.g. Protein concentration = 18 mg/ml
Enzyme activity = 3.3 units/mg
therefore Specific activity = 3.3 × 18 units/ml = 59 units/ml
For a 1.5 ml incubation 1.5 units of enzyme activity are required =
$\frac{1.5}{59} \times 1000 = 25.4$ μl.

2. Defrost microsomes at room temperature and add sufficient microsomes to give a final concentration of 0.5 nmol cytochrome P450/ml of incubation e.g. for a 1.5 ml incubation, the volume of microsomes to be added is:

$$\frac{P450 \text{ concentration required in incubation} \times \text{incubation volume}}{\text{cytochrome } P450 \text{ concentration in microsomal prep.}}$$

3. Add sufficient MilliQ water to give a total incubation volume of 1.425 ml.
4. Remove 237.5 μl of incubation mix and place in test tube for PNA positive control. Add 2.5 μl of PNA solution, whirlimix, and put tube into a rack in the thermostatically controlled shaking water bath
5. Remove 100 μl for no substrate control and dispense in test tube. Place test tube in a rack in the thermostatically controlled shaking water bath.
6. Add substrate to the incubation. The substrate should be at an initial concentration of 1 μM. The volume of substrate required in the remaining 1.162.5 ml incubation is calculated as follows:

$$\frac{RMM \times \text{incubation vol.} \times \text{initial conc. in incubation}}{1000 \times \text{stock substrate solution conc.}}$$

N.B. The volume of organic solvent added should not exceed 0.1% of the total incubation volume.

7. Remove 100 μl of incubation mix into test tube for no cofactor control. Whirlimix and put into a rack in the thermostatically controlled shaking water bath.
8. Pre-incubate the tube containing the incubation mix, also positive control and no cofactor tubes in the thermostatically controlled shaking water bath set at 37° C. for approx 5 min.
9. Add NADP to initiate reaction (75 μl to each 1.162.5 ml incubation mix, 12.5 μl to positive control tube and 5 μl to no substrate tube) and take first time point immediately. The PNA positive control, no cofactor control and no substrate tubes are incubated for the total incubation time.
10. Remove 100 μl aliquots up to 9 different sampling points from 0 to 60 min (usually 0, 3, 5, 10, 15, 20, 30, 45 & 60 min) and terminate reaction. Longer incubation times can be used, but, after 120 min the microsomes deteriorate. The reaction may be terminated by addition of organic solvent, acid or base. At the end of the incubation process the no cofactor and no substrate controls in a similar manner i.e. terminate with the same reagent.
11. PNA Positive Control Procedure:

After the final sample has been taken, remove the positive control and add 1 ml 20% TCA to this tube. Also prepare a tube containing 250 μl of a PNP standard at 50 μM, and add 1 ml 20% TCA. Whirlimix both tubes and leave for approx 5 min to allow the protein to precipitate.

Centrifuge both tubes for approx 5 min in an instrument set at 3500 rpm. Remove 1 ml of supernatant and place into clean test tubes, discard the remainder.

Add 1 ml 10M NaOH to the supernatant, whirlimix, and leave to stand for approx min. Blank spectrophotometer with distilled water at 400 nm then measure absorbance of the PNP standard against distilled water. The microsomal 4-nitroanisole O-demethylase activity is calculated as follows:

Calculation of Results $$\frac{\text{Absorbance sample} \times \text{nmoles } PNP \text{ in standard(ie 12.5 nmoles)}}{\text{Absorbance } PNP \text{ } std \times 60 \times 0.125} =$$

nmoles/min/nmol P450

The activity value from the incubation MUST be equal to or greater than 85% of the mean value of the batch used for the incubation to be valid. If this criteria is not met, then the incubation must be repeated.

11. Analyse samples (including no cofactor and no substrate control) by a specific assay for the substrate to determine the disappearance kinetics.

Analysis Of Data

Data obtained using the procedure described above can be quantified in terms of the substrates in vitro intrinsic clearance (Clint). Providing that the substrate concentration is below Km, the metabolism should be 1st order giving a log-linear plot of substrate disappearance with time.

The in vitro half-life of the substrate can be determined by plotting the natural logarithm (ln) of a measure of relative substrate concentration (e.g. drug/internal standard ratio) against time and fitting the line of best fit to this data. The gradient of this line is the first order rate constant (k) for the substrate disappearance and is determined by regression analysis. This rate constant can be converted to the half-life according to the following equation: —

$$\text{in vitro half-life}(t_{1/2}) = -\frac{\text{Ln}2}{k}$$

Alternatively the rate constant can be converted to an intrinsic clearance (Clint) according to the following equation: —

$Clint$(μl/min/mg)=($k$/protein concentration in incubation (mg/ml))*1000

Preferably the compounds of the present invention exhibit a clearance, as determined by the above assay, expressed as a value of lower than about 200 μL/min/mg, more preferably lower than 100 μL/min/mg, yet more preferably lower than about 50 μL/min/mg and more preferably still lower than about 20 μL/min/mg. Using this assay, compounds according to the present invention which have been tested exhibit a clearance lower than 200 μL/min/mg.

Administration Methods

Compounds of the invention intended for pharmaceutical use may be administered as crystalline or amorphous products. They may be obtained, for example, as solid plugs, powders, or films by methods such as precipitation, crystallization, freeze-drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences,* 19th Edition (Mack Publishing Company, 1995).

Accordingly the present invention provides for a pharmaceutical composition comprising a compound of formula (I) and a pharmaceutically acceptable diluent or carrier.

Any suitable route of administration may be employed for providing a mammal, especially a human with an effective dosage of a compound of the present invention. For example, oral (including buccal and sublingual administration), rectal, topical, parental, ocular, pulmonary, nasal, and the like may be employed. Dosage forms include tablets, troches, dispersions, suspensions, solutions, capsules, creams, ointments, aerosols, and the like. Preferably compounds of formula (I) are administered orally or intranasally.

The effective dosage of active ingredient employed may vary depending on the particular compound employed, the mode of administration, characteristics of the mammal to be treated (e.g. body weight), the condition being treated and the severity of the condition being treated. Such dosage may be ascertained readily by a person skilled in the art.

For the treatment of sexual dysfunction compounds of the present invention are given in a dose range of from about 0.001 milligram (mg) to about 1000 mg, preferably from about 0.001 mg to about 500 mg, more preferably from about 0.001 mg to about 100 mg, even more preferably from about 0.001 mg to about 50 mg and especially from about 0.002 mg to about 25 mg per kilogram of body weight, preferably as a single dose orally or as a nasal spray. For example, oral administration may require a total daily dose of from about 0.1 mg up to about 1000 mg, while an intravenous dose may only require from about 0.001 mg up to about 100 mg. The total daily dose may be administered in single or divided doses and may, at the physician's discretion, fall outside of the typical range given herein.

When treating obesity, in conjunction with diabetes and/or hyperglycemia, or alone, generally satisfactory results are obtained when the compounds of the present invention are administered at a daily dosage of from about 0.0001 mg to about 1000 mg, preferably about 0.001 mg to about 500 mg, more preferably about 0.005 mg to about 100 mg and especially about 0.005 mg to about 50 mg per kilogram of animal body weight, preferably given in a single dose or in divided doses two to six times a day, or in sustained release form. In the case of a 70 kg adult human, the total daily dose will generally be from about 0.7 mg up to about 3500 mg. This dosage regimen may be adjusted to provide the optimal therapeutic response.

When treating diabetes mellitus and/or hyperglycemia, as well as other diseases or disorders for which compounds of formula I are useful, generally satisfactory results are obtained when the compounds of the present invention are administered at a daily dosage of from about 0.001 mg up to about 100 mg per kilogram of animal body weight, preferably given in a single dose or in divided doses two to six times a day, or in sustained release form. In the case of a 70 kg adult human, the total daily dose will generally be from about 0.07 mg up to about 350 mg. This dosage regimen may be adjusted to provide the optimal therapeutic response.

These dosages are based on an average human subject having a weight of about 65 kg to 70 kg. The physician will readily be able to determine doses for subjects whose weight falls outside this range, such as infants, the elderly and the obese.

The compounds of the invention may be administered orally. Oral administration may involve swallowing, so that the compound enters the gastrointestinal tract, and/or buccal, lingual or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet. may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 wt % to 5 wt % of the tablet, and glidants may comprise from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt % of the tablet.

Other possible ingredients include anti-oxidants, colourants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *Pharmaceutical Dosage Forms: Tablets*, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula I, a film-forming polymer, a binder, a solvent, a humectant, a plasticiser, a stabiliser or emulsifier, a viscosity-modifying agent and a solvent. Some components of the formulation may perform more than one function.

The compound of formula I may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula I may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in *Pharmaceutical Technology On-line*, 25(2), 1-14 by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(dl-lactic-coglycolic)acid (PGLA) microspheres.

The compounds of the invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose, blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 0.001 mg to 10 mg of the compound of formula (I). The overall daily dose will typically be in the range 0.001 mg to 40 mg which may be administered in a single dose or, more usually, as divided doses throughout the day.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, gels, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

Other aspects of the invention are enumerated in the claims.

| Example number | MC4 EC50 (nM) | MC4 MSH Ki (nM) | MC3 EC50 (nM) | MC3 MSH Ki (nM) | MC4 AgRP Ki (nM) | HLM (μL/min/mg) | RLM (μL/min/mg) | % Inhibition of 3A4 metabolism at 3 uM |
|---|---|---|---|---|---|---|---|---|
| 1 | <0.52 | | 43.9 | | 39 | <7.0 | <8.5 | 54 |
| 2 | 4.53 | 27 | 4.26 | 124 | 59 | <12.0 | 31 | 64 |
| 3 | 11.9 | | 16.4 | | | <7.0 | <19.8 | 60 |
| 4 | | | 55.9 | | 51 | 60 | 74 | 38 |
| 5 | 137 | | 203 | | 552 | <7.0 | 27 | 34 |
| 6 | 18.9 | | 1460 | | 456 | | <8.5 | 32 |
| 7 | 40 | | 1600 | | 714 | 21 | 11 | 19 |
| 8 | 27.5 | | 1090 | | 643 | >440 | >510 | 94 |
| 9 | 39.3 | | 520 | | 523 | 240 | 411 | 68 |
| 10 | 11.9 | 276 | 493 | 977 | 223 | 20.5 | 42 | 19 |
| 11 | 111 | | | | 417 | 14 | | |
| 12 | 91.6 | | | | | >352 | 88.5 | |
| 13 | 37.6 | | 1020 | | 106 | | | 6 |
| 14 | 115 | | 129 | | | <9.0 | <9.75 | |
| 15 | 53.9 | | >33400 | | | | | |
| 16 | 34.3 | | 323 | | 251 | <45.5 | <8.5 | 83 |
| 17 | 1.59 | 112 | 54.9 | 332 | 20 | >440 | >510 | 35 |
| 18 | 55.5 | | >8520 | | 965 | 67 | 68 | 34 |
| 19 | 6.5 | 85.4 | 425 | 568 | 79 | 21 | 21 | 50 |
| 20 | 16.4 | 251 | 1120 | 1020 | 253 | 31 | 51.5 | 35 |
| 21 | 2.81 | | 283 | | 66 | 144 | 58.5 | 25 |
| 22 | 19.8 | | 1050 | 5560 | 5960 | 179 | 96 | 54 |
| 23 | 4.75 | 65.7 | 185 | 264 | 79 | <15.5 | <8.5 | 35 |
| 24 | 59.3 | | 2510 | | >955 | 355 | >510 | 87 |
| 25 | 12.4 | 10.9 | 189 | <0.105 | 278 | 308 | 172 | 16 |
| 26 | 22.5 | | 4210 | | 363 | 70 | >510 | 61 |
| 27 | 4.54 | | 390 | | 100 | 51 | 31 | 64 |
| 28 | 24.4 | | 938 | 1670 | 516 | 33 | 51 | 77 |
| 29 | 7.54 | | | | 40 | 105 | 36 | 59 |
| 30 | 5.77 | | 61.5 | | 112 | 141 | 69.5 | 38 |
| 31 | 22.9 | | 410 | | 526 | 188 | 292 | 60 |
| 32 | 8.78 | 150 | 76.6 | 456 | 160 | 8 | <8.5 | 31 |
| 33 | 13.4 | | 193 | | 220 | 186 | 72 | 19 |
| 34 | 39.2 | | | | 375 | <7.0 | <8.5 | 50 |
| 35 | 62.2 | | 878 | | 386 | 100 | 92 | 46 |
| 36 | 168 | | | | 1020 | <7.0 | 17 | 59 |
| 37 | | | 325 | | 422 | 19.5 | 23 | 45 |
| 38 | 102 | | | | 336 | <7.0 | <8.5 | 58 |
| 39 | | | 2100 | | 751 | 95 | 58 | 30 |
| 40 | 69.8 | | 580 | | 430 | <7.0 | <8.5 | 64 |
| 41 | 655 | | >33300 | | 3750 | 21 | 30 | 52 |
| 42 | | | >20300 | | 888 | 25 | 25 | 59 |
| 43 | 49.3 | | 1590 | | 248 | 37 | | 44 |
| 44 | 284 | | >9630 | | 2130 | | | 27 |
| 45 | 44.4 | | 66.1 | | 251 | <7.0 | <8.5 | 69 |
| 46 | 15 | | 50.8 | 551 | 134 | <7.0 | <8.5 | 74 |

Figure 2:
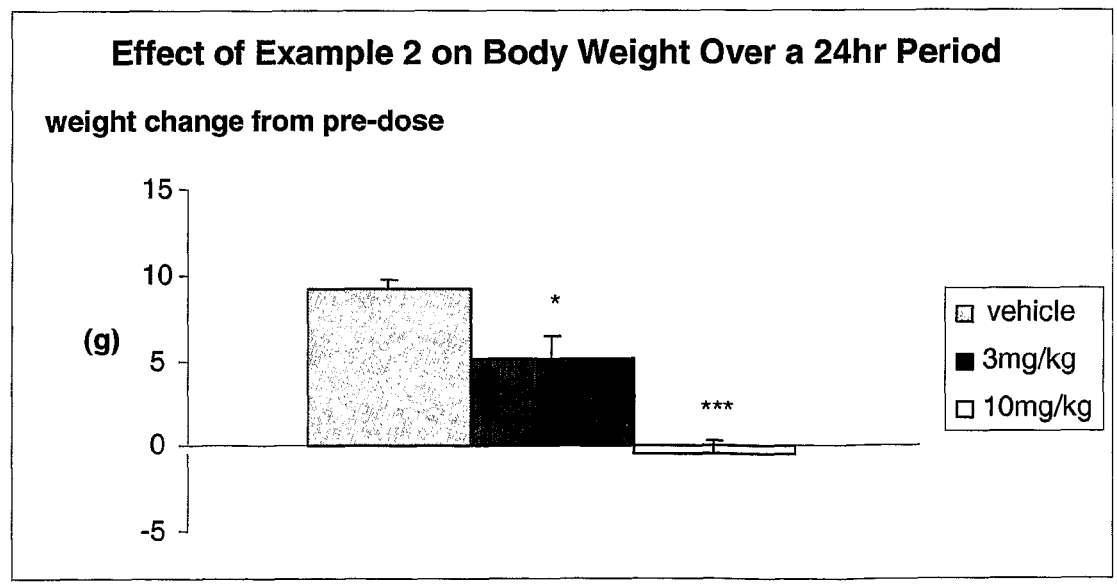
FIG. 2 shows the effects of the compound of Example 2 at 3 mg/kg and 10 mg/kg and vehicle on body weight change over 24 hours.

The effects of the compound of Example 2 at 3 mg/kg and 10 mg/kg on cumulative food intake over 24 hours, and body weight change over 24 hours, compared to vehicle, are expressed in FIGS. 1 and 2.

The invention is illustrated by the following non-limiting examples in which the following abbreviations and definitions are used:

APCI atmospheric pressure chemical ionisation mass spectrum
$[\alpha]_D$ specific rotation at 589 nm.
br broad
Celite® filter agent
δ chemical shift
d doublet
dd double doublet
EI electrospray ionisation
Ex example
LRMS low resolution mass spectrum
m multiplet
m/z mass spectrum peak
NMR nuclear magnetic resonance
Prec precursor
Prep preparation
psi pounds per square inch
q quartet
s singlet
t triplet
tlc thin layer chromatography For synthetic convenience whilst in many instances compounds have been initially isolated in their free-base form, these have often been converted to their corresponding hydrochloride salts for analytical identification purposes. For the avoidance of doubt, both the free-base and HCl salt forms are considered provided herein.

For the avoidance of doubt, named compounds used herein have been named using ACD Labs Name Software v7.11™.

EXAMPLES

Example 1

6-[(3S,4S)-3-(5-Chloropyridin-2-yl)-4-{[(3R,4R,5S)-4-(4-fluorophenyl)-4-hydroxy-3,5-dimethylpiperidin-1-yl]carbonyl}pyrrolidin-1-yl]nicotinonitrile

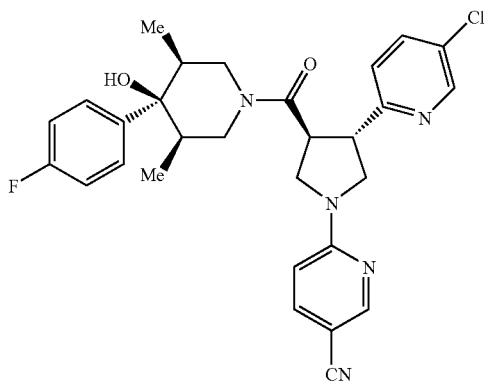

2-Chloro-5-cyanopyridine (96 mg, 0.69 mmol) was added to a solution of the pyrrolidine from preparation 10 (200 mg, 0.46 mmol) and N-ethyldiisopropylamine (0.32 mL, 1.8 mmol) in acetonitrile (10 mL) and the mixture was heated at 70° C. under nitrogen overnight. The solvent was removed in vacuo and the residue was purified by column chromatography (silica) eluting with dichloromethane, increasing polarity to 5% methanol in dichloromethane, to give the title compound (191 mg, 77%) as a white solid. $^1$H NMR (CD$_3$OD, 400 MHz) δ 0.4-0.6 (6H, 4×d), 0.78-0.82, 1.60-1.68 and 1.97-2.05 (2H, 3×m), 2.73-2.80 (1H, m), 3.00-3.20 (1H, m), 3.68-4.37 (8H, m), 6.62 (1H, m), 7.01-7.08 and 7.37-7.48 (5H, 2×m), 7.74 (1H, m), 7.80 and 7.95 (1H, 2×dd), 8.40 (1H, m), 8.57 and 8.60 (1H, 2×d); LRMS (EI$^+$) 534 [MH$^+$]; $[\alpha]_D^{25}$=−47.0 (c=0.215, MeOH).

Example 2

6-[(3S,4S)-3-(5-Chloropyridin-2-yl)-4-{[(3R,4R,5S)-4-(4-fluorophenyl)-4-hydroxy-3,5-dimethylpiperidin-1-yl]carbonyl}pyrrolidin-1-yl]pyridazine-3-carbonitrile

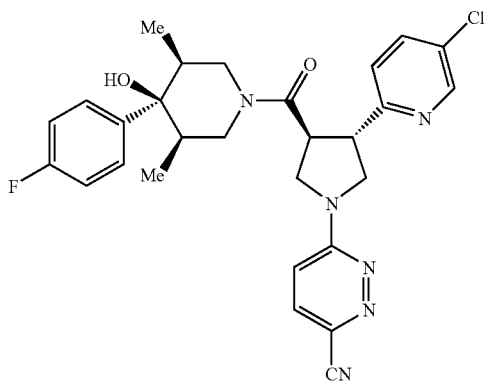

3-Chloro-6-cyanopyridazine (prepared according to U.S. Pat. No. 3,637,691) (20 mg, 0.14 mmol) was added to a solution of the pyrrolidine from preparation 10 (40 mg, 0.09 mmol) and N-ethyldiisopropylamine (0.06 mL, 0.37 mmol) in acetonitrile (10 mL) and the mixture was heated at 70° C. under nitrogen overnight. The solvent was removed in vacuo and the residue was purified by column chromatography (silica) eluting with dichloromethane, increasing polarity to 5% methanol in dichloromethane, to give the title compound (41 mg, 83%) as a white solid. $^1$H NMR (CD$_3$OD, 400 MHz) δ 0.4-0.6 (6H, 4×d), 0.78-0.85, 1.60-1.69 and 1.97-2.10 (2H, 3×m), 2.72-2.80 (1H, m), 3.00-3.23 (1H, m), 3.68-4.38 (8H, m), 6.99-7.08 and 7.38-7.50 (6H, 2×m), 7.70 (1H, d), 7.80 and 7.94 (1H, 2×dd), 8.58 and 8.61 (1H, 2×d); LRMS (EI$^+$) 535 [MH$^+$].

Example 3

(3R,4R,5S)-1-{[(3S,4S)-1-(6-Chloropyridazin-3-yl)-4-(5-chloropyridin-2-yl)pyrrolidin-3-yl]carbonyl}-4-(4-fluorophenyl)-3,5-dimethylpiperidin-4-ol

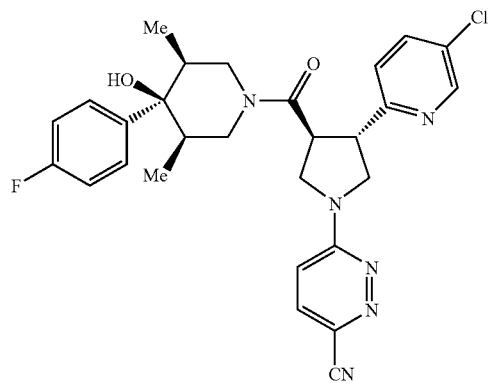

1,6-Dichloropyridazine (173 mg, 1.2 mmol) was added to a solution of the pyrrolidine from preparation 10 (100 mg, 0.23 mmol) and N-ethyldiisopropylamine (0.16 mL, 0.93 mmol) in acetonitrile (5 mL) and the mixture was heated at 70° C. under nitrogen overnight. The solvent was removed in vacuo and the residue was purified by column chromatography (silica) eluting with dichloromethane, increasing polarity to 5% methanol in dichloromethane, to give the title compound (52 mg, 42%) as a white solid. $^1$H NMR (CD$_3$OD, 400 MHz) δ 0.4-0.6 (6H, 4×d), 0.78-0.85, 1.60-1.69 and 1.97-2.10 (2H, 3×m), 2.72-2.80 (1H, m), 3.00-3.23 (1H, m), 3.68-4.38 (8H, m), 6.99-7.08 and 7.38-7.50 (6H, 2×m), 7.70 (1H, d), 7.80 and 7.94 (1H, 2×dd), 8.58 and 8.61 (1H, 2×d); LRMS (EI$^+$) 544 [MH$^+$].

Example 4

(3R,4R,5S)-1-{[(3S,4S)-4-(5-chloropyridin-2-yl)-1-(6-methoxypyridazin-3-yl)pyrrolidin-3-yl]carbonyl}-4-(4-fluorophenyl)-3,5-dimethylpiperidin-4-ol

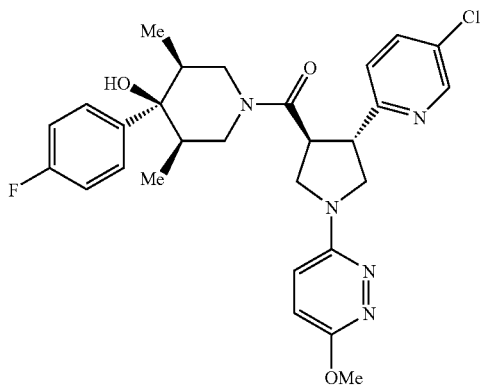

Sodium t-butoxide (31 mg, 0.32 mmol), 3-chloro-6-methoxypyridazine (34 mg, 0.23 mmol), tris(dibenzylideneacetone)dipalladium (0) (8.5 mg, 0.009 mmol) and 2,2'-bis(diphenylphosphino)-1,1'-binaphthalene (11.5 mg, 0.0185 mmol) were added to a solution of the pyrrolidine from preparation 10 (100 mg, 0.23 mmol) in toluene (10 mL) and the mixture was heated at 80° C. under nitrogen overnight. The solvent was removed in vacuo and the residue was taken up in ethyl acetate (25 mL), washed with water, dried (MgSO4) and evaporated. Purification by column chromatography (silica) eluting with dichloromethane, increasing polarity to 5% methanol in dichloromethane, gave the title compound (48 mg, 40%) as a yellow foam. $^1$H NMR (CD$_3$OD, 400 MHz) δ 0.4-0.62 (d+t+t, 6H), 0.86 (m, 1H), 1.65 (m, 1H), 1.93-2.08 (br, 1H), 2.75 (m, 1H), 3.17 (t, 1H), 3.74 (m, 3H), 3.95 (s, 3H), 3.96-4.21 (m, 3H), 4.32 (d, 1H), 6.98-7.1 (m, 5H), 7.38-7.48 (m, 2H), 7.79+7.48 (2×dd, 1H), 8.56 (d, 1H); LRMS (EI$^+$) 540 [MH$^+$].

Example 5

(3R,4R,5S)-4-(4-chlorophenyl)-1-{[(3S,4S)-1-(6-chloropyridazin-3-yl)-4-(5-fluoropyridin-2-yl)pyrrolidin-3-yl]carbonyl}-3,5-dimethylpiperidin-4-ol

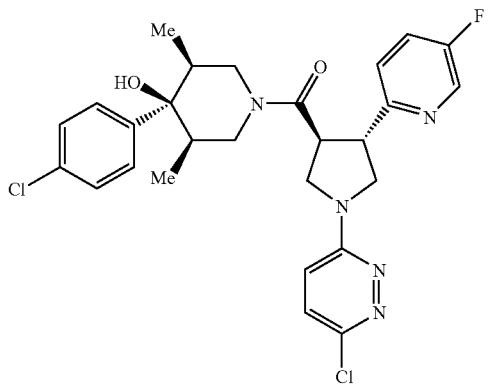

To a solution of (3R,4R,5S)-4-(4-chlorophenyl)-1-{[(3S,4S)-4-(5-fluoropyridin-2-yl)pyrrolidin-3-yl]carbonyl}-3,5-dimethylpiperidin-4-ol (prepared by the same methods as used for the amine of preparation 10, starting from the aldehyde of preparation 17 and (3R,4s,5S)-4-(4-chlorophenyl)-3,5-dimethylpiperidin-4-ol, prepared according to international patent application publication number WO 2005/077935) (120 mg, 0.28 mmol) in dimethyl sulfoxide (2 mL) was added 3,6-dichloropyridazine (98 mg, 0.56 mmol), triethylamine (0.12 mL, 0.84 mmol), and caesium fluoride (13 mg, 0.084 mmol). The mixture was stirred at 110° C. under nitrogen for 3 hours. The reaction mixture was diluted with methanol (5 mL) and loaded onto an SCX column, eluting with methanol to remove non basic material and dimethylsulfoxide, followed by 2M NH$_3$ in methanol to elute the basic product. The solvent was removed in vacuo to yield the title compound (74 mg, 49%) as a colourless gum. $^1$H NMR (CD$_3$OD, 400 MHz) δ 0.44-0.60 (6H, 4×d), 0.95-1.02, 1.64-1.73 and 1.94-2.09 (2H, 3×m), 2.69-2.79 (1H, m), 2.99-3.06 and 3.16-3.22 (1H, 2×m), 3.74-3.79 (3H, m), 4.01-4.24 (4H, m), 4.32-4.36 (1H, m), 7.02-7.07 (1H, m), 7.29-7.70 (7H, m), 8.45-8.49 (1H, m); LRMS (EI$^+$) 544 [MH+].

Example 6

6-[(3S,4S)-3-{[(3R,4R,5S)-4-(4-chlorophenyl)-4-hydroxy-3,5-dimethylpiperidin-1-yl]carbonyl}-4-(5-fluoropyridin-2-yl)pyrrolidin-1-yl]pyridazin-3(2H)-one

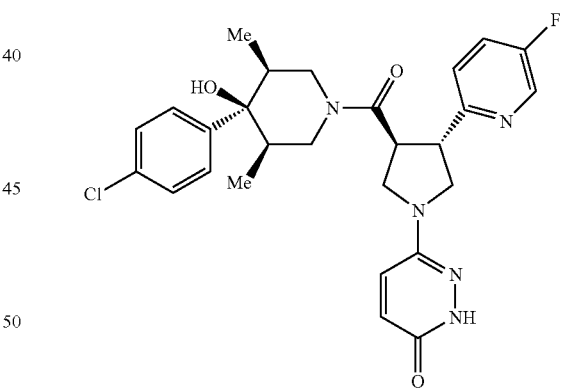

A solution of chloropyridazine from Example 5 (70 mg, 0.13 mmol) was dissolved in degassed acetic acid and stirred at reflux under nitrogen overnight. The solvent was removed in vacuo and the residue was purified by column chromatography (silica) eluting with dichloromethane/methanol/aq. ammonia 95/5/0.5. This yielded the title compound as an off-white solid (37 mg, 55%). $^1$H NMR (CD$_3$OD, 400 MHz) δ 0.43-0.59 (6H, 4×d), 0.94-1.03, 1.64-1.73 and 1.93-2.03 (2H, 3×m), 2.65-2.78 (1H, m), 2.97-3.03 and 3.14-3.20 (1H, 2×m), 3.62-3.79 (3H, m), 3.86-4.17 (4H, m), 4.31-4.35 (1H, m), 6.88-6.91 (1H, m), 7.30-7.42 (5H, m), 7.47-7.57 (1H, m), 7.63-7.68 (1H, m), 8.44-8.48 (1H, m); LRMS (EI+) 526 [MH+].

Example 7

6-[(3S,4S)-3-{[(3R,4R,5S)-4-(4-chlorophenyl)-4-hydroxy-3,5-dimethylpiperidin-1-yl]carbonyl}-4-(5-fluoropyridin-2-yl)pyrrolidin-1-yl]-2-methylpyridazin-3(2H)-one

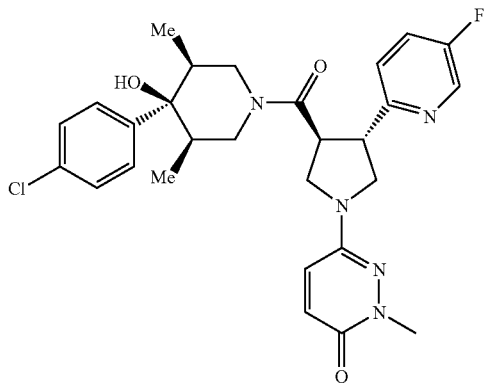

To a solution of the pyridazinone from Example 6 (30 mg, 0.057 mmol) in dimethylformamide (2 mL) was added sodium hexamethydisilazide 1M in tetrahydrofuran (0.07 mL, 0.07 mmol) and lithium bromide (6 mg, 0.07 mmol). The mixture was stirred at room temperature under nitrogen for 30 minutes then methyl iodide (0.004 mL, 0.07 mmol) was added and the mixture was stirred under nitrogen at room temperature for 2 hours. The solvent was removed in vacuo and the residue was purified by column chromatography (silica) eluting with dichloromethane/methanol/aq. ammonia 95/5/0.5. This yielded the title compound as a yellow solid. $^1$H NMR (CD$_3$OD, 400 MHz) δ 0.44-0.59 (6H, 4×d), 0.94-1.03, 1.64-1.73 and 1.95-2.04 (2H, 3×m), 2.68-2.78 (1H, m), 2.95-3.01 and 3.14-3.21 (1H, 2×m), 3.62-3.81 (6H, m), 3.87-4.17 (4H, m), 4.31-4.35 (1H, m), 6.87-6.90 (1H, m), 7.25-7.34 (4H, m), 7.38-7.42 (1H, m), 7.48-7.58 (1H, m), 7.64-7.69 (1H, m), 8.44-8.48 (1H, m); LRMS (EI+) 540 [MH+].

Example 8

(3R,4R,5S)-1-{[(3S,4S)-4-(5-chloropyridin-2-yl)-1-(5-fluoropyridin-3-yl)pyrrolidin-3-yl]carbonyl}-3,5-dimethyl-4-pyridin-2-ylpiperidin-4-ol

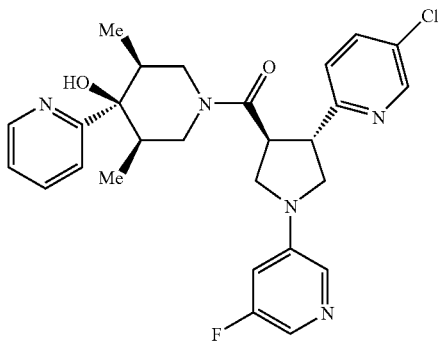

To a solution of (3R,4R,5S)-1-{[(3S,4S)-4-(5-chloropyridin-2-yl)pyrrolidin-3-yl]carbonyl}-3,5-dimethyl-4-pyridin-2-ylpiperidin-4-ol (prepared by the same method as used for the amine of preparation 10, starting from (3R,4s,5S)-3,5-dimethyl-4-pyridin-2-ylpiperidin-4-ol, prepared according to international patent application publication number WO 2005/077935) (50 mg, 0.12 mmol) in toluene (5 mL), was added 3-bromo, 5-fluoropyridine (25 mg, 0.14 mmol), tris(dibenzylidineacetone)dipalladium (4.4 mg, 0.0048 mmol), BINAP (6 mg, 0.0096 mmol) and sodium tert-butoxide (26 mg, 0.27 mmol). The mixture was stirred at 80° C. under nitrogen overnight. The solvent was removed in vacuo and the residue was purified by column chromatography (silica) eluting with dichloromethane/methanol/aq. ammonia 99/1/0.1, increasing polarity to 95/5/0.5. This gave the title compound (11 mg, 18%) as a yellow gum. $^1$H NMR (CD$_3$OD, 400 MHz) δ 0.33-0.53 (6H, 4×d), 0.81-0.93, 1.81-1.92 and 2.08-2.28 (2H, 3×m), 2.69-2.78 (1H, m), 2.99-3.20 (1H, m), 3.61-3.94 (5H, m), 4.01-4.23 (2H, m), 4.34-4.42 (1H, m), 6.81-6.90 (1H, m), 7.26-7.50 (3H, m), 7.70-7.94 (4H, m), 8.51-8.62 (2H, m); LRMS (EI+) 510 [MH+].

Example 9

(3R,4R,5S)-1-{[(3S,4S)-4-(5-chloropyridin-2-yl)-1-pyridazin-3-ylpyrrolidin-3-yl]carbonyl}-3,5-dimethyl-4-pyridin-2-ylpiperidin-4-ol

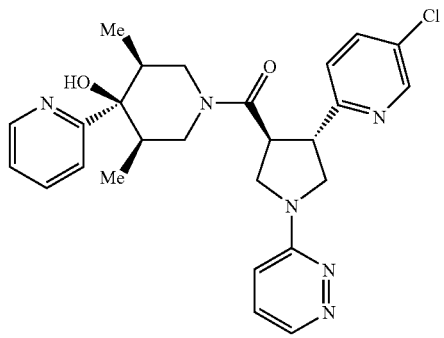

To a solution of (3R,4R,5S)-1-{[(3S,4S)-4-(5-chloropyridin-2-yl)pyrrolidin-3-yl]carbonyl}-3,5-dimethyl-4-pyridin-2-ylpiperidin-4-ol (prepared by the same method as used for the amine of preparation 10, starting from (3R,4s,5S)-3,5-dimethyl-4-pyridin-2-ylpiperidin-4-ol, prepared according to international patent application publication number WO 2005/077935) (50 mg, 0.12 mmol) in DMSO (2 mL) was added 3-chloropyridazine (28 mg, 0.24 mmol), caesium fluoride (18 mg, 0.12 mmol) and triethylamine (0.05 mL, 0.36 mmol). The mixture was stirred at 100° C. under nitrogen overnight. The reaction mixture was diluted with 10 mL ethyl acetate and washed with 3×20 mL of water. The combined aqueous extracts were extracted with 10 mL ethyl acetate and the combined organic extracts were washed with 10 mL brine, dried (MgSO$_4$) and the solvent was removed in vacuo. The residue was purified by column chromatography (silica) eluting with dichloromethane/methanol/aq. ammonia 99/1/0.1, increasing polarity to 95/5/0.5. This gave the title compound (16 mg, 27%) as a yellow gum. $^1$H NMR (CD$_3$OD, 400 MHz) δ 0.20-0.37 (6H, 4×d), 0.91-1.13, 1.67-1.76 and 1.94-2.09 (2H, 3×m), 2.54-2.62 (1H, m), 2.87-2.93 and 2.99-3.05 (1H, 2×m), 3.61-3.74 (3H, m), 3.86-4.08 (4H, m), 4.20-4.26 (1H, m), 6.83-6.88 (1H, m), 7.11-7.44 (4H, m), 7.63-7.78 (2H, m), 8.30-8.46 (3H, m); LRMS (EI+) 493 [MH+].

Example 10

6-[(3S,4S)-3-(5-chloropyridin-2-yl)-4-{[3R,4R,5S)-4-(5-chloropyridin-2-yl)-4-hydroxy-3,5-dimethylpiperidin-1-yl]carbonyl}pyrrolidin-1-yl]-2-methylpyridazin-3(2H)-one

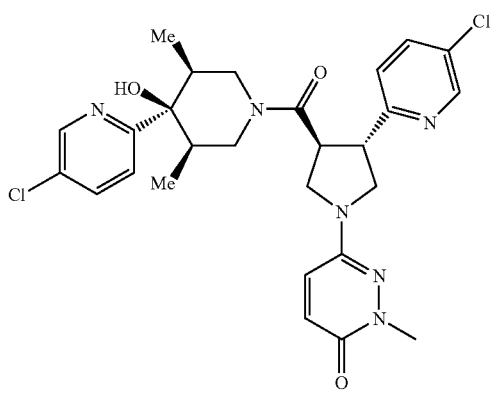

To a solution of the carboxylic acid from preparation 15 (42 mg, 0.08 mmol) in dichloromethane (3 mL) was added N-ethyldiisopropylamine (0.04 mL, 0.25 mmol), 1-hydroxybenzotriazole (15 mg, 0.095 mmol) and 1-(3-dimethylaminopropyl)-3-ethylcarbodiimide and the mixture was stirred under nitrogen for 30 minutes. The amine from preparation 16 was added and the mixture was stirred under nitrogen overnight. The reaction mixture was diluted with dichloromethane (20 mL) and washed with saturated $NaHCO_3$ (20 mL) and brine (20 mL). The organic layer was dried over $MgSO_4$, filtered and evaporated to give a yellow oily solid. This was purified by column chromatography (silica), eluting with dichloromethane and increasing the polarity to 95/5 dichloromethane/methanol to yield the title compound as yellow solid (31 mg, 67%). $^1$H NMR ($CD_3OD$, 400 MHz) δ0.36-0.6 (m, 6H), 1.18 (br, 1H), 1.89 (br, 1H), 2.16 (br, 1H), 2.71 (m, 1H), 3.13 (m, 1H), 3.6-4.2 (s+m, 9H), 4.33 (d, 1H), 6.89 (d, 1H), 7.2-7.5 (m, 3H), 7.78-7.92 (m, 2H), 8.56 (d, 2H); LRMS (EI$^+$) 558 [MH$^+$].

Examples 11-46

Examples 11-46 were prepared according to the methods described above for examples 1-10, starting from the appropriate pyridine aldehyde[1] and the appropriate 4 substituted 3,5-dimethylpiperidin-4-ol.[2]

1. 2-Methoxypyridine-5-carbaldehyde is commercially available. Other aldehydes are described in preparations 2, 17, 18 and 22.
2. (3R,4s,5S)-4-(5-Chloropyridin-2-yl)-3,5-dimethylpiperidin-4-ol is described in preparation 16. The syntheses of the other required piperidinols are described in international patent application publication number WO 2005/077935.

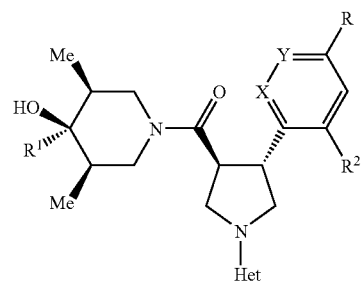

| Example | X | Y | R | R$^1$ | R$^2$ | Het | Data |
|---|---|---|---|---|---|---|---|
| 11 | CH | N | —OMe | 4-F-phenyl | H | pyridazinyl | LRMS (APCl+) 506 [MH+] |
| 12 | CH | N | —OMe | phenyl | H | pyridazinyl | LRMS (EI+) 488 [MH+] |
| 13 | CH | N | —OMe | 4-F-phenyl | H | 5-F-pyridin-3-yl | LRMS (EI+) 523 [MH+] |

-continued
I
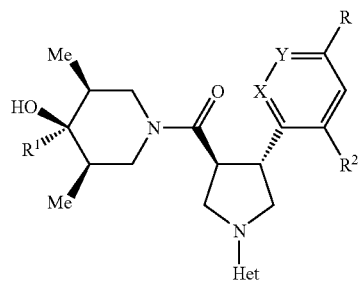
| Example | X | Y | R | R¹ | R² | Het | Data |
|---|---|---|---|---|---|---|---|
| 14 | CH | N | —OMe | 4-F-phenyl | H | 6-cyanopyridin-3-yl | LRMS (EI+) 530 [MH+] |
| 15 | CH | N | —OMe | 4-F-phenyl | H | 5-cyanopyridin-3-yl | LRMS (EI+) 530 [MH+] |
| 16 | CH | N | —OMe | 4-F-phenyl | H | 6-cyanopyridazin-3-yl | LRMS (APCI+) 531 [MH+] |
| 17 | N | CH | Cl | cyclohexyl | H | 1-methyl-6-oxopyridazin-3-yl | LRMS (APCI+) 528 [MH+] |
| 18 | N | CH | Cl | cyclopropyl | H | 1-methyl-6-oxopyridazin-3-yl | LRMS (APCI+) 486 [MH+] |
| 19 | N | CH | Cl | 3,4-difluorophenyl | H | 1-methyl-6-oxopyridazin-3-yl | LRMS (APCI+) 558 [MH+] |

-continued

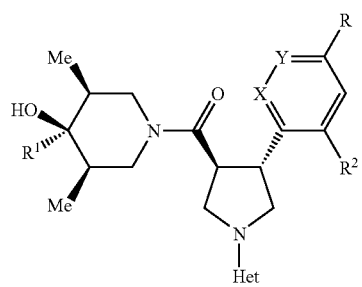

I

| Example | X | Y | R | R¹ | R² | Het | Data |
|---|---|---|---|---|---|---|---|
| 20 | N | CH | Cl | MeO-C₆H₄- | H | 6-(1-methyl-6-oxo-1,6-dihydropyridazin-3-yl) | LRMS (APCl+) 552 [MH+] |
| 21 | N | CH | Cl | C₆H₅- | H | 6-(1-methyl-6-oxo-1,6-dihydropyridazin-3-yl) | LRMS (APCl+) 522 [MH+] |
| 22 | N | CH | Cl | 2-pyridyl | H | 6-(1-methyl-6-oxo-1,6-dihydropyridazin-3-yl) | LRMS (EI+) 523 [MH+] |
| 23 | N | CH | Cl | 4-Cl-C₆H₄- | H | 6-(1-methyl-6-oxo-1,6-dihydropyridazin-3-yl) | LRMS (APCl+) 556 [MH+] |
| 24 | N | CH | Cl | cyclopropyl | H | 3-fluoro-5-pyridyl | LRMS (APCl+) 473 [MH+] |
| 25 | N | CH | Cl | 4-F-C₆H₄- | H | 3-fluoro-5-pyridyl | LRMS (APCl+) 527 [MH+] |

-continued
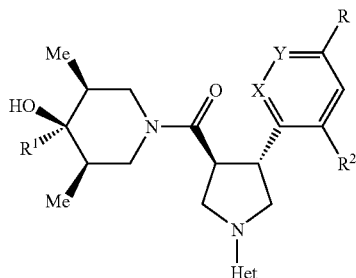
I
| Example | X | Y | R | R¹ | R² | Het | Data |
|---|---|---|---|---|---|---|---|
| 26 | N | CH | Cl | cyclopropyl | H | 3-methoxy-pyridazin-6-yl | LRMS (APCl+) 486 [MH+] |
| 27 | N | CH | Cl | phenyl | H | 6-oxo-1,6-dihydropyridazin-3-yl | LRMS (APCl+) 508 [MH+] |
| 28 | N | CH | Cl | pyridin-2-yl | H | 6-oxo-1,6-dihydropyridazin-3-yl | LRMS (EI+) 509 [MH+] |
| 29 | N | CH | Cl | phenyl | H | 6-cyanopyridazin-3-yl | LRMS (APCl+) 517 [MH+] |
| 30 | N | CH | Cl | pyridin-2-yl | H | 6-cyanopyridazin-3-yl | LRMS (EI+) 518 [MH+] |
| 31 | N | CH | Cl | pyridin-2-yl | H | 6-chloropyridazin-3-yl | LRMS (EI+) 527 [MH+] |

-continued
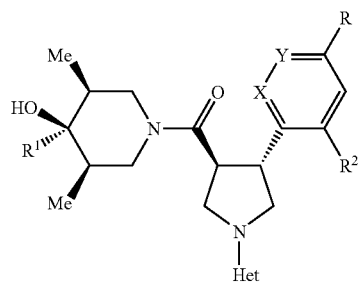
I
| Example | X | Y | R | R¹ | R² | Het | Data |
|---|---|---|---|---|---|---|---|
| 32 | N | CH | F | 4-Cl-phenyl | H | 6-cyanopyridazin-3-yl | LRMS (EI+) 535 [MH+] |
| 33 | N | CH | F | phenyl | H | 6-cyanopyridazin-3-yl | LRMS (EI+) 501 [MH+] |
| 34 | N | CH | F | 4-F-phenyl | H | 6-cyanopyridazin-3-yl | LRMS (EI+) 519 [MH+] |
| 35 | N | CH | F | phenyl | H | 6-chloropyridazin-3-yl | LRMS (EI+) 510 [MH+] |
| 36 | N | CH | F | 4-F-phenyl | H | 6-chloropyridazin-3-yl | LRMS (EI+) 528 [MH+] |
| 37 | N | CH | F | phenyl | H | 6-oxo-1,6-dihydropyridazin-3-yl | LRMS (EI+) 492 [MH+] |

-continued
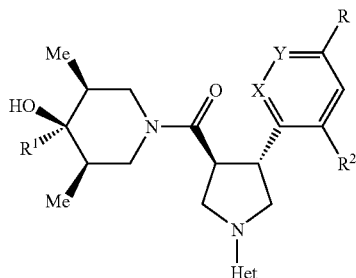
| Example | X | Y | R | R¹ | R² | Het | Data |
|---|---|---|---|---|---|---|---|
| 38 | N | CH | F | 4-F-C₆H₄ | H | 6-oxo-1H-pyridazin-3-yl | LRMS (EI+) 510 [MH+] |
| 39 | N | CH | F | Ph | H | 1-Me-6-oxo-pyridazin-3-yl | LRMS (EI+) 506 [MH+] |
| 40 | N | CH | F | 4-F-C₆H₄ | H | 1-Me-6-oxo-pyridazin-3-yl | LRMS (EI+) 524 [MH+] |
| 41 | N | CH | —OMe | 5-Cl-pyridin-2-yl | H | 6-oxo-1H-pyridazin-3-yl | LRMS (EI+) 539 [MH+] |
| 42 | N | CH | —OMe | 4-F-C₆H₄ | H | 6-oxo-1H-pyridazin-3-yl | LRMS (APCI+) 522 [MH+] |
| 43 | N | CH | —OMe | 4-F-C₆H₄ | H | 6-CN-pyridazin-3-yl | LRMS (APCI+) 531 [MH+] |

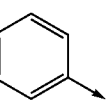

| Example | X | Y | R | R¹ | R² | Het | Data |
|---|---|---|---|---|---|---|---|
| 44 | N | CH | —OMe | 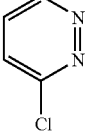 | H | 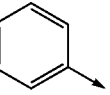 | LRMS (APCI⁺) 540 [MH⁺] |
| 45 | N | CH | —CN | 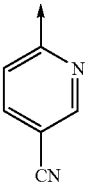 | H | 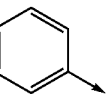 | LRMS (APCl+) 525 [MH+] |
| 46 | N | CH | —CN |  | H | 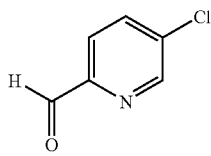 | LRMS (APCl+) 526 [MH+] |

PREPARATIONS

Preparation 1

5-Chloro-2-iodopyridine

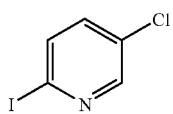

Acetyl chloride (11.05 mL, 0.155 mol) was added to a solution of 2-bromo-5-chloropyridine (20.0 g, 0.103 mol) in acetonitrile (120 mL) followed by sodium iodide (23.3 g, 0.155 mol) and the mixture was heated at reflux with a drying tube fitted for 3 hours. The reaction was cooled in an ice bath, carefully basified with saturated aqueous potassium carbonate then extracted with ethyl acetate (2×100 mL). The combined organic layers were washed with saturated aqueous sodium sulfite (200 mL), dried (MgSO₄) and evaporated. The residue was then re-submitted to identical reaction and work-up conditions in order to ensure complete reaction and this gave the title compound (18.71 g, 75%) as a brown solid. ¹H NMR (CDCl₃, 400 MHz) δ 7.30 (1H, dd), 7.65 (1H, d), 8.35 (1H, d); LRMS (APCI⁺) 240 [MH⁺].

Preparation 2

5-Chloropyridine-2-carbaldehyde

The iodide from preparation 2 (18.71 g, 78.1 mmol) was dissolved in tetrahydrofuran (100 mL) and cooled to −15° C. under nitrogen. A solution of isopropyl magnesium chloride in tetrahydrofuran (2M, 42.2 mL, 84.4 mmol) was then added dropwise, ensuring that the temperature stayed below 0° C. The reaction mixture was cooled to −15° C., stirred for 1 hour and dimethylformamide (9.0 mL, 116 mmol) was added dropwise, maintaining the temperature below 0° C. The reaction mixture was allowed to warm to room temperature and stirred for 1 hour before being re-cooled to 0° C. and carefully quenched by the dropwise addition of 2M HCl (100 mL). After the addition was complete the mixture was stirred at room temperature for 30 min before the pH was adjusted to 6-7 by the addition of saturated aqueous sodium hydrogen carbonate. The organic layer was separated and the aqueous layer was extracted with dichloromethane (2×200 mL). The combined organic layers were washed with water (200 mL), dried (MgSO$_4$) and concentrated on a rotary evaporator, keeping the temperature below 30° C., to give crude product (13.7 g) as a brown oil which was used without further purification. $^1$H NMR (CDCl$_3$, 400 MHz) δ 7.35 (1H, d), 7.95 (1H, d), 8.73 (1H, s), 10.02 (1H, s); LRMS (APCI$^+$) 142 [MH$^+$].

Preparation 3 tert-Butyl(2E)-3-(5-chloropyridin-2-yl)acrylate

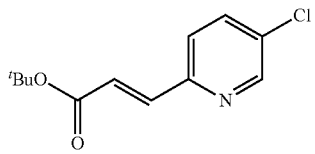

n-Butyl lithium (2.5 M in hexanes, 34 mL, 85 mmol) was added dropwise to a solution of tert-butyl diethylphosphonoacetate (19.1 mL, 81 mmol) in diethyl ether (80 mL) at −78° C. under nitrogen and stirring was continued for 30 min. A solution of the crude aldehyde from preparation 2 (from 78.1 mmol of the iodide of preparation 1) in diethyl ether (20 mL) was then added dropwise, keeping the temperature below −65° C. Once the addition was complete the mixture was allowed to warm to room temperature over 2 hours before being cautiously quenched by the addition of saturated aqueous ammonium chloride (200 mL). The mixture was extracted with diethyl ether (2×150 mL) and the combined organic extracts were washed with brine (200 mL), dried (MgSO$_4$) and evaporated. The residue was purified by column chromatography (silica), eluting with pentane increasing polarity to pentane/ethyl acetate 8:2, to give the title compound (13.34 g, 74% over 2 steps) as an oil. $^1$H NMR (CDCl$_3$, 400 MHz) δ 1.51, (9H, s), 6.79 (1H, d), 7.35 (1H, d), 7.52, (1H, d), 7.66 (1H, dd), 8.55 (1H, d); LRMS (APCI$^+$) 240 [MH$^+$].

Preparation 4

(2E)-3-(5-Chloropyridin-2-yl)acrylic acid trifluoroacetic acid salt

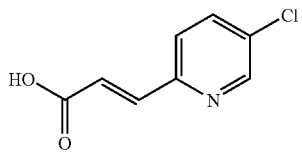

A solution of trifluoroacetic acid (10 mL) in dichloromethane (10 mL) was added dropwise to an ice cooled solution of the ester from preparation 3 (2.09 g, 8.7 mmol) in dichloromethane (10 mL) and the resulting mixture was stirred at room temperature overnight. The solvent was removed in vacuo, toluene (10 mL) was added and removed in vacuo and dichloromethane (10 mL) was added and removed in vacuo to give the title compound (2.44 g, 94%) as a red solid. $^1$H NMR (CD$_3$OD, 400 MHz) δ 6.86 (1H, d), 7.64 (2H, m), 7.87 (1H, dd), 8.59 (1H, d); LRMS (APCI$^+$) 184 [MH$^+$].

Preparation 5

(4S)-4-Benzyl-3-[(2E)-3-(5-chloropyridin-2-yl)prop-2-enoyl]-1,3-oxazolidin-2-one

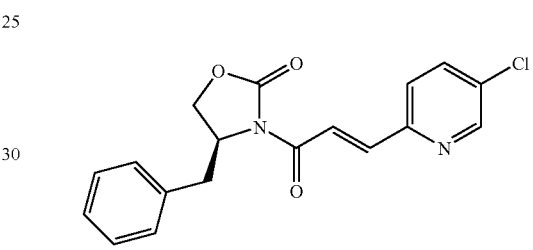

A solution of the acid from preparation 4 (2.44 g, 8.2 mmol) in tetrahydrofuran (15 mL) was cooled to −78° C. under nitrogen. Triethylamine (2.85 mL, 20 mmol) was added dropwise followed by trimethylacetyl chloride (1.11 mL, 9.0 mmol), controlling the rate of addition so that the temperature stayed below −65° C. The mixture was then stirred at −78° C. for 2 hours. $^n$BuLi (2.5 M in hexanes, 4.26 mL, 10.7 mmol) was added dropwise to a solution of (4S)-4-benzyl-1,3-oxazolidin-2-one (1.74 g, 9.8 mmol) in tetrahydrofuran (15 mL) under nitrogen at −78° C., controlling the rate of addition so that the temperature stayed below −65° C. After stirring at −78° C. for 20 minutes the solution of oxazolidinone anion was added via cannula to the mixed anhydride solution at −78° C. The reaction mixture was stirred at −78° C. for 20 minutes then allowed to warm slowly to room temperature overnight. The reaction was quenched by the addition of saturated aqueous ammonium chloride solution (30 mL) and then concentrated in vacuo to remove the tetrahydrofuran. The solid precipitate was filtered and washed with diethyl ether to give the title compound (1.52 g, 54%) as a buff solid. The ether washings were evaporated to dryness, slurried in diethyl ether and filtered to give further product (0.42 g, 15%). $^1$H NMR (CDCl$_3$, 400 MHz) δ 2.84 (1H, t), 3.37 (1H, d), 4.22 (2H, m), 4.78 (1H, m), 7.2-7.4 (5H, m), 7.51 (1H, d), 7.69 (1H, d), 7.86 (1H, d), 8.23 (1H, d), 8.62 (1H, s); LRMS (APCI$^+$) 343 [MH$^+$].

Preparation 6

(4S)-4-Benzyl-3-{[(3S,4S)-1-benzyl-4-(5-chloropyridin-2-yl)pyrrolidin-3-yl]carbonyl}-1,3-oxazolidin-2-one

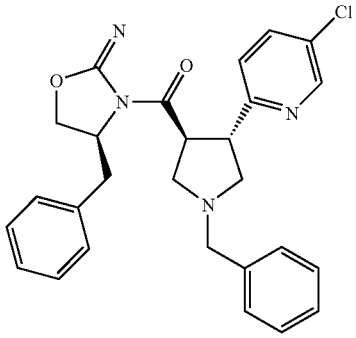

Trifluoroacetic acid (90 μL, 1.2 mmol) was added to a suspension of the oxazolidinone from preparation 5 (1.93 g, 5.6 mmol) in dichloromethane (20 mL) and N-benzyl-N-(methoxymethyl)trimethylsilylamine (2.3 mL, 9.0 mmol) was then added dropwise over 10 minutes. After the addition was complete the reaction was allowed to stir at room temperature overnight. The reaction mixture was treated with saturated aqueous sodium hydrogen carbonate solution (20 mL) and the layers were separated. The aqueous layer was extracted with dichloromethane (2×20 mL) and the combined organic layers were dried (MgSO₄) and evaporated. The residue was purified by column chromatography (silica), eluting with ethyl acetate/pentane 2:8, increasing polarity to 2:3 to give the undesired (4S)-4-benzyl-3-{[(3R,4R)-1-benzyl-4-(5-chloropyridin-2-yl)pyrrolidin-3-yl]carbonyl}-1,3-oxazolidin-2-one (1.16 g, 44%) as the first eluting component and the desired (4S)-4-benzyl-3-{[(3S,4S)-1-benzyl-4-(5-chloropyridin-2-yl)pyrrolidin-3-yl]carbonyl}-1,3-oxazolidin-2-one (1.18 g, 45%) as the second eluting component. ¹H NMR (CDCl₃, 400 MHz) δ 2.75 (2H, m), 2.92 (1H, m), 3.20 (3H, m), 3.27 (1H, br), 3.68 (2H, br), 4.14 (2H, m), 4.23 (1H, m), 4.50 (1H, m), 4.67 (1H, m), 7.10-7.40 (11H, m), 7.58 (1H, dd), 8.50 (1H, d); LRMS (APCI⁺) 476 [MH⁺].

Preparation 7

Methyl (3S,4S)-1-benzyl-4-(5-chloropyridin-2-yl)pyrrolidine-3-carboxylate

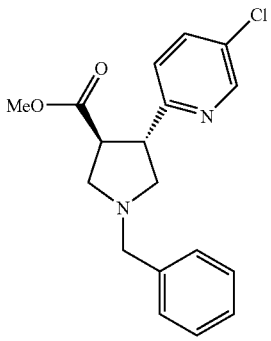

Sodium methoxide (664 mg, 12 mmol) was added to a solution of the oxazolidinone from preparation 6 (1.17 g, 2.5 mmol) and dimethyl carbonate (1.03 mL, 12 mmol) in dichloromethane (15 mL) and the reaction was stirred at room temperature overnight. The reaction mixture was concentrated in vacuo and the residue was partitioned between ethyl acetate (50 mL) and water (30 mL). The aqueous layer was neutralised by the addition of 2M HCl (~6 mL) and then concentrated in vacuo. The residue was triturated with acetonitrile (25 mL) and then filtered. Concentration of the filtrate gave (3S,4S)-1-benzyl-4-(5-chloropyridin-2-yl)pyrrolidine-3-carboxylic acid (123 mg, 16%) as yellow solid (see preparation 8 for spectroscopic data). The ethyl acetate layer was dried (MgSO₄) and evaporated. Purification of the residue by column chromatography (silica), eluting with ethyl acetate/pentane 2:8, increasing polarity to 2:3 gave the title compound (371 mg, 45%) as a colourless oil. ¹H NMR (CDCl₃, 400 MHz) δ2.71 (1H, t), 2.97 (1H, t), 3.05 (2H, m), 3.23 (1H, m), 3.63 (5H, m), 3.82 (1H, q), 7.15-7.35 (6H, m), 7.55 (1H, d), 8.46 (1H, s); LRMS (APCI⁺) 331 [MH⁺].

Preparation 8

(3S,4S)-1-Benzyl-4-(5-chloropyridin-2-yl)pyrrolidine-3-carboxylic acid bis hydrochloride

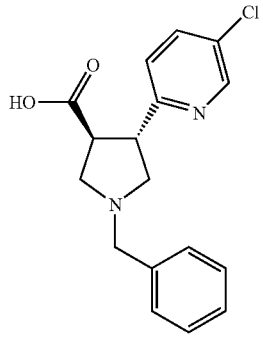

A solution of NaOH (135 mg, 3.3 mmol) in water (5 mL) was added to a solution of the ester from preparation 7 (371 mg, 1.1 mmol) in dioxane (10 mL) and the mixture was stirred at room temperature overnight. The reaction mixture was concentrated in vacuo, taken up in water (10 mL) and neutralised with 2M HCl (~1.7 mL). The mixture was then concentrated in vacuo, triturated with acetonitrile (20 mL) and filtered. The filtrate was acidified with 2M ethereal HCl and concentrated in vacuo to give the title compound (290 mg, 68%) as a solid. ¹H NMR (CD₃OD, 400 MHz) δ3.40-4.20 (6H, m), 4.53 (2H, m), 7.40-7.60 (6H, m), 7.81 (1H, d), 8.60 (1H, br); LRMS (APCI⁺) 317 [MH⁺].

Preparation 9

(3R,4R,5S)-1-{[(3S,4S)-1-Benzyl-4-(5-chloropyridin-2-yl)pyrrolidin-3-yl]carbonyl}-4-(4-fluorophenyl)-3,5-dimethylpiperidin-4-ol

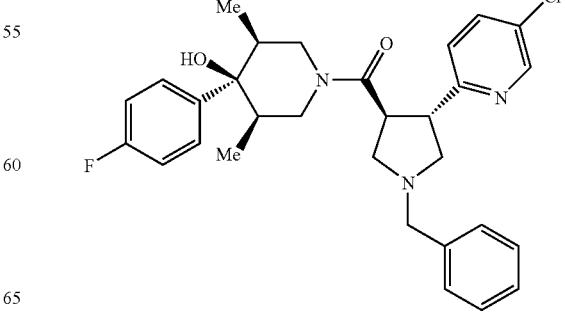

1-Hydroxybenzotriazole (230 mg, 1.7 mmol) and 1-(3-dimethylaminopropyl)-3-ethyl-carbodiimide hydrochloride (354 mg, 1.8 mmol) were added to a solution of the acid from preparation 8 (522 mg, 1.5 mmol) in dichloromethane (10 mL) and triethylamine (1.03 mL, 7.4 mmol) and the mixture was stirred at room temperature for 30 minutes before the addition of (3R,4s,5S)-4-(4-fluorophenyl)-3,5-dimethylpiperidin-4-ol hydrochloride (prepared according to US 2005/176772) (384 mg, 1.5 mmol). The mixture was stirred at room temperature overnight, the solvent was removed in vacuo and the residue was partitioned between ethyl acetate (50 mL) and saturated aqueous sodium hydrogen carbonate (50 mL). The organic layer was washed with brine (50 mL), dried (MgSO$_4$) and evaporated. The residue was purified by column chromatography (silica), eluting with dichloromethane, increasing polarity to 5% methanol in dichloromethane, to give the title compound (546 mg, 71%) as an oil. $^1$H NMR (CD$_3$OD, 400 MHz) δ 0.3-0.6 (6H, 4×d), 1.23 (1H, m), 1.75-1.95 (2H, m), 2.72 (1H, t), 2.85 (1H, m), 2.90-3.20 (3H, m), 3.45-4.05 (5H, m), 4.32 (1H, d), 7.02 (3H, m), 7.20-7.50 (7H, m), 7.80, (1H, dd), 8.50 (1H, d); LRMS (APCI$^+$) 522 [MH$^+$].

Preparation 10

(3R,4R,5S)-1-{[(3S,4S)-4-(5-Chloropyridin-2-yl)pyrrolidin-3-yl]carbonyl}-4-(4-fluorophenyl)-3,5-dimethylpiperidin-4-ol

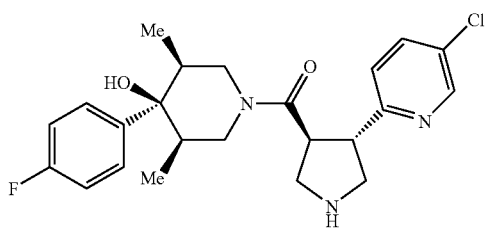

1-Chloroethyl chloroformate (0.3 mL, 2.8 mmol) was added to a solution of the amide from preparation 9 (370 mg, 0.7 mmol) and N-ethyldiisopropylamine (0.27 mL, 1.6 mmol) in dichloromethane (10 mL) and the mixture was heated at reflux for 3 hours. After cooling to room temperature the solvent was removed in vacuo and the residue was partitioned between 10% aqueous citric acid (30 mL) and dichloromethane (30 mL). The organic layer was washed with water (30 mL), dried (MgSO$_4$) and evaporated. The resulting dark oil was taken up in methanol (10 mL) and heated at reflux for 3 hours. The solvent was removed in vacuo and the residue was purified by column chromatography (silica) eluting with 5% methanol in dichloromethane, increasing polarity to 10% methanol in dichloromethane, to give the title compound (305 mg, 100%) as an oil. $^1$H NMR (CD$_3$OD, 400 MHz) δ 0.4-0.6 (6H, 4×d), 1.00-1.06, 1.77-1.82 and 1.98-2.05 (2H, 3×m), 2.76-2.82 (1H, m), 3.00-3.20 (2H, m), 3.40-4.10 (6H, m), 4.36 (1H, m) 7.00-7.50 (5H, m), 7.85 and 7.95 (1H, 2×dd), 8.61 and 8.63 (1H, 2×d); LRMS (APCI$^+$) 432 [MH$^+$].

Preparation 11

Methyl (3S,4S)-4-(5-chloropyridin-2-yl)pyrrolidine-3-carboxylate

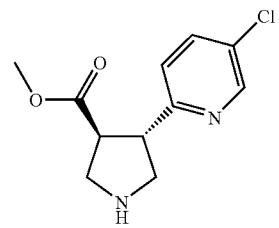

1-Chloroethyl chloroformate (2.33 mL, 21.4 mmol) was added to a solution of the ester from preparation 7 (1.77 g, 5.35 mmol) and N-ethyldiisopropylamine (2.1 mL, 12 mmol) in dichloromethane (10 mL) and the mixture was heated at reflux for 3 hours. After cooling to room temperature the solvent was removed in vacuo and the residue was taken up in methanol (10 mL) and heated at reflux for 16 hours. The solvent was removed in vacuo and the residue was purified by column chromatography (silica) eluting with dichloromethane, increasing polarity to 10% methanol in dichloromethane, to give a mixture of the desired product and N-ethyldiisopropylamine as an oil. The oil was taken up in ethyl acetate (30 mL) and the resulting precipitate was filtered. The filtrate was concentrated in vacuo and the residue was taken up in acetonitrile (25 mL). The resulting precipitate was filtered to give the title compound (619 mg, 48%) as a white solid. $^1$H NMR (CD$_3$OD, 400 MHz) δ 3.46 (m, 1H), 3.61-3.77 (m, 7H), 3.74 (s, 3H), 3.98 (m, 1H), 7.42 (d, 1H), 7.82 (dd, 1H), 8.57 (d, 1H); LRMS (APCI$^+$) 241 [MH$^+$].

Preparation 12

Methyl (3S,4S)-1-(6-chloropyridazin-3-yl)-4-(5-chloropyridin-2-yl)pyrrolidine-3-carboxylate

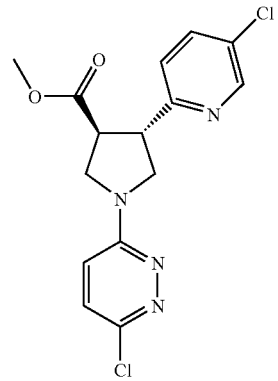

To a solution of the pyrrolidine from preparation 11 (350 mg, 1.50 mmol) in dimethylsulfoxide (10 mL) was added 3,6-dichloropyridazine (330 mg, 2.20 mmol), triethylamine (0.61 mL, 4.40 mmol), and caesium fluoride (220 mg, 1.45 mmol). The mixture was stirred at 80° C. under nitrogen overnight. The reaction mixture was taken up in 25 mL ethyl acetate and washed with 20 mL of water. The organic layer was separated and the aqueous layer was re-extracted with a further 25 mL of ethyl acetate. The combined ethyl acetate extracts were dried over MgSO$_4$, filtered and evaporated to give a pale orange oily solid which was purified by column chromatography, eluting with dichloromethane increasing polarity to 95/5 dichloromethane/methanol. This yielded the title compound as a yellow solid. ¹H NMR (CD₃OD, 400 MHz) δ 3.66 (s, 1H), 3.72 (m, 1H), 3.78 (t, 1H), 3.96-4.12 (m, 4H), 7.04 (d, 1H), 7.42 (m, 2H), 7.79 (d, 1H), 8.52 (s, 1H); LRMS (EI⁺) 353 [MH⁺].

Preparation 13

Methyl (3S,4S)-4-(5-chloropyridin-2-yl)-1-(6-oxo-1,6-dihydropyridazin-3-yl)pyrrolidine-3-carboxylate

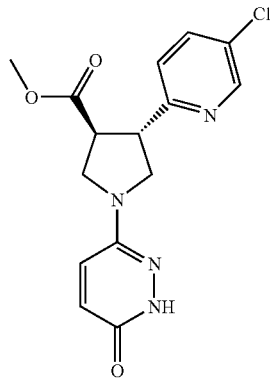

A solution of chloropyridazine from preparation 12 (803 mg, 2.27 mmol) was dissolved in deoxygenated acetic acid and heated at reflux under nitrogen for 44 hours. The solvent was removed in vacuo and 15 mL methanol was added. HCl gas was then bubbled through the reaction mixture until it was saturated and the mixture was stirred under a drying tube overnight. The methanol was removed in vacuo and the residue was partitioned between DCM and 10% K₂CO₃. The organic layer was separated, dried over MgSO₄, filtered and evaporated to yield the title compound as a pale brown solid (577 mg, 76%). ¹H NMR (CD₃OD, 400 MHz) δ 3.58-3.76 and 3.83-3.97 (6H, 2×m), 3.65 (3H, s), 6.89 (1H, d), 7.31 (1H, d), 7.39 (1H, d), 7.79 (1H, dd), 8.52 (1H, d); LRMS (EI⁺) 335 [MH⁺].

Preparation 14

Methyl (3S,4S)-4-(5-chloropyridin-2-yl)-1-(1-methyl-6-oxo-1,6-dihydropyridazin-3-yl)pyrrolidine-3-carboxylate

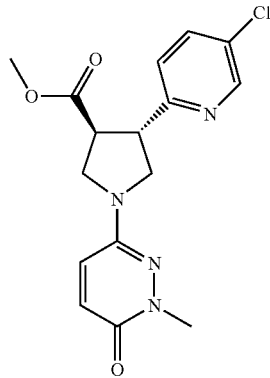

To a solution of the pyridazinone from preparation 13 (557 mg, 1.66 mmol) in dimethylformamide (10 mL) was added sodium hexamethydisilazide (1M in tetrahydrofuran, 2.00 mL, 2.00 mmol) and lithium bromide (173 mg, 2.00 mmol). The reaction was stirred under nitrogen for 10 minutes before iodomethane (0.083 mL, 1.30 mmol) was added. The reaction was stirred under nitrogen for 4 hours and then partitioned between ethyl acetate (30 mL) and water (30 mL). The organic layer was separated, dried over MgSO₄, filtered and evaporated to give a brown oil which was purified using column chromatography (silica), eluting with 100% dichloromethane, increasing polarity to 95/5 dichloromethane/methanol. This yielded the title compound as a yellow oil (500 mg, 90%). ¹H NMR (CD₃OD, 400 MHz) δ 3.64 (m, 9H), 3.92 (m, 3H), 6.87 (d, 1H), 7.26 (d, 1H), 7.37 (d, 1H), 7.79 (dd, 1H), 8.51 (s, 1H); LRMS (EI⁺) 349 [MH⁺].

Preparation 15

(3S,4S)-4-(5-Chloropyridin-2-yl)-1-(1-methyl-6-oxo-1,6-dihydropyridazin-3-yl)pyrrolidine-3-carboxylic acid

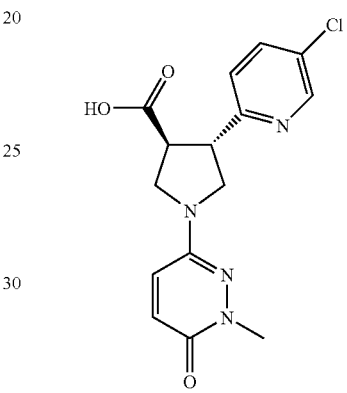

To a solution of the ester from preparation 14 (500 mg, 1.43 mmol) in dioxane (10 mL) was added sodium hydroxide (172 mg, 4.30 mmol) as a solution in 5 mL of water. The reaction was stirred under a drying tube overnight. The solvent was removed in vacuo, the residue was taken up in water, neutralised with 4 equiv. of 2M HCl and evaporated. The residue was stirred with 20 mL of acetonitrile and filtered to give a buff solid (512 mg containing 3 equiv. NaCl–338 mg product+174 mg NaCl). ¹H NMR (CD₃OD, 400 MHz) δ 3.6 (m, 2H), 3.64 (s, 3H), 3.7 (t, 1H), 3.9 (m, 3H), 6.88 (d, 1H), 7.27 (d, 1H), 7.41 (d, 1H), 7.79 (dd, 1H), 8.52 (s, 1H); LRMS (EI⁺) 335 [MH⁺].

Preparation 16

(3R,4s,5S)-4-(5-chloropyridin-2-yl)-3,5-dimethylpiperidin-4-ol

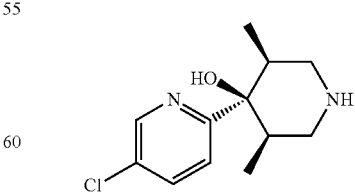

Step A: (3R,4s,5S)-4-(5-chloropyridin-2-yl)-1-(4-methoxybenzyl)-3,5-dimethylpiperidin-4-ol A solution of 2-bromo-5-chloropyridine (6.0 g, 31.2 mmol) in toluene (90 mL) was cooled to −78° C. under nitrogen. n-Butyllithium (2.5M in hexanes) (15 mL, 37.5 mmol) was added dropwise over 12 minutes and the mixture was stirred at −78° C. for 1 hour. A solution of (3R,5S)-1-(4-methoxybenzyl)-3,5-dimethylpiperidin-4-one (prepared according to international patent application publication number WO 2005/077935) (6.93 g, 28.1 mmol) in toluene (15 mL) was then added dropwise over 10 minutes and the mixture was stirred at −78° C. for a further 3 hours before being allowed to warm to room temperature. The mixture was quenched by pouring into saturated ammonium chloride (100 mL) and, after stirring for 5 minutes, the mixture was partitioned between water (50 mL) and ethyl acetate (300 mL). The organic phase was separated and the aqueous phase was extracted with further ethyl acetate (2×300 mL). The combined organic extracts were dried over magnesium sulfate, filtered and then evaporated to dryness to give the crude intermediate. Purification by column chromatography (silica) eluting with 2% methanol in dichloromethane, increasing polarity to 10% (10:1 methanol:880 ammonia) in dichloromethane, gave (3R,4s,5S)-4-(5-chloropyridin-2-yl)-1-(4-methoxybenzyl)-3,5-dimethylpiperidin-4-ol as an orange oil (8.48 g, 83%).

Step B: (3R,4s,5S)-4-(5-chloropyridin-2-yl)-3,5-dimethylpiperidin-4-ol

The product from step A (6.56 g, 18.2 mmol) was dissolved in dry dichloromethane (100 mL), triethylamine (2.02 g, 20.0 mmol) was added and the solution was cooled to 5° C. under nitrogen. 1-Chloroethylchloroformate (3.1 g, 21.9 mmol) was added dropwise to the stirred solution and on completion of addition the mixture was stirred for a further 2.5 hours at room temperature. The mixture was then washed with 10% aqueous potassium carbonate solution (3×50 mL) dried over magnesium sulfate and evaporated to dryness. The crude oil was heated under reflux in methanol (100 mL) for 2.5 hours and the solvent was removed in vacuo. The residue was dissolved in dichloromethane (100 mL) and methanol (10 mL), solid potassium carbonate (10 g) was added and the heterogeneous mixture was stirred for 30 minutes. The solid potassium carbonate was filtered off and the filtrate was evaporated to dryness. The crude product was then purified by column chromatography (silica) eluting with 10% methanol in dichloromethane, increasing polarity to 20% (10:1 methanol:880 ammonia) in dichloromethane, to give the title compound (3.37 g, 77%) as a yellowish solid. $^1$H NMR (400 MHz, CDCl$_3$) δ 0.53 (3H, s), 0.57 (s, 3H), 2.60-2.71 (m, 2H), 3.13 (q, 2H), 3.32 (d, 2H), 7.43 (d, 1H), 7.78 (dd, 1H), 8.50 (1H, d), 9.58 (br, 1H), 9.84 (br, 1H); LRMS (APCI+) 241 and 243 [MH$^+$].

Preparation 17

5-Fluoropyridine-2-carbaldehyde

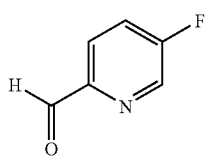

The title compound was prepared according to the methods of preparations 1 and 2, starting from 2-bromo-5-fluoropyridine. This gave crude material containing tetrahydrofuran and diethyl ether which was used without further purification. $^1$H NMR (CDCl$_3$, 400 MHz) δ 7.57 (1H, dt), 8.03 (1H, dd), 8.62 (1H, d), 10.04 (1H, s); LRMS (APCI$^+$) 126 [MH$^+$].

Preparation 18

6-Formylnicotinonitrile

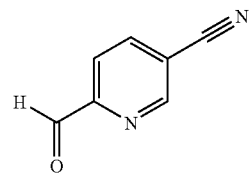

A mixture of 6-methylnicotinonitrile (10.0 g, 84.6 mmol) and iodine (20.0 g, 78.8 mmol) in dimethylsulfoxide (150 mL) was heated at 150° C. under nitrogen for 20 minutes (reaction exhaust was scrubbed with bleach to remove dimethyl sulfide). After cooling to room temperature saturated aqueous sodium bicarbonate (200 mL) was added carefully and the resulting mixture was extracted with toluene (3×100 mL). The combined organic extracts were washed with brine, dried (MgSO$_4$) and evaporated to give the desired product as an orange oil (5.65 g, 50%) which was used without further purification. $^1$H NMR (CDCl$_3$, 400 MHz) δ 8.06 (1H, d), 8.17 (1H, dd), 9.05 (1H, d), 10.12 (1H, s).

Preparation 19

5-Methoxy-2-methylpyridine

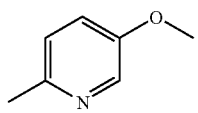

6-methylpyridin-3-ol (50.0 g, 0.458 mol) was added to a suspension of powdered KOH (103 g, 1.83 mol) in dimethylsulfoxide (750 mL) and the mixture was left to stir at room temperature under nitrogen for 1.5 hours. Methyl iodide (30 mL, 68.3 g, 0.481 mol) was then added dropwise over 1 hour to the dark brown mixture (exothermic). After stirring at room temperature for 1.5 hours water (1.0 L) was added and the mixture was extracted with ethyl acetate (2×300 mL). The combined organic extracts were washed with brine, dried (MgSO$_4$) and evaporated at 40° C. on a rotary evaporator. The residue was purified by column chromatography (silica), eluting with pentane, increasing polarity to ethyl acetate, to give the volatile product as a ~1:1 mixture with ethyl acetate (40 g, ~23.3 g product, 41%). ¹H NMR (CDCl₃, 400 MHz) δ 2.45 (3H, s), 3.79 (3H, s), 7.02 (1H, d), 7.08 (1H, dd), 8.16 (1H, d).

Preparation 20

5-Methoxy-2-methylpyridine 1-oxide

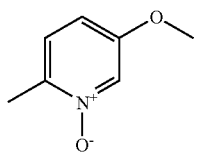

m-Chloroperbenzoic acid (51.3 g, 0.297 mol) was added portionwise to a solution of the compound of preparation 19 (40 g of a 1:1 mixture with ethyl acetate, 23.3 g, 189 mmol) in dichloromethane (1500 mL) and the mixture was stirred at room temperature for 2 hours. A solution of sodium sulfite (45 g) in water (250 mL) was then added to the reaction and the mixture was stirred for 15 minutes, at which point starch/KI indicator paper gave a negative test for the presence of oxidant. The organic layer was separated, dried over MgSO₄ and evaporated to give a pale yellow solid (54 g) which was a ~1:1 mixture of the desired product and m-chlorobenzoic acid (mCBA). This was taken on to the following step without further purification. ¹H NMR (CDCl₃, 400 MHz) δ 3.84 (3H, s), 6.97 (1H, dd), 7.19 (1H, d), 7.34 (1H, t, mCBA), 7.48 (1H, d, mCBA), 7.94 (1H, d, mCBA), 8.04 (1H, s, mCBA), 8.36 (1H, d).

Preparation 21

(5-Methoxypyridin-2-yl)methanol

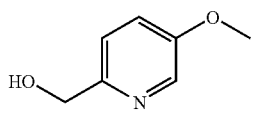

Trifluoroacetic anhydride (28.2 mL, 203 mmol) was added dropwise to an ice cooled solution of the product from preparation 20 (~135 mmol) in dichloromethane (500 mL), the mixture was allowed to warm to room temperature and stirred overnight. Tlc analysis indicated still largely starting material so a further portion of trifluoroacetic anhydride (15 mL, 108 mmol) was added dropwise and the mixture was allowed to stir for a further 27 hours. The reaction was quenched by the cautious addition of methanol (250 mL) and left to stir for 30 minutes before being concentrated in vacuo. 2.5 M sodium hydroxide (100 mL) was then added cautiously and the mixture was extracted with dichloromethane (4×100 mL). The combined organic extracts were dried (MgSO₄) and evaporated to give the desired product (12 g, 64%) contaminated with recovered starting material (~15 mol %). ¹H NMR (CDCl₃, 400 MHz) δ 3.80 (3H, s), 4.40 (1H, br), 4.66 (2H, s), 7.16 (1H, dd), 7.20 (1H, d), 8.17 (1H, d).

Preparation 22

5-Methoxypyridine-2-carbaldehyde

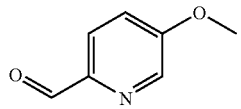

MnO₂ (97.0 g, 360 mmol) was added in one portion to a solution of the alcohol from preparation 21 (12 g, 86 mmol) in dichloromethane (500 mL) and the resulting suspension was stirred at room temperature for 64 hours. The reaction mixture was filtered through Celite® and the solvent was removed in vacuo to give the desired product (8.6 g, 73%) contaminated with 5-methoxy-2-methylpyridine 1-oxide (15 mol %) as an orange oil. ¹H NMR (CDCl₃, 400 MHz) δ 3.93 (3H, s), 7.26 (1H, dd), 7.91 (1H, d), 8.37 (1H, d), 9.94 (1H, s).

The invention claimed is:
1. A compound of formula (I):

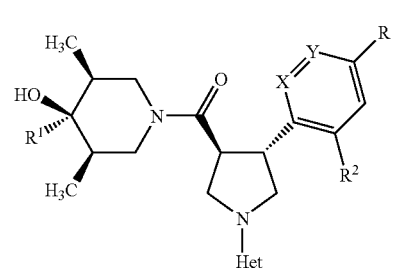

wherein
one of X and Y is N and the other is CH,
R is F, Cl, CN, CF₃ or methoxy, with the proviso that when Y is N, R is not F or Cl,
R¹ is phenyl, 2-pyridyl, C₃-C₆ cycloalkyl or CH₂(C₃-C₆ cycloalkyl), wherein the ring moiety of said phenyl, 2-pyridyl, C₃-C₆ cycloalkyl or CH₂(C₃-C₆ cycloalkyl) is optionally substituted with one to four substituents independently selected from F, Cl, CN, methyl and methoxy,
R² is H, F or Cl, with the proviso that when Y is N, R² is not F or Cl,
Het is a 6-membered ring containing one or 2 N atoms, wherein the ring is either aromatic, or contains 2 double bonds in the ring and a 0 substituent, which ring is optionally substituted with one to four substituents independently selected from F, Cl, OH, CN, methyl, ethyl, NH₂, NHCH₃, N(CH₃)₂ and methoxy,
or alternatively, Het is a 6-membered ring containing one or 2 N atoms fused at the 3,4-positions, relative to the attachment to the pyrrolidine ring, to a 5-membered aromatic ring containing one or two further N atoms, which 5-membered ring is optionally substituted with OH,
or a pharmaceutically acceptable salt thereof.
2. The compound according to claim 1 wherein X is N and Y is CH, or a pharmaceutically acceptable salt thereof.
3. The compound according to claim 1 wherein R is chloro, or a pharmaceutically acceptable salt thereof.

4. The compound according to claim 1, wherein
  R¹ is phenyl optionally substituted by one or more substituents independently selected from F, Cl, CN, methyl and methoxy, or a pharmaceutically acceptable salt thereof.

5. The compound according to claim 4, wherein R¹ is phenyl, 4-chlorophenyl or 4-fluorophenyl, or a pharmaceutically acceptable salt thereof.

6. The compound according to claim 1, wherein
  R¹ is $C_3$-$C_6$ cycloalkyl, or a pharmaceutically acceptable salt thereof.

7. The compound according to claim 6, wherein R¹ is cyclopropyl or cyclohexyl, or a pharmaceutically acceptable salt thereof.

8. The compound according to claim 1, wherein R² is H or F, or a pharmaceutically acceptable salt thereof.

9. The compound according to claim 8, wherein R² is H, or a pharmaceutically acceptable salt thereof.

10. The compound according to claim 1, wherein
  Het is pyridin-2-yl, pyridin-3-yl, pyridazin-3-yl, 6-oxo-1,6-dihydropyridazin-3-yl, 6-oxo-1,6-dihydropyridin-3-yl, 2-oxo-1,2-dihydropyrimidin-4-yl, 6-oxo-1,6-dihydropyrimidin-4-yl, 2-oxo-1,2-dihydropyridin-4-yl, imidazo[1,2-b]pyridazin-6-yl, [1,2,4]triazolo[4,3-b]pyridazin-6-yl or 6-oxo-1,6-dihydropyridin-2-yl, optionally substituted by one to four substituents independently selected from F, Cl, OH, CN, methyl, ethyl and methoxy, or a pharmaceutically acceptable salt thereof.

11. The compound according to claim 10, wherein Het is pyridin-2-yl, pyridin-3-yl, pyridazin-3-yl or 6-oxo-1,6-dihydropyridazin-3-yl, optionally substituted by one to four substituents independently selected from OH, CN, F, methyl and methoxy, or a pharmaceutically acceptable salt thereof.

12. The compound according to claim 11, wherein Het is pyridin-2-yl or pyridazin-3-yl, each of which is substituted at the para-position relative to the bond linking to the pyrrolidine moiety, by OH, CN or methoxy, or a pharmaceutically acceptable salt thereof.

13. The compound according to claim 12, wherein Het is pyridazin-3-yl substituted at the para-position relative to the bond linking to the pyrrolidine moiety, by OH, CN or methoxy, or a pharmaceutically acceptable salt thereof.

14. The compound according to claim 1 selected from:
  6-[(3S,4S)-3-(5-chloropyridin-2-yl)-4-{[(3R,4R,5S)-4-(4-fluorophenyl)-4-hydroxy-3,5-dimethylpiperidin-1-yl]carbonyl}pyrrolidin-1-yl]pyridazine-3-carbonitrile;
  6-[(3S,4S)-3-(5-chloropyridin-2-yl)-4-{[(3R,4R,5S)-4-hydroxy-3,5-dimethyl-4-phenylpiperidin-1-yl]carbonyl}pyrrolidin-1-yl]pyridazine-3-carbonitrile;
  6-[(3S,4S)-3-(5-chloropyridin-2-yl)-4-{[(3R,4R,5S)-4-hydroxy-3,5-dimethyl-4-pyridin-2-ylpiperidin-1-yl]carbonyl}pyrrolidin-1-yl]pyridazine-3-carbonitrile;
  6-[(3S,4S)-3-(5-chloropyridin-2-yl)-4-{[(3R,4R,5S)-4-hydroxy-3,5-dimethyl-4-phenylpiperidin-1-yl]carbonyl}pyrrolidin-1-yl]-2-methylpyridazin-3(2H)-one;
  6-[(3S,4S)-3-(5-chloropyridin-2-yl)-4-{[(3R,4R,5S)-4-hydroxy-3,5-dimethyl-4-phenylpiperidin-1-yl]carbonyl}pyrrolidin-1-yl]-2-methylpyridazin-3(2H)-one;
  6[(3S,4S)-3-{[(3R,4R,5S)-4-(4-chlorophenyl)-4-hydroxy-3,5-dimethylpiperidin-1-yl]carbonyl}-4-(5-chloropyridin-2-yl)pyrrolidin-1-yl]-2-methylpyridazin-3(2H)-one;
  6-[(3S,4S)-3-(5-chloropyridin-2-yl)-4-{[(R3R,4R,5S)-4-(5-chloropyridin-2-yl)-4-hydroxy-3,5-dimethylpiperidin-1-yl]carbonyl}pyrrolidin-1-yl]-2-methylpyridazin-3(2H)-one;
  6-[(3S,4S)-3-(5-chloropyridin-2-yl)-4-{[R3R,4R,5S)-4-(3,4-difluorophenyl)-4-hydroxy-3,5-dimethylpiperidin-1-yl]carbonyl}pyrrolidin-1-yl]-2-methylpyridazin-3(2H)-one;
  6-[(3S,4S)-3-(5-chloropyridin-2-yl)-4-{[(R3R,4R,5S)-4-hydroxy-4-(4-methoxyphenyl)-3,5-dimethylpiperidin-1-yl]carbonyl}pyrrolidin-1-yl]-2-methylpyridazin-3(2H)-one;
  6-[(3S,4S)-3-(5-chloropyridin-2-yl)-4-{[(3R,4R,5S)-4-cyclohexyl-4-hydroxy-3,5-dimethylpiperidin-1-yl]carbonyl}pyrrolidin-1-yl]-2-methylpyridazin-3(2H)-one;
  (3R,4R,5S)-1-{[(3S,4S)-1-(6-chloropyridazin-3-yl)-4-(5-chloropyridin-2-yl)pyrrolidin-3-yl]carbonyl}-4-(4-fluorophenyl)-3,5-dimethylpiperidin-4-ol;
  (3R,4R,5S)-1-{[(3S,4S)-4-(5-chloropyridin-2-yl)-1-(6-methoxypyridazin-3-yl)pyrrolidin-3-yl]carbonyl}-4-cyclopropyl-3,5-dimethylpiperidin-4-ol;
  (3R,4R,5S)-1-{[(3S,4S)-4-(5-chloropyridin-2-yl)-1-(5-fluoropyridin-3-yl)pyrrolidin-3-yl]carbonyl}-4-(4-fluorophenyl)-3,5-dimethylpiperidin-4-ol;
  6-[(3S,4S)-3-(5-chloropyridin-2-yl)-4-{[(3R,4R,5S)-4-(4-fluorophenyl)-4-hydroxy-3,5-dimethylpiperidin-1-yl]carbonyl}pyrrolidin-1-yl]nicotinonitrile;
  6-[(3S,4S)-3-{([(3R,4R,5S)-4-(4-fluorophenyl)-4-hydroxy-3,5-dimethylpiperidin-1-yl]carbonyl}-4-(5-fluoropyridin-2-yl)pyrrolidin-1-yl]pyridazine-3-carbonitrile;
  6-[(3S,4S)-3-(5-fluoropyridin-2-yl)-4-{[(3R,4R,5S)-4-hydroxy-3,5-dimethyl-4-phenylpiperidin-1-yl]carbonyl}pyrrolidin-1-yl]pyridazine-3-carbonitrile;
  6-[(3S,4S)-3-{[(3R,4R,5S)-4-(4-chlorophenyl)-4-hydroxy-3,5-dimethylpiperidin-1-yl]carbonyl}-4-(5-fluoropyridin-2-yl)pyrrolidin-1-yl]pyridazine-3-carbonitrile;
  6-[(3S,4S)-3-{[(3R,4R,5S)-4-(4-chlorophenyl)-4-hydroxy-3,5-dimethylpiperidin-1-yl]carbonyl}-4-(5-fluoropyridin-2-yl)pyrrolidin-1-yl]pyridazin-3(2H)-one;
  6-[(3S,4S)-3-(5-cyanopyridin-2-yl)-4-{[(3R,4R,5S)-4-(4-fluorophenyl)-4-hydroxy-3,5-dimethylpiperidin-1-yl]carbonyl}pyrrolidin-1-yl]pyridazine-3-carbonitrile;
  6-[(3S,4R)-3-{[(3R,4R,5S)-4-(4-fluorophenyl)-4-hydroxy-3,5-dimethylpiperidin-1-yl]carbonyl}-4-(6-methoxypyridin-3-yl)pyrrolidin-1-yl]pyridazine-3-carbonitrile;
  6-[(3S,4S)-3-{[(3R,4R,5S)-4-(4-fluorophenyl)-4-hydroxy-3,5-dimethylpiperidin-1-yl]carbonyl}-4-(5-methoxypyridin-2-yl)pyrrolidin-1-yl]pyridazine-3-carbonitrile;
  (3R,4R,5S)-4-(4-fluorophenyl)-1-{[(3S,4R)-1-(5-fluoropyridin-3-yl)-4-(6-methoxypyridin-3-yl)pyrrolidin-3-yl]carbonyl}-3,5-dimethylpiperidin-4-ol;
  (3R,4R,5S)-1-{[(3S,4S)-4-(5-chloropyridin-2-yl)-1-pyridazin-3-ylpyrrolidin-3-yl]carbonyl}-4-(4-fluorophenyl)-3,5-dimethylpiperidin-4-ol;
  6-[(3S,4S)-3-(5-chloropyridin-2-yl)-4-{([(3R,4R,5S)-4-(4-fluorophenyl)-4-hydroxy-3,5-dimethylpiperidin-1-yl]carbonyl}pyrrolidin-1-yl]pyridazin-3(2H)-one;
  6-[(3S,4S)-3-(5-chloropyridin-2-yl)-4-{([(3R,4R,5S)-4-(4-fluorophenyl)-4-hydroxy-3,5-dimethylpiperidin-1-yl]carbonyl}pyrrolidin-1-yl]-2-methylpyridazin-3(2H)-one;
  (3R,4R,5S)-1-{[(3S,4S)-4-(5-chloropyridin-2-yl)-1-[1,2,4]triazolo[4,3-b]pyridazin-6-ylpyrrolidin-3-yl]carbonyl}-4-(4-fluorophenyl)-3,5-dimethylpiperidin-4-ol;

(3R,4R,5S)-1-{[(3S,4S)-4-(5-chloropyridin-2-yl)-1-imidazo[1,2-b]pyridazin-6-ylpyrrolidin-3-yl]carbonyl}-4-(4-fluorophenyl)-3,5-dimethylpiperidin-4-ol;

4-[(3S,4S)-3-(5-chloropyridin-2-yl)-4-{[(3R,4R,5S)-4-(4-fluorophenyl)-4-hydroxy-3,5-dimethylpiperidin-1-yl]carbonyl}pyrrolidin-1-yl]pyrimidin-2(1H)-one;

4-[(3S,4S)-3-(5-chloropyridin-2-yl)-4-{[(3R,4R,5S)-4-(4-fluorophenyl)-4-hydroxy-3,5-dimethylpiperidin-1-yl]carbonyl}pyrrolidin-1-yl]-1-methylpyrimidin-2(1H)-one;

(3R,4R,5S)-1-{[(3S,4S)-4-(5-chloropyridin-2-yl)-1-(6-methoxypyridazin-3-yl)pyrrolidin-3-yl]carbonyl}-4-(4-fluorophenyl)-3,5-dimethylpiperidin-4-ol;

6-[(3S,4S)-3-(5-chloro-3-fluoropyridin-2-yl)-4-{[(3R,4R,5S)-4-(4-fluorophenyl)-4-hydroxy-3,5-dimethylpiperidin-1-yl]carbonyl}pyrrolidin-1-yl]pyridazine-3-carbonitrile;

6-[(3S,4S)-3-(5-chloro-3-fluoropyridin-2-yl)-4-{[(3R,4R,5S)-4-(4-fluorophenyl)-4-hydroxy-3,5-dimethylpiperidin-1-yl]carbonyl}pyrrolidin-1-yl]pyridazin-3(2H)-one;

6-[(3S,4S)-3-(5-chloro-3-fluoropyridin-2-yl)-4-{[(3R,4R,5S)-4-(4-fluorophenyl)-4-hydroxy-3,5-dimethylpiperidin-1-yl]carbonyl}pyrrolidin-1-yl]-2-methylpyridazin-3(2H)-one;

6-[(3S,4S)-3-(3,5-difluoropyridin-2-yl)-4-{[(3R,4R,5S)-4-(4-fluorophenyl)-4-hydroxy-3,5-dimethylpiperidin-1-yl]carbonyl}pyrrolidin-1-yl]pyridazine-3-carbonitrile;

6-[(3S,4S)-3-(3,5-difluoropyridin-2-yl)-4-{[(3R,4R,5S)-4-(4-fluorophenyl)-4-hydroxy-3,5-dimethylpiperidin-1-yl]carbonyl}pyrrolidin-1-yl]pyridazin-3(2H)-one;

6-[(3S,4S)-3-(3,5-difluoropyridin-2-yl)-4-{[(3R,4R,5S)-4-(4-fluorophenyl)-4-hydroxy-3,5-dimethylpiperidin-1-yl]carbonyl}pyrrolidin-1-yl]-2-methylpyridazin-3(2H)-one;

6-[(3S,4S)-3-{[(3R,4R,5S)-4-(4-chlorophenyl)-4-hydroxy-3,5-dimethylpiperidin-1-yl]carbonyl}-4-(5-chloropyridin-2-yl)pyrrolidin-1-yl]pyridazine-3-carbonitrile;

6-[(3S,4S)-3-(5-chloropyridin-2-yl)-4-{[(3R,4R,5S)-4-(3,4-difluorophenyl)-4-hydroxy-3,5-dimethylpiperidin-1-yl]carbonyl}pyrrolidin-1-yl]pyridazine-3-carbonitrile;

6-[(3S,4S)-3-{[(3R,4R,5S)-4-(4-chlorophenyl)-4-hydroxy-3,5-dimethylpiperidin-1-yl]carbonyl}-4-(5-chloropyridin-2-yl)pyrrolidin-1-yl]pyridazin-3(2H)-one;

6-[(3S,4S)-3-(5-chloropyridin-2-yl)-4-{[(3R,4R,5S)-4-(3,4-difluorophenyl)-4-hydroxy-3,5-dimethylpiperidin-1-yl]carbonyl}pyrrolidin-1-yl]pyridazin-3(2H)-one;

or a pharmaceutically acceptable salt thereof.

15. The compound according to claim 14 selected from:

6-[(3S,4S)-3-5-chloropyridin-2-yl)-4-{[(3R,4R,5S)-4-(4-fluorophenyl)-4-hydroxy-3,5-dimethylpiperidin-1-yl]carbonyl}pyrrolidin-1-yl]pyridazine-3-carbonitrile;

6-[(3S,4S)-3-(5-chloropyridin-2-yl)-4-{[(3R,4R,5S)-4-hydroxy-3,5-dimethyl-4-phenylpiperidin-1-yl]carbonyl}pyrrolidin-1-yl]pyridazine-3-carbonitrile;

6-[(3S,4S)-3-(5-chloropyridin-2-yl)-4-{[(3R,4R,5S)-4-hydroxy-3,5-dimethyl-4-phenylpiperidin-1-yl]carbonyl}pyrrolidin-1-yl]pyridazin-3(2H)-one;

6-[(3S,4S)-3-(5-chloropyridin-2-yl)-4-{[(3R,4R,5S)-4-hydroxy-3,5-dimethyl-4-phenylpiperidin-1-yl]carbonyl}pyrrolidin-1-yl]-2-methylpyridazin-3(2H)-one;

6-[(3S,4S)-3-{[(3R,4R,5S)-4-(4-chlorophenyl)-4-hydroxy-3,5-dimethylpiperidin-1-yl]carbonyl}-4-(5-chloropyridin-2-yl)pyrrolidin-1-yl]-2-methylpyridazin-3(2H)-one;

6-[(3S,4S)-3-(5-chloropyridin-2-yl)-4-{[(3R,4R,5S)-4-(5-chloropyridin-2-yl)-4-hydroxy-3,5-dimethylpiperidin-1-yl]carbonyl}pyrrolidin-1-yl]-2-methylpyridazin-3(2H)-one;

6-[(3S,4S)-3-(5-chloropyridin-2-yl)-4-{[(3R,4R,5S)-4-(3,4-difluorophenyl)-4-hydroxy-3,5-dimethylpiperidin-1-yl]carbonyl}pyrrolidin-1-yl]-2-methylpyridazin-3(2H)-one;

(3R,4R,5S)-1-{[(3S,4S)-4-(5-chloropyridin-2-yl)-1-pyridazin-3-ylpyrrolidin-3-yl]carbonyl}-4-(4-fluorophenyl)-3,5-dimethylpiperidin-4-ol;

6-[(3S,4S)-3-(5-chloropyridin-2-yl)-4-{[(3R,4R,5S)-4-(4-fluorophenyl)-4-hydroxy-3,5-dimethylpiperidin-1-yl]carbonyl}pyrrolidin-1-yl]pyridazin-3(2H)-one;

6-[(3S,4S)-3-(5-chloropyridin-2-yl)-4-{[(3R,4R,5S)-4-(4-fluorophenyl)-4-hydroxy-3,5-dimethylpiperidin-1-yl]carbonyl}pyrrolidin-1-yl]-2-methylpyridazin-3(2H)-one;

(3R,4R,5S)-1-{[(3S,4S)-4-(5-chloropyridin-2-yl)-1-[1,2,4]-triazolo[4,3-b]pyridazin-6-ylpyrrolidin-3-yl]carbonyl}-4-(4-fluorophenyl)-3,5-dimethylpiperidin-4-ol;

(3R,4R,5S)-1-{[(3S,4S)-4-(5-chloropyridin-2-yl)-1-imidazo[1,2-b]pyridazin-6-ylpyrrolidin-3-yl]carbonyl}-4-(4-fluorophenyl)-3,5-dimethylpiperidin-4-ol;

4-[(3S,4S)-3-(5-chloropyridin-2-yl)-4-{[(3R,4R,5S)-4-(4-fluorophenyl)-4-hydroxy-3,5-dimethylpiperidin-1-yl]carbonyl}pyrrolidin-1-yl]pyrimidin-2(1H)-one;

4-[(3S,4S)-3-(5-chloropyridin-2-yl)-4-{[(3R,4R,5S)-4-(4-fluorophenyl)-4-hydroxy-3,5-dimethylpiperidin-1-yl]carbonyl}pyrrolidin-1-yl]-1-methylpyrimidin-2(1H)-one;

6-[(3S,4S)-3-(5-chloro-3-fluoropyridin-2-yl)-4-{[(3R,4R,5S)-4-(4-fluorophenyl)-4-hydroxy-3,5-dimethylpiperidin-1-yl]carbonyl}pyrrolidin-1-yl]pyridazine-3-carbonitrile;

6-[(3S,4S)-3-(5-chloro-3-fluoropyridin-2-yl)-4-{[(3R,4R,5S)-4-(4-fluorophenyl)-4-hydroxy-3,5-dimethylpiperidin-1-yl]carbonyl}pyrrolidin-1-yl]pyridazin-3(2H)-one;

6-[(3S,4S)-3-(5-chloro-3-fluoropyridin-2-yl)-4-{[(3R,4R,5S)-4-(4-fluorophenyl)-4-hydroxy-3,5-dimethylpiperidin-1-yl]carbonyl}pyrrolidin-1-yl]-2-methylpyridazin-3(2H)-one;

6-[(3S,4S)-3-(3,5-d fluoropyridin-2-yl)-4-{[(3R,4R,5S)-4-(4-fluorophenyl)-4-hydroxy-3,5-dimethylpiperidin-1-yl]carbonyl}pyrrolidin-1-yl]pyridazine-3-carbonitrile;

6-[(3S,4S)-3-(3,5-difluoropyridin-2-yl)-4-{[(3R,4R,5S)-4-(4-fluorophenyl)-4-hydroxy-3,5-dimethylpiperidin-1-yl]carbonyl}pyrrolidin-1-yl]pyridazin-3(2H)-one;

6-[(3S,4S)-3-(3,5-difluoropyridin-2-yl)-4-{[(3R,4R,5S)-4-(4-fluorophenyl)-4-hydroxy-3,5-dimethylpiperidin-1-yl]carbonyl}pyrrolidin-1-yl]-2-methylpyridazin-3(2H)-one;

6-[(3S,4S)-3-{[(3R,4R,5S)-4-(4-chlorophenyl)-4-hydroxy-3,5-dimethylpiperidin-1-yl]carbonyl}-4-(5-chloropyridin-2-yl)pyrrolidin-1-yl]pyridazine-3-carbonitrile;

6-[(3S,4S)-3-(5-chloropyridin-2-yl)-4-{[(3R,4R,5S)-4-(3,4-difluorophenyl)-4-hydroxy-3,5-dimethylpiperidin-1-yl]carbonyl}pyrrolidin-1-yl]pyridazine-3-carbonitrile;

6-[(3S,4S)-3-{[(3R,4R,5S)-4-(4-chlorophenyl)-4-hydroxy-3,5-dimethylpiperidin-1-yl]carbonyl}-4-(5-chloropyridin-2-yl)pyrrolidin-1-yl]pyridazin-3(2H)-one; or 6-[(3S,4S)-3-(5-chloropyridin-2-yl)-4-{[(3R,4R,5S)-4-(3,4-difluorophenyl)-4-hydroxy-3,5-dimethylpiperidin-1-yl]carbonyl}pyrrolidin-1-yl]pyridazin-3(2H)-one;

or a pharmaceutically acceptable salt thereof.

16. The compound according to claim 15 selected from:

6-[(3S,4S)-3-(5-chloropyridin-2-yl)-4-{[(3R,4R,5S)-4-(4-fluorophenyl)-4-hydroxy-3,5-dimethylpiperidin-1-yl]carbonyl}pyrrolidin-1-yl]pyridazine-3-carbonitrile;

6-[(3S,4S)-3-{[(3R,4R,5S)-4-(4-chlorophenyl)-4-hydroxy-3,5-dimethylpiperidin-1-yl]carbonyl}-4-(5-chloropyridin-2-yl)pyrrolidin-1-yl]-2-methylpyridazin-3(2H)-one;

6-[(3S,4S)-3-(5-chloropyridin-2-yl)-4-{[(3R,4R,5S)-4-(5-chloropyridin-2-yl)-4-hydroxy-3,5-dimethylpiperidin-1-yl]carbonyl}pyrrolidin-1-yl]-2-methylpyridazin-3(2H)-one;

6-[(3S,4S)-3-(5-chloropyridin-2-yl)-4-{[(3R,4R,5S)-4-(3,4-difluorophenyl)-4-hydroxy-3,5-dimethylpiperidin-1-yl]carbonyl}pyrrolidin-1-yl]-2-methylpyridazin-3(2H)-one;

6-[(3S,4S)-3-(5-chloropyridin-2-yl)-4-{[(3R,4R,5S)-4-(4-fluorophenyl)-4-hydroxy-3,5-dimethylpiperidin-1-yl]carbonyl}pyrrolidin-1-yl]pyridazin-3(2H)-one;

6-[(3S,4S)-3-(5-chloropyridin-2-yl)-4-{[(3R,4R,5S)-4-(4-fluorophenyl)-4-hydroxy-3,5-dimethylpiperidin-1-yl]carbonyl}pyrrolidin-1-yl]-2-methylpyridazin-3(2H)-one;

6-[(3S,4S)-3-{[(3R,4R,5S)-4-(4-chlorophenyl)-4-hydroxy-3,5-dimethylpiperidin-1-yl]carbonyl}-4-(5-chloropyridin-2-yl)pyrrolidin-1-yl]pyridazine-3-carbonitrile;

6-[(3S,4S)-3-(5-chloropyridin-2-yl)-4-{[(3R,4R,5S)-4-(3,4-difluorophenyl)-4-hydroxy-3,5-dimethylpiperidin-1-yl]carbonyl}pyrrolidin-1-yl]pyridazine-3-carbonitrile;

6-[(3S,4S)-3-{[(3R,4R,5S)-4-(4-chlorophenyl)-4-hydroxy-3,5-dimethylpiperidin-1-yl]carbonyl}-4-(5-chloropyridin-2-yl)pyrrolidin-1-yl]pyridazin-3(2H)-one; or 6-[(3S,4S)-3-(5-chloropyridin-2-yl)-4-{[(3R,4R,5S)-4-(3,4-difluorophenyl)-4-hydroxy-3,5-dimethylpiperidin-1-yl]carbonyl}pyrrolidin-1-yl]pyridazin-3(2H)-one;

or a pharmaceutically acceptable salt thereof.

17. A pharmaceutical composition comprising a therapeutically effective amount of a compound according to claim 1, or a pharmaceutically acceptable salt thereof, and a pharmaceutically acceptable diluent, carrier or adjuvant.

18. The compound 6-[(3S,4S)-3-{[(3R,4R,5S)-4-(4-chlorophenyl)-4-hydroxy-3,5-dimethylpiperidin-1-yl]carbonyl}-4-(5-chloropyridin-2-yl)pyrrolidin-1-yl]-2-methylpyridazin-3(2H)-one or a pharmaceutically acceptable salt thereof.

19. A pharmaceutical composition comprising a therapeutically effective amount of 6-[(3S,4S)-3-{[(3R,4R,5S)-4-(4-chlorophenyl)-4-hydroxy-3,5-dimethylpiperidin-1-yl]carbonyl}-4-(5-chloropyridin-2-yl)pyrrolidin-1-yl]-2-methylpyridazin-3(2H)-one or a pharmaceutically acceptable salt thereof and a pharmaceutically acceptable diluent, carrier or adjuvant.

* * * * *